United States Patent
Boyce

(12)
(10) Patent No.: US 6,281,009 B1
(45) Date of Patent: *Aug. 28, 2001

(54) USE OF A NON-MAMMALIAN DNA VIRUS TO EXPRESS AN EXOGENOUS GENE IN A MAMMALIAN CELL

(75) Inventor: Frederick M. Boyce, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/927,318

(22) Filed: Sep. 11, 1997

Related U.S. Application Data

(60) Provisional application No. 60/026,294, filed on Sep. 11, 1996.

(51) Int. Cl.$^7$ .............. C12N 15/00; C12N 9/00; A61K 38/00; C07H 21/04

(52) U.S. Cl. .......... 435/320.1; 514/12; 435/183; 435/69.1; 435/257.3; 435/325; 536/23.2; 536/23.5

(58) Field of Search .............. 435/183, 69.1, 435/320.1, 257.3, 325; 514/12; 536/23.2, 23.5

(56) References Cited

U.S. PATENT DOCUMENTS

| 4,745,051 | 5/1988 | Smith et al. | 435/68 |
|---|---|---|---|
| 4,879,236 | 11/1989 | Smith et al. | 435/235 |
| 4,914,027 | 4/1990 | Knapp et al. | 435/69.6 |
| 5,004,687 | 4/1991 | Miller | 435/69.1 |
| 5,106,741 | 4/1992 | Marotti et al. | 435/226 |
| 5,476,781 | 12/1995 | Moyer et al. | 435/240.2 |

FOREIGN PATENT DOCUMENTS

| WO 92/14829 | 9/1992 | (WO) . |
|---|---|---|
| WO 95/23866 | 9/1995 | (WO) . |
| WO 95/26409 | 10/1995 | (WO) . |
| WO 96/09074 | 3/1996 | (WO) . |

OTHER PUBLICATIONS

Yi Li, et al., Transient, Nonlethal Expression of Genes in Vertebrate Cells by Recombinant Entomopoxviruses, Journal of Virology, Dec. 1997, pp. 9557–9562.

Yvan Boublik, et al., Eukaryotic Virus Display: Engineering the Major Surface Glycoprotein of the Autographa californica Nuclear Polyhedrosis Virus (AcNPV) for the Presentation of Foreign Proteins on the Virus Surface, Bio/Technology, vol. 13, pp. 1079–1984, Oct. 1995.

Fraser, M.J., The baculovirus–infected insect cell as a eukaryotic gene expression system, Curr. Top. Microbiol. Immunol., 158:131–172 (1992).

Young J.A.T. et al., "Efficient Incorporation of Human CD4 Protein into Avian Leukosis Virus Particles"; *Science* 250:1421–1423 (1990).

(List continued on next page.)

*Primary Examiner*—Hankyel Park
(74) *Attorney, Agent, or Firm*—Fish & Richardson P.C.

(57) ABSTRACT

Disclosed are methods, nucleic acids, and cells for expressing an exogenous gene in a mammalian cell, involving introducing into the cell a non-mammalian DNA virus (e.g., a baculovirus) whose genome carries an exogenous gene, and growing the cell under conditions such that the gene is expressed. Also disclosed are methods for treating gene deficiency disorders, neurological disorders, or cancers in a mammal by providing to a cell a therapeutically effective amount of a virus whose genome carries an exogenous, therapeutic gene and growing the cell under conditions such that the exogenous gene is expressed in the mammal.

75 Claims, 17 Drawing Sheets

OTHER PUBLICATIONS

James Barsoum, et al., Efficient Transduction of Mammalian Cells by a Recombinant Baculovirus Having the Vesicular Stomatitis Virus G Glycoprotein, Human Gene Therapy, 8:2011–2018 (Nov. 20, 1997).

Miguel A. Trujillo, et al., Functional analysis of a liver–specific enhancer of the hepatitis B virus Proc. Natl. Acad. Sci., 88:3797–3801, (May 1991).

Volkman, et al,; "In Vitro Survey of Autographa Californica Nuclear Polyhedrosis Virus Interaction with Nontarget Vetebrate Host Cells", applied and Environmental Microbiology, 45:1085–1093, 1983.

Brusca et al., "Autographa Californica Nuclear Polyhedrosis Virus Efficiently Enters but Does Not Replicate in Poikilothermic Vertebrate Cells", Intervirology 26:207–222, 1986.

Hoopes et al., "In Vitro Transcription of Baculovirus Immediate Early Genes: Accurate mRNA Initiation By Nuclear Extracts from Both Insect and Human Cells", Proc. Natl. Acad. Sci., 88:4513–4517, 1991.

Huber et al., "Retroviral–mediated Gene Therapy for the Treatment of Hepatocellular Carcinoma: An Innovative Approach for Cancer Therapy", Proc. Natl. Acad. Sci., 88:8039–8043, 1991.

Patel et al., "A New Method for the Isolation of Recombinant Baculovirus", Nucleic Acids Research, 20:97–104 1992.

Rana et al., "Cell–Extracellular Matrix Interactions Can Regulate the Switch Between Growth and Differentiation in Rat Hepatocytes . . . ", Molecular and Cellular Biology, 14:5858–5869, 1994.

Tjia et al., "Autographa Californica Nuclear Polyhedrosis Virus (AcNPV) DNA Does Not Persist in Mass Cultures of Mammalian Cells", Virology, 125:107–117, 1983.

Vile et al., "Gene Transfer Technologies for the Gene Therapy of Cancer", Gene Therapy, 1:88–98, 1994.

School of Biological Sciences, Canberra, Australia, 1991.

Boyce, F.M. et al. (1996) "Baculovirus–Mediated Gene Transfer Into Mammalian Cells", Proc. Nat'l. Acad. Sci., USA 93:2348–2352.

Chan–Choo Yap, et al., A Hybrid Baculovirus–T7 RNA Polymerase System for Recovery of an Infectious Virus from cDNA, Virology, 231:192–200 (1997).

Ashwell G. et al.; "Carbohydrate–Specific Receptors of the Liver"; Ann. Rev. Biochem. 51:531–54 (1982).

Blissard G.W. et al.; "Baculovirus Diversity and Molecular Biology"; Annu. Rev. Entomol. 35:127–55 (1990).

Blissard G.W. et al.; "Baculovirus gp64 Envelope Glycoprotein Is Sufficient To Mediate pH–Dependent Membrane Fusion"; J. of Virology 66:6829–6835 (1992).

Burhans W.C. et al.; "DNA Replication Origins in Animal Cells:A Question of Context?"; Science 263:639–640 (1994).

Burns J.C. et al.; "Vesicular Stomatitis Virus G Glycoprotein Pseudotyped Retroviral Vectors:Concentration to Very High Titer and Efficient Gene Transfer into . . . "; Proc. Natl. Acad. Sci. USA; 90:8033–8037 (1993).

Carbonell L.F. et al.; "Baculovirus–Mediated Expression of Bacterial Genes in Dipteran and Mammalian Cells" Journal of Virology, 56:153–160 (1985).

Carbonell L.F. et al.; "Baculovirus Interaction with Nontarget Organisms:A Virus–Borne Reporter Gene Is Not Expressed in Two Mammalian Cell Lines"; Applied and Environmental Microbiology 53:1412–1417 (1987).

Charreau B. et al; "Establishment of Porcine Cell Lines Producing a Murine Recombinant Retrovirus in Order to Transfer the nislacZ Gene into Porcine Cells", Res. Virol. 142:343–351 (1991).

Cotten M. et al.; "Receptor–Mediated Transport of DNA into Eukaryotic Cells", Academic Press, Inc. 217:618–644 (1993).

Cristiano R.J. et al.; "Hepatic Gene Therapy:Adenovirus Enhancement of Receptor–Mediated Gene Delivery and Expression in Primary Hepatocytes"; Proc. Natl. Acad. Sci. USA 90:2122–2126 (1993).

Demarquoy J.; "Retroviral–Mediated Gene Therapy for the Treatment of Citrullinemia. Transfer and Expression of Argininosuccinate Synthetase in Human Hematopoietic Cells"; Experientia 49:345–348 (1993).

Demetriou A.A. et al.; "Replacement of Liver Function in Rats by Transplantation of Microcarrier–Attached Hepatocytes"; Science 233:1190–1192 (1986).

Grompe M. et al.; "Gene Therapy in Man and Mice:Adenosine Deaminase Deficiency, Ornithine Transcarbamylase Deficiency, and Duchenne Muscular Dystrophy"; Adv. in Experimental Medicine & Biology 3098:51–56 (1991).

Grompe M. et al.; "Retroviral–Mediated Gene Transfer of Human Ornithine Transcarbamylase into Primary Hepatocytes of spf and spf–ash Mice"; Human Gene Therapy 3:35–44 (1992).

Groner, et. al; "Interaction of Autographa californica Nuclear Polyhedrosis Virus with Two Nonpermissive Cell Lines"; Intervirology 21:203–209 (1984).

Hartig P.C. et al.; "Insect Virus:Assays for Toxic Effects and Transformation Potential in Mammalian Cells"; Applied and Enviornmental Microbiology 55:1916–1920 (1989).

Hartig P.C. et al.; "Insect Virus:Assays for Viral Replication and Persistence in Mammalian Cells"; J. Virological Methods 31:335–344 (1991).

Hata A. et al.; "Structure of the Human Ornithine Transcarbamylase Gene"; J. Biochem (Tokyo) 103:302–308.

Hodges P.E. et al.; "The spf$^{ash}$ Mouse:A Missense Mutation in the Ornithine Transcarbamylase Gene Also Causes Aberrant mRNA Splicing"; Proc. Natl. Acad. Sci. USA 86:4142–4146 (1989).

Horwich A.L.; "Inherited Hepatic Enzyme Defects as Candidates for Liver–Directed Gene Therapy"; Current Topics in Microbiology and Immuunology 168:185–200 (1991).

Jones S.N. et al.; "Ectopic Correction of Ornithine Transcarbamylase Deficiency in Sparse Fur Mice"; J. Biological Chemistry 265:14684–14690 (1990).

Jung, et al.; "A Novel β–Galactoside–Binding Lectin in Adult Rat Kidney"; J. Biochem. 116:547–553 (1994).

Kasahara, et al.; "Tissue–Specific Targeting of Retroviral Vectors Through Ligand–Receptor Interactions"; Science 266:1373–1376 (1994).

Lodish H.F.; "Recognition of Complex Oligosaccharides by the Multi–Subunit Asialoglycoprotein Receptor"; Elsevier Science Publishers 374–377 (1991).

Maestri N.E. et al.; "Prospective Treatment of Urea Cycle Disorders"; J. of Pediatrics 119:923–928 (1991).

McGrane M.M. et al.; "Metabolic Control of Gene Expression:In Vivo Studies With Transgenic Mice"; Elsevier Science Publishers 17:40–44 (1992).

Midoux P. et al.; "Specific Gene Transfer Mediated by Lactosylated Poly–L–Lysine into Hepatoma Cells"; Nucleic Acids Research 21:871–878 (1993).

Mulligan R.C.; "The Basic Science of Gene Therapy"; *Science* 260:926–932 (1993).

Shen R. et al.; "Tissue–Specific Regulation of Human $\alpha_1$–Antitrypsin Gene Expression in Transgenic Mice"; *DNA* 8:101–108 (1989).

Shimada T. et al.; "Correction of Ornithine Transcarbamylase (OTC) Deficiency in spf–ash Mice by Introduction of Rat OTC Gene"; *Elsevier Science Publishers* 279:198–200 (1991).

Spiess, Martin; "The Asialoglycoprotein Receptor: A Model for Endocytic Transport Receptors"; *Biochemistry* 29:10009–10018 (1990).

Stratford–Perricaudet et al.; "Evaluation of the Transfer and Expression in Mice of an Enzyme–Encoding Gene Using a Human Adenovirus Vector"; *Human Gene Therapy* 1:241–256 (1990).

Tan S.; "Liver–Specific and Position–Effect Expression of a Retinol–Binding Protein–lacZ Fusion Gene (RBP–lacZ) in Transgenic Mice"; *Developmental Biology* 146:24–37 (1991).

Ikuo Shoji, et al., Efficient gene transfer into various mammalian cells, including non–hepatic cells, by baculovirus vectors, Journal of General Virology, 78:2657–2664 (1997).

Wagner E. et al.; "Transferrin–Polycation Conjugates as Carriers for DNA Uptake into Cells"; *Proc. Natl. Acad. Sci. USA* 87:3410–3414 (1990).

Wilson J.M. et al.; "A Novel Mechanism for Achieving Transgene Persistence in Vivo After Somatic Gene Transfer into Hepatocytes"; *Journal of Biological Chemistry* 267:11483–11489 (1992).

Wilson J.M. et al.; "Hapatocyte–Directed Gene Transfer In Vivo Leads to Transient Improvement of Hypercholesterolemia in Low Density Lipoprotein . . . "; *J. Biol. Chemistry* 267:963–967 (1992).

Wu G.Y. et al.; "Evidence for Targeted Gene Delivery to Hep G2 Hepatoma Cells in Vitro"; *Biochemistry* 27:887–892 (1988).

Wu G.Y. et al.; "Receptor–Mediated Gene Delivery and Expression in Vivo"; 263:14621–14624 (1988).

Wu G.Y. et al.; "Receptor–Mediated Gene Delivery in Vivo"; *J. Biological Chemistry* 266:14338–14342 (1991).

Wu G.Y. et al.; "Receptor–Mediated in Vitro Gene Transformation by a Soluble DNA Carrier System"; *J. Biological Chemistry* 262:4429–4432 (1987).

Wu G.Y. et al.; "Targeting Genes: Delivery and Persistent Expression of a Foreign Gene Driven by Mammalian Regulatory Elements in Vivo"; *J. Biological Chemistry* 264:16985–16987 (1989).

Barbara Glocker, et al., In Vitro Transactivation of Baculovirus Early Genes by Nuclear Extracts from Autographa californica Nuclear Polyhedrosis Virus–Infected Spodoptera frugiperda Cells, Journal of Virology, 3476–3484 (Jun. 1992).

FIG. 14A    FIG. 14B
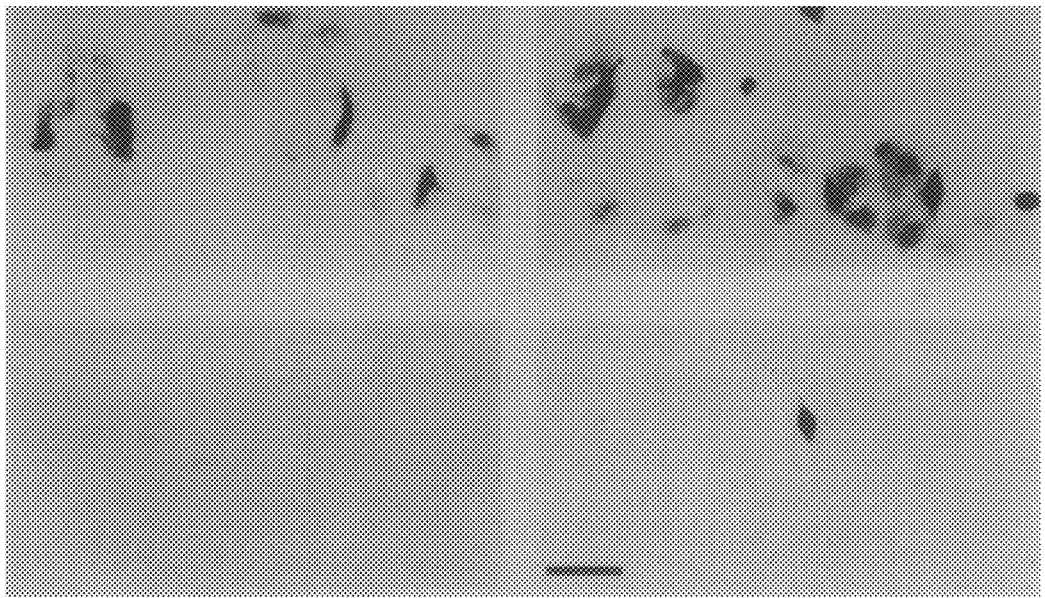
FIG. 14C    FIG. 14D
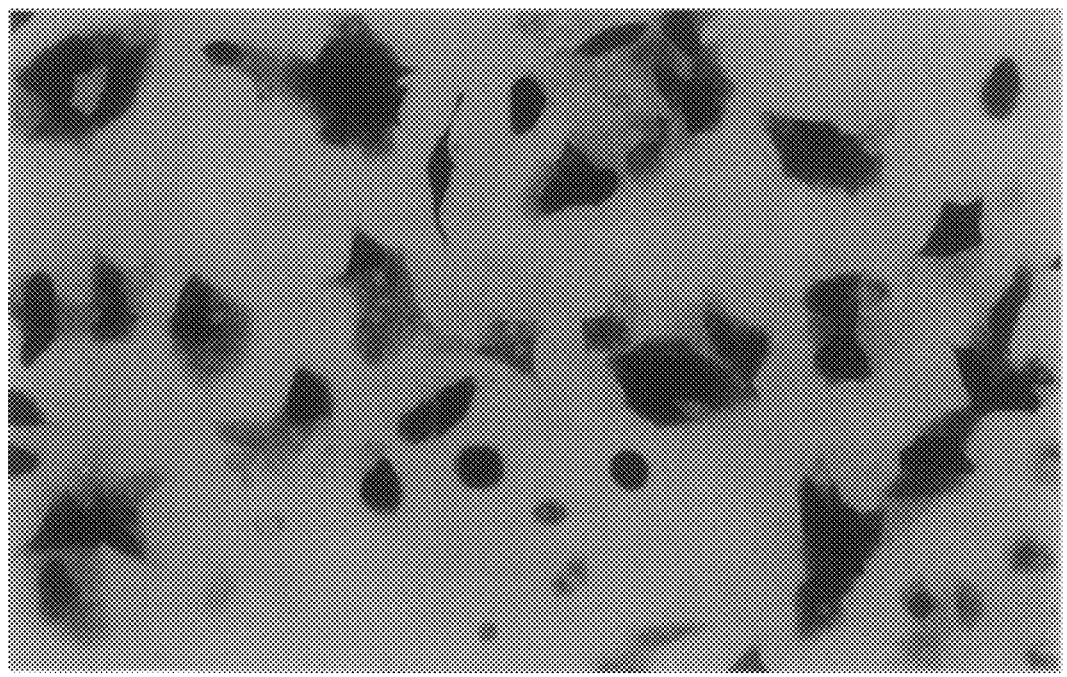
FIG. 15

USE OF A NON-MAMMALIAN DNA VIRUS TO EXPRESS AN EXOGENOUS GENE IN A MAMMALIAN CELL

CROSS-REFERENCE TO RELATED APPLICATION

This application claims priority under 35 U.S.C. § 119 from U.S. Ser. No. 60/026,294, filed Sep. 11, 1996.

BACKGROUND OF THE INVENTION

This invention relates to the use of a non-mammalian DNA virus to express an exogenous gene in a mammalian cell.

Current methods for expressing an exogenous gene in a mammalian cell include the use of mammalian viral vectors, such as those that are derived from retroviruses, adenoviruses, herpes viruses, vaccinia viruses, polio viruses, or adeno-associated viruses. Other methods of expressing an exogenous gene in a mammalian cell include direct injection of DNA, the use of ligand-DNA conjugates, the use of adenovirus-ligand-DNA conjugates, calcium phosphate precipitation, and methods that utilize a liposome- or polycation-DNA complex. In some cases, the liposome- or polycation-DNA complex is able to target the exogenous gene to a specific type of tissue, such as liver tissue.

Typically, viruses that are used to express desired genes are constructed by removing unwanted characteristics from a virus that is known to infect, and replicate in, a mammalian cell. For example, the genes encoding viral structural proteins and proteins involved in viral replication often are removed to create a defective virus, and a therapeutic gene is then added. This principle has been used to create gene therapy vectors from many types of animal viruses such as retroviruses, adenoviruses, and herpes viruses. This method has also been applied to Sindbis virus, an RNA virus that normally infects mosquitoes but which can replicate in humans, causing a rash and an arthritis syndrome.

Non-mammalian viruses have been used to express exogenous genes in non-mammalian cells. For example, viruses of the family Baculoviridae (commonly referred to as baculoviruses) have been used to express exogenous genes in insect cells. One of the most studied baculoviruses is *Autographa californica* multiple nuclear polyhedrosis virus (AcMNPV). Although some species of baculoviruses that infect crustacea have been described (Blissard, et al., 1990, Ann. Rev. Entomology 35:127), the normal host range of the baculovirus AcMNPV is limited to the order lepidoptera. Baculoviruses have been reported to enter mammalian cells (Volkman and Goldsmith, 1983, Appl. and Environ. Microbiol. 45:1085–1093; Carbonell and Miller, 1987, Appl. and Environ. Microbiol. 53:1412–1417; Brusca et al., 1986, Intervirology 26:207–222; and Tjia et al., 1983, Virology 125:107–117). Although an early report of baculovirus-mediated gene expression in mammalian cells appeared, the authors later attributed the apparent reporter gene activity to the reporter gene product being carried into the cell after a prolonged incubation of the cell with the virus (Carbonell et al., 1985, J. Virol. 56:153–160; and Carbonell and Miller, 1987, Appl. and Environ. Microbiol. 53:1412–1417). These authors reported that, when the exogenous gene gains access to the cell as part of the baculovirus genome, the exogenous gene is not expressed de novo. Subsequent studies have demonstrated baculovirus-mediated gene expression in mammalian cells (Boyce and Bucher, 1996, Proc. Natl. Acad. Sci. 93:2348–2352). In addition to the Baculoviridae, other families of viruses naturally multiply only in invertebrates; some of these viruses are listed in Table 1.

Gene therapy methods are currently being investigated for their usefulness in treating a variety of disorders. Most gene therapy methods involve supplying an exogenous gene to overcome a deficiency in the expression of a gene in the patient. Other gene therapy methods are designed to counteract the effects of a disease. Still other gene therapy methods involve supplying an antisense nucleic acid (e.g., RNA) to inhibit expression of a gene of the host cell (e.g., an oncogene) or expression of a gene from a pathogen (e.g., a virus).

Certain gene therapy methods are being examined for their ability to correct inborn errors of the urea cycle, for example (see, e.g., Wilson et al., 1992, J. Biol. Chem. 267: 11483–11489). The urea cycle is the predominant metabolic pathway by which nitrogen wastes are eliminated from the body. The steps of the urea cycle are primarily limited to the liver, with the first two steps occurring within hepatic mitochondria. In the first step, carbamoyl phosphate is synthesized in a reaction that is catalyzed by carbamoyl phosphate synthetase I (CPS-I). In the second step, citrulline in formed in a reaction catalyzed by ornithine transcarbamylase (OTC). Citrulline then is transported to the cytoplasm and condensed with aspartate into arginosuccinate by arginosuccinate synthetase (AS). In the next step, arginosuccinate lyase (ASL) cleaves arginosuccinate to produce arginine and fumarate. In the last step of the cycle, arginase converts arginine into ornithine and urea.

A deficiency in any of the five enzymes involved in the urea cycle has significant pathological effects, such as lethargy, poor feeding, mental retardation, coma, or death within the neonatal period (see, e.g., Emery et al., 1990, In: Principles and Practice of Medical Genetics, Churchill Livingstone, New York). OTC deficiency usually manifests as a lethal hyperammonemic coma within the neonatal period. A deficiency in AS results in citrullinemia which is characterized by high levels of citrulline in the blood. The absence of ASL results in arginosuccinic aciduria (ASA), which results in a variety of conditions including severe neonatal hyperammonemia and mild mental retardation. An absence of arginase results in hyperarginemia which can manifest as progressive spasticity and mental retardation during early childhood. Other currently used therapies for hepatic disorders include dietary restrictions; liver transplantation; and administration of arginine freebase, sodium benzoate, and/or sodium phenylacetate.

SUMMARY OF THE INVENTION

It has been discovered that a non-mammalian DNA virus carrying an exogenous gene expression construct can be used to express an exogenous gene in a mammalian cell.

Accordingly, in one aspect, the invention features a method of expressing an exogenous gene in a mammalian cell(s), involving introducing into the cell a non-mammalian DNA virus, the genome of which carries the exogenous gene operably linked to a mammalian-active promoter, and allowing the cell to live under conditions such that the exogenous gene is expressed.

In another aspect, the invention features a method of treating a gene deficiency disorder in a mammal (e.g., a human or a mouse), involving introducing into a cell a therapeutically effective amount of a non-mammalian DNA virus, the genome of which carries an exogenous gene, and maintaining the cell under conditions such that the exogenous gene is expressed in the mammal.

Included within the invention are nucleic acids and cells for practicing the methods described herein. In particular, the invention includes a nucleic acid that includes a genome of a non-mammalian DNA virus (e.g., an insect virus) and an exogenous mammalian gene that is operably linked to a "mammalian-active" promoter. Such a nucleic acid can be engineered to carry any of the various promoters and exogenous genes described herein. Particularly useful nucleic acids are those that express a therapeutic gene. Other useful genes include, but are not limited to, RNA decoy genes, ribozyme genes, and antisense genes (i.e., genes that are transcribed into RNA decoys, ribozymes, or antisense nucleic acids). If desired, the nucleic acids of the invention can be formulated into a pharmaceutical composition by admixture with a pharmaceutically acceptable excipient. Also included within the invention is a cell (e.g., a cultured, human cell) that contains any of the nucleic acids of the invention.

The invention further features a method for treating a tumor in a mammal, involving introducing into a cancerous cell of the mammal (e.g., a cancerous hepatocyte) a non-mammalian DNA virus (e.g., a baculovirus) whose genome expresses a cancer-therapeutic gene (encoding, e.g., a tumor necrosis factor, thymidine kinase, diphtheria toxin chimera, or cytosine deaminase). The exogenous gene can be expressed in a variety of cells, e.g., hepatocytes; neural cells such as neurons from brain, spinal cord, or peripheral nerve; adrenal medullary cells; glial cells; skin cells; spleen cells; muscle cells; kidney cells; and bladder cells. Thus, the invention can be used to treat various cancerous or non-cancerous tumors, including carcinomas (e.g., hepatocellular carcinoma), sarcomas, gliomas, and neuromas. Either in vivo or in vitro methods can be used to introduce the virus into the cell in this aspect of the invention. Preferably, the exogenous gene is operably linked to a promoter that is active in cancerous cells, but not in other cells, of the mammal. For example, the α-fetoprotein promoter is active in cells of hepatocellular carcinomas and in fetal tissue but it is otherwise not active in mature tissues. Accordingly, the use of such a promoter is preferred for expressing a cancer-therapeutic gene for treating hepatocellular carcinomas.

The invention also features a method for treating a neurological disorder (e.g., Parkinson's Disease, Alzheimer's Disease, or disorders resulting from injuries to the central nervous system) in a mammal. The method involves (a) introducing into a cell (e.g., a cell of the central nervous system) a therapeutically effective amount of a non-mammalian DNA virus (e.g., a baculovirus), the genome of which virus includes an exogenous gene encoding a therapeutic protein, and (b) maintaining the cell under conditions such that the exogenous gene is expressed in the mammal. Particularly useful exogenous genes include those that encode therapeutic proteins such as nerve growth factor, hypoxanthine guanine phosphoribosyl transferase (HGPRT), tyrosine hydroxylase, dopadecarboxylase, brain-derived neurotrophic factor, and basic fibroblast growth factor. Both neuronal and non-neuronal cells (e.g., fibroblasts, myoblasts, and kidney cells) are useful in this aspect of the invention. Such cells can be autologous or heterologous to the treated mammal. Preferably, the cell is autologous to the mammal, as such cells obviate concerns about graft rejection. Preferably, the cell is a primary cell, such as a primary neuronal cell or a primary myoblast.

In each aspect of the invention, the non-mammalian DNA virus is preferably an invertebrate virus (i.e., a virus that infects, and replicates in, cells of invertebrates. For example, the DNA viruses listed in Table 1 can be used in the invention. Preferably, the invertebrate DNA virus is a baculovirus, e.g., a nuclear polyhedrosis virus, such as an *Autographa californica* multiple nuclear polyhedrosis virus. If desired, the nuclear polyhedrosis virus may be engineered such that it lacks a functional polyhedrin gene. Either or both the occluded form and budded form of virus (e.g., baculovirus) can be used.

TABLE 1

NON-MAMMALIAN DNA VIRUSES THAT CAN BE USED IN THE INVENTION.[1]

I. FAMILY: BACULOVIRUSES     BACULOVIRIDAE
SUBFAMILY:
OCCLUDED BACULOVIRUSES     EUBACULOVIRINAE
    Genus:
        Nuclear polyhedrosis virus (NPV)
            Subgenus:
                Multiple Nucleocapsid Viruses (MNPV)
        Preferred Species:
            *Autographa californica* nuclear polyhedrosis virus
                (AcMNPV)
        Other Members:
            *Choristoneura fumiferana* MNPV (CfMNPV)
            *Mamestra brassicae* MNPV (MbMNPV)
            *Orgyia pseudotsugata* MNPV (OpMNPV)
            and approximately 400–500 species
            isolated from seven insect orders and Crustacea.
            Subgenus:
                Single Nucleocapsid Viruses (SNPV)
        Preferred Species:
            *Bombyx mori* S Nuclear Polyhedrosis Virus (BmNPV)
        Other Members:
            *Heliothis zea* SNPV (HzSnpv)
            *Trichoplusia ni* SNPV (TnSnpv)
            and similar viruses isolated from seven insect
                orders and Crustacea.
    Genus:
        Granulosis virus (GV)
        Preferred Species:
            *Plodia interpunctella* granulosis virus (PiGV)
        Other Members:
            *Trichoplusia ni* granulosis virus (TnGV)

TABLE 1-continued

NON-MAMMALIAN DNA VIRUSES THAT CAN BE USED IN THE INVENTION.[1]

*Pieris brassicae* granulosis virus (PbGV)
      *Artogeia rapae* granulosis virus (ArGV)
      *Cydia pomonella* granulosis virus (CpGV)
      and similar viruses from about 50 species in the
         Lepidoptera SUBFAMILY:
NON-OCCLUDED BACULOVIRUSES      NUDIBACULOVIRINAE
    Genus:
        Non-occluded baculoviruses (NOB)
        Preferred Species:
           *Heliothis zea* NOB (HzNOB)
        Other Members:
           *Oryctes rhinoceros* virus
              Additional viruses have been observed in a fungus
      (*Strongwellsea magna*), a spider, the European crab
      (*Carcinus maenas*), and the blue crab (*Callinectes*
      sapidus).
II. FAMILY: ICOSAHEDRAL CYTOPLASMIC DEOXYRIBOVIRUSES IRZDOVIRIDAE
    Genus:
        Small iridescent Iridovirus insect virus group
        Preferred Species:
           *Chilo iridescent* virus
        Other Members:

| | |
|---|---|
| Insect iridescent virus 1 | Insect iridescent virus 2 |
| Insect iridescent virus 6 | Insect iridescent virus 9 |
| Insect iridescent virus 10 | Insect iridescent virus 16 |
| Insect iridescent virus 17 | Insect iridescent virus 18 |
| Insect iridescent virus 19 | Insect iridescent virus 20 |
| Insect iridescent virus 21 | Insect iridescent virus 22 |
| Insect iridescent virus 23 | Insect iridescent virus 24 |
| Insect iridescent virus 25 | Insect iridescent virus 26 |
| Insect iridescent virus 27 | Insect iridescent virus 28 |
| Insect iridescent virus 29 | Insect iridescent virus 30 |
| Insect iridescent virus 31 | Insect iridescent virus 32 |

Genus:
        Large iridescent Chloriridovirus insect virus group
        Preferred Species:
           Mosquito iridescent virus (iridescent virus - type
           3, regular strain)
        Other Members:

| | |
|---|---|
| Insect iridescent virus 3 | Insect iridescent virus 4 |
| Insect iridescent virus 5 | Insect iridescent virus 7 |
| Insect iridescent virus 8 | Insect iridescent virus 11 |
| Insect iridescent virus 12 | Insect iridescent virus 13 |
| Insect iridescent virus 14 | Insect iridescent virus 15 |

Putative member:
           *Chironomus plumosus* iridescent
    Genus:
        Frog virus group      Ranavirus
        Preferred Species:
           Frog virus 3 (FV3)
        Other Members:

| | | | |
|---|---|---|---|
| Frog virus 1 | Frog virus 2 | | Frog virus 5 |
| Frog virus 6 | Frog virus 7 | | Frog virus 8 |
| Frog virus 9 | Frog virus 10 | | Frog virus 11 |
| Frog virus 12 | Frog virus 13 | | Frog virus 14 |
| Frog virus 15 | Frog virus 16 | | Frog virus 17 |
| Frog virus 18 | Frog virus 19 | | Frog virus 20 |
| Frog virus 21 | Frog virus 22 | | Frog virus 23 |
| Frog virus 24 | L2 | L4 | L5 |
| LT 1 | LT 2 | LT 3 | LT 4 |
| T 21 | T 6 | T 7 | T 8 |
| T 9 | T 10 | T 11 | T 12 |
| T 13 | T 14 | T 15 | T 16 |
| T 17 | T 18 | T 19 | T 20 |

Tadpole edema virus from newts
Tadpole edema virus from *Rana catesbriana*
Tadpole edema virus from Xenopus
    Genus:
        Lymphocystis disease virus group
Lymphocystisvirus
        Preferred Species:
           Flounder isolate (LCDV-1)
        Other Members:
           Lymphocystis disease virus dab isolate (LCDV-2)
        Putative member:
           Octopus vulgaris disease virus TABLE 1-continued

NON-MAMMALIAN DNA VIRUSES THAT CAN BE USED IN THE INVENTION.[1]

Genus
    Goldfish virus group
    Preferred Species:
        Goldfish virus 1 (GFV-1)
    Other Member:
        Goldfish virus 2 (GF-2)

III. FAMILY: PARVOVIRIDAE
    Genus
        Insect parvovirus group Densovirus
        Preferred Species:
            *Galleria densovirus*
        Other Members:
            *Junonia Densovirus*
            *Agraulis Densovirus*
            *Bombyx Densovirus*
            *Aedes Densovirus*
        Putative Members:

| | |
|---|---|
| *Acheta Densovirus* | *Simulium Densovirus* |
| *Diatraea Densovirus* | *Euxoa Densovirus* |
| *Leucorrhinia Densovirus* | *Periplanata Densovirus* |
| *Pieris Densovirus* | *Sibine Densovirus* |

PC 84 (parvo-like virus from the crab
            *Carcinus mediterraneus*)
            Hepatopancreatic parvo-like virus of
            penaeid shrimp IV. FAMILY: POXVIRUS GROUP    POXVIRIDAE
SUBFAMILY:
POXVIRUSES OF VERTEBRATES    CHORDOPOXVIRINAE
    Genus:
        *Molluscum contagiosum* subgroup    Molluscipoxvirus
        Preferred Species:
            *Molluscum contagiosum* virus SUBFAMILY:
POXVIRUS OF INSECTS    ENTOMOPOXVIRINAE
    Putative Genus:
        Entomopoxvirus A    Poxvirus of Coleoptera
        Preferred Species:
            Poxvirus of Melolontha
        Other Members:
            Coleoptera:
                *Anomala cuprea*
                *Aphodius tasmaniae*
                *Demodema boranensis*
                *Dermolepida albohirtum*
                *Figulus sublaevis*
                *Geotrupes sylvaticus*
    Putative Genus:
        Entomopoxvirus B    Poxvirus of Lepidoptera and
        Orthoptera
        Preferred Species:
            Poxvirus of *Amsacta moorei* (Lepidoptera)
        Other Members:
            Lepidoptera:
                *Acrobasis zelleri*
                *Choristoneura biennis*
                *Choristoneura conflicta*
                *Choristoneura diversuma*
                *Chorizagrotis auxiliaris*
                *Operophtera brumata*
            Orthoptera:
                *Arphia conspersa*
                *Locusta migratoria*
                *Melanopius sanguinipes*
                *Oedaleus senugalensis*
                *Schistocerca gregaria*
    Putative Genus:
      Entomopoxvirus C    Poxvirus of Diptera
      Preferred Species:
            Poxvirus of *Chironomus luridus* (Diptera)
        Other Members:
            Diptera:
                *Aedes aegypti*
                *Camptochironomus tentans*
                *Chironomus attenuatus*
                *Chironomus plumosus*
                *Goeldichlronomus holoprasimus*
        Other members of family Poxviridae

TABLE 1-continued

NON-MAMMALIAN DNA VIRUSES THAT CAN BE USED IN THE INVENTION.[1]

Albatrosspox (Avipoxvirus)
        Cotia
        Embu
        Marmosetpox
        Marsupialpox (Australian 'quokkas')
        Mule deer poxvirus *(Odocoileus hemionus*; Capripoxvirus)
        Volepox (*Microtus oeconomus, Microtus pennsylvanicus*)
        Skunk poxvirus (Mephitis; Orthopoxvirus)

V. GROUP CAULIFLOWER CAULIMOVIRUS MOSAIC VIRUS
    Preferred Member:
        Cauliflower mosaic virus (CaMV) (cabbage b, davis isolate)
    Other Members:

| | |
|---|---|
| Blueberry red ringspot (327) | Carnation etched ring (182) |
| Dahlia mosaic (51) | Figwort mosaic |
| Horseradish latent | Mirabilis mosaic |
| Peanut chlorotic streak | Soybean chlorotic mottle (331) |
| Strawberry vein banding (219) | Thistle mottle |

Putative Members:

| | |
|---|---|
| Aquilegia necrotic mosaic | Cassava vein mosaic |
| Cestrum virus | Petunia vein clearing |
| Plantago virus 4 | Sonchus mottle |

VI. GROUP     GEMINIVIRUS
Subgroup I (i.e., Genus)
    Maize streak virus
    Preferred Member:
        Maize streak virus (MSV) (133)
    Other Members:
        Chloris striate mosaic (221)
        Digitaria streak
        Miscanthus streak
        Wheat dwarf
    Putative Members:
        Bajra streak
        Bromus striate mosaic
        Digitaria striate mosaic
        Oat chlorotic stripe
        Paspalum striate mosaic
Subgroup II (i.e., Genus):
    Beet curly top virus
    Preferred Member:
        Beet curly top virus (BCTV) (210)
    Other Members:
        Tomato pseudo-curly top virus
        Bean summer death virus
        Tobacco yellow dwarf virus
        Tomato leafroll virus
Subgroup III (i.e., Genus):
    Bean golden mosaic virus
    Preferred Member:
        Bean golden mosaic virus (BGMV) (192)
    Other Members:

| | |
|---|---|
| Abutilon mosaic virus | African cassava mosaic virus |
| Cotton leaf crumple virus | Euphorbia mosaic virus |
| Horsegram yellow mosaic virus | Indian cassava mosaic virus |
| Jatropha mosaic virus | Limabean golden mosaic virus |
| Malvaceous chlorosis virus | Melon leaf curl virus |
| Mungbean yellow mosaic virus | Potato yellow mosaic virus |
| Rhynochosia mosaic virus | Squash leaf curl virus |
| Tigre disease virus | Tobacco leaf curl virus |
| Tomato golden mosaic virus | Tomato leaf curl virus |
| Tomato yellow dwarf virus | Tomato yellow leaf curl virus |
| Tomato yellow mosaic virus | Watermelon curly mottle virus |
| Watermelon chlorotic stunt virus | |
| Honeysuckle yellow vein mosaic virus | |

Putative Members:

| | |
|---|---|
| Cotton leaf curl virus | Cowpea golden mosaic virus |
| Eggplant yellow mosaic virus | Eupatorium yellow vein virus |
| Lupin leaf curl virus | Soyabean crinkle leaf virus |
| Solanum apical leaf curl virus | Wissadula mosaic virus |

VII. FAMILY: DSDNA ALGAL VIRUSES     PHYCODNAVIRIDAE
    Genus:
        dsdna Phycovirus Phycodnavirus group
        Preferred Species:
            *Paramecium bursaria* chlorella virus - 1 (PBCV - 1)
        Viruses of:
            *Paramecium bursaria* Chlorella NC64A viruses (NC64A viruses)

TABLE 1-continued

NON-MAMMALIAN DNA VIRUSES THAT CAN BE USED IN THE INVENTION.[1]

*Paramecium bursaria* Chlorella Pbi viruses (Pbi viruses)
Hydra virdis Chlorella viruses (HVCV)
Other Members:
Chlorella NC64A viruses (thirty-seven NC64A viruses,
including PBCV-1)
Chlorella virus NE-8D (CV-NE8D; synonym NE-8D)

| | | |
|---|---|---|
| CV-NYb1 | CV-CA4B | CV-AL1A |
| CV-NY2C | CV-NC1D | CV-NC1C |
| CV-CA1A | CV-CA2A | CV-IL2A |
| CV-IL2B | CV-JL3A | CV-IL3D |
| CV-SC1A | CV-SC1B | CV-NC1A |
| CV-NE8A | CV-AL2C | CV-MA1E |
| CV-NY2F | CV-CA1D | CV-NC1B |
| CV-NYs1 | CV-1L5-2s1 | CV-AL2A |
| CV-MA1D | CV-NY2B | CV-CA4A |
| CV-NY2A | CV-XZ3A | CV-SH6A |
| CV-BJ2C | CV-XZ6E | CV-XZ4C |
| CV-XZ5C | CV-XZ4A | |

Chlorella Pbi viruses
| | | |
|---|---|---|
| CVA-1 | CVB-1 | CVG-1 |
| CVM-1 | CVR-1 | |

Hydra viridis Chlorella viruses
   HVCV-1
   HVCV-2
   HVCV-3

VIII. FAMILY: POLYDNAVIRUS GROUP      POLYDNAVIRIDAE
Genus:
   Ichnovirus
   Preferred Species:
      *Campoletis sonorensis* virus (CsV)
   Other Member:
      Viruses of Glypta sp.
Genus:
   Bracovirus
   Preferred Species:
      *Cotesia melanoscela* virus (CmV)

[1]These viruses are listed In: "Fifth Report of the International Committee on Taxonomy of Viruses" (ICTV) by Cornelia Buchen-Osmond, 1991, Research School of Biological Sciences, Canberra, Australia. Most viruses listed here are available from the American Type Culture Collection.

The genome of the non-mammalian DNA virus can be engineered to include one or more genetic elements, such as a promoter of a long-terminal repeat of a transposable element or a retrovirus (e.g., Rous Sarcoma Virus); an inverted terminal repeat of an adeno-associated virus and an adeno-associated rep gene; and/or a cell-immortalizing sequence, such as the SV40 T antigen or c-myc. If desired, the genome of the non-mammalian DNA virus can include an origin of replication that functions in a mammalian cell (e.g., an Epstein Barr Virus (EBV) origin of replication or a mammalian origin of replication). Examples of mammalian origins of replication include sequences near the dihydrofolate reductase gene (Burhans et al., 1990, Cell 62:955–965), the β-globin gene (Kitsberg et al., 1993, Cell 366:588–590), the adenosine deaminase gene (Carroll et al., 1993, Mol. Cell. Biol. 13:2927–2981), and other human sequences (see Krysan et al., 1989, Mol. Cell. Biol. 9:1026–1033). If desired, the origin of replication can be used in conjunction with a factor that promotes replication of autonomous elements, such as the EBNA1 gene from EBV. The genome of the non-mammalian DNA virus can include a polyadenylation signal and a mammalian RNA splicing signal (i.e., one that functions in mammalian cells) positioned for proper processing of the product of the exogenous gene. In addition, the virus may be engineered to encode a signal sequence for proper targeting of the gene product.

Where cell-type specific expression of the exogenous gene is desired, the genome of the virus can include a cell-type-specific promoter, such as a promoter that is specific for liver cells, brain cells (e.g., neuronal cells), glial cells, Schwann cells, lung cells, kidney cells, spleen cells, muscle cells, or skin cells. For example, a liver cell-specific promoter can include a promoter of a gene encoding albumin, α-1-antitrypsin, pyruvate kinase, phosphenol pyruvate carboxykinase, transferrin, transthyretin, α-fetoprotein, α-fibrinogen, or β-fibrinogen. Alternatively, a hepatitis A, B, or C viral promoter can be used. If desired, a hepatitis B viral enhancer may be used in conjunction with a hepatitis B viral promoter. Preferably, an albumin promoter is used. An α-fetoprotein promoter is particularly useful for driving expression of an exogenous gene when the invention is used to express a gene for treating a hepatocellular carcinoma. Other preferred liver-specific promoters include promoters of the genes encoding the low density lipoprotein receptor, α2-macroglobulin, α1-antichymotrypsin, α2-HS glycoprotein, haptoglobin, ceruloplasmin, plasminogen, complement proteins (C1q, C1r, C2, C3, C4, C5, C6, C8, C9, complement Factor I and Factor H), C3 complement activator, β-lipoprotein, and α1-acid glycoprotein. For expression of an exogenous gene specifically in neuronal cells, a neuron-specific enolase promoter can be used (see Forss-Petter et al., 1990, Neuron 5: 187–197). For expression of an exogenous gene in dopaminergic neurons, a tyrosine hydroxylase promoter can be used. For expression in pituitary cells, a pituitary-specific promoter such as POMC may be useful (Hammer et al., 1990, Mol. Endocrinol. 4:1689–97).

Promoters that are inducible by external stimuli also can be used. Such promoters provide a convenient means for controlling expression of the exogenous gene in a cell of a cell culture or mammal. Preferred inducible promoters include enkephalin promoters (e.g., the human enkephalin promoter), metallothionein promoters, and mouse mammary tumor virus promoters. Methods for inducing gene expression from each of these promoters are known in the art.

Essentially any mammalian cell can be used in the ethods of the invention; preferably, the mammalian cell is a human cell. The cell can be a primary cell (e.g., a primary hepatocyte, primary neuronal cell, or primary myoblast) or it may be a cell of an established cell line. It is not necessary that the cell be capable of undergoing cell division; a terminally differentiated cell can be used. If desired, the virus can be introduced into a primary cell approximately 22–26 hours (e.g., approximately 24 hours) after the initial plating of the primary cell to optimize the efficiency of infection. Preferably, the mammalian cell is a liver-derived cell, such as a HepG2 cell, a Hep3B cell, a Huh-7 cell, an FTO2B cell, a Hepa1-6 cell, or an SK-Hep-1 cell) or a Kupffer cell; a kidney cell, such as a cell of the kidney cell line 293, a PC12 cell (e.g., a differentiated PC12 cell induced by nerve growth factor), a COS cell (e.g., a COS7 cell), or a Vero cell; a neuronal cell, such as a fetal neuronal cell, cortical pyramidal cell, mitral cell, a granule cell, or a brain cell (e.g., a cell of the cerebral cortex; an astrocyte; a glial cell; a Schwann cell); a muscle cell, such as a myoblast or myotube (e.g., a $C_2C_{12}$ cell); a spleen cell (e.g., a macrophage or lymphocyte); an epithelial cell, such as a HeLa cell; a fibroblast, such as an NIH3T3 cell; an endothelial cell; or a bone marrow stem cell. Other preferred mammalian cells include CHO/dhfr$^-$ cells, Ramos, Jurkat, HL60, and K-562 cells.

The virus can be introduced into a cell in vitro or in vivo. Where the virus is introduced into a cell in vitro, the infected cell can subsequently be introduced into a mammal, if desired. Accordingly, expression of the exogenous gene can be accomplished by maintaining the cell in vitro, in vivo, or in vitro and in vivo, sequentially. Similarly, where the invention is used to express an exogenous gene in more than one cell, a combination of in vitro and in vivo methods may be used to introduce the gene into more than one mammalian cell.

If desired, the virus can be introduced into the cell by administering the virus to a mammal that carries the cell. For example, the virus can be administered to a mammal by subcutaneous, intravascular, or intraperitoneal injection. If desired, a slow-release device, such as an implantable pump, may be used to facilitate delivery of the virus to cells of the mammal. A particular cell type within a mammal can be targeted by modulating the amount of the virus administered to the mammal and by controlling the method of delivery. For example, intravascular administration of the virus to the portal, splenic, or mesenteric veins or to the hepatic artery may be used to facilitate targeting the virus to liver cells. In another method, the virus may be administered to cells or organ of a donor individual (human or non-human) prior to transplantation of the cells or organ to a recipient.

In a preferred method of administration, the virus is administered to a tissue or organ containing the targeted cells of the mammal. Such administration can be accomplished by injecting a solution containing the virus into a tissue, such as skin, brain (e.g., the olfactory bulb), kidney, bladder, trachea, liver, spleen, muscle, thyroid, thymus, lung, or colon tissue. Alternatively, or in addition, administration can be accomplished by perfusing an organ with a solution containing the virus, according to conventional perfusion protocols.

In another preferred method, the virus is administered intranasally, e.g., by applying a solution of the virus to the nasal mucosa of a mammal. This method of administration can be used to facilitate retrograde transportation of the virus into the brain. This method thus provides a means for delivering the virus to brain cells, (e.g., mitral and granule neuronal cells of the olfactory bulb) without subjecting the mammal to surgery.

In an alternative method for using the virus to express an exogenous gene in the brain, the virus is delivered to the brain by osmotic shock according to conventional methods for inducing osmotic shock.

Where the cell is maintained under in vitro conditions, conventional tissue culture conditions and methods may be used. In a preferred method, the cell is maintained on a substrate that contains collagen, such as Type I collagen or rat tail collagen, or a matrix containing laminin. As an alternative to, or in addition to, maintaining the cell under in vitro conditions, the cell can be allowed to live under in vivo conditions (e.g., in a human). Implantable versions of collagen substrates are also suitable for maintaining the virus-infected cells under in vivo conditions in practicing the invention (see, e.g., Hubbell et al., 1995, Bio/Technology 13:565–576 and Langer and Vacanti, 1993, Science 260: 920–925).

The invention can be used to express a variety of exogenous genes encoding gene products such as a polypeptides or proteins, antisense RNAs, and catalytic RNAs. If desired, the gene product (e.g., protein or RNA) can be purified from the mammalian cell. Thus, the invention can be used in the manufacture of a wide variety of proteins that are useful in the fields of biology and medicine.

An "antisense" nucleic acid is a nucleic acid molecule (i.e., DNA or RNA) that is complementary (i.e., able to hybridize in vivo or under stringent in vitro conditions) to all or a portion of a nucleic acid (e.g., a gene or mRNA) that encodes a polypeptide of interest. If desired, conventional methods can be used to produce an antisense nucleic acid that is contains desirable modifications. For example, a phosphorothioate oligonucleotide can be used as the antisense nucleic acid in order to inhibit degradation of the antisense oligonucleotide by nucleases in vivo. Where the antisense nucleic acid is complementary to a portion of the nucleic acid encoding the polypeptide of interest, the antisense nucleic acid should hybridize close enough to the 5' end of the nucleic acid such that it inhibits translation of a functional polypeptide (i.e., a polypeptide that carries out an activity that one wishes to inhibit (e.g., an enzymatic activity)). Typically, this means that the antisense nucleic acid should be complementary to a sequence that is within the 5' half or third of the gene to which it hybridizes. As used herein, an "antisense gene" is a nucleic acid that encodes an antisense nucleic acid. Typically, such an antisense gene includes all or a portion of the gene the expression of which is to be inhibited, but the antisense gene is operably linked to a promoter such that the antisense gene is in the opposite orientation, relative to the orientation of the gene that is to be inhibited.

Where the invention is used to express an antisense RNA, the preferred antisense RNA is complementary to a nucleic acid (e.g., an mRNA) of a pathogen of the mammalian cell (e.g., a virus, a bacterium, or a fungus). For example, the invention can be used in a method of treating a hepatitis viral infection by expressing an antisense RNA that hybridizes to an mRNA of an essential hepatitis virus gene product (e.g., a polymerase mRNA). Other preferred gene product (e.g., a polymerase mRNA). Other preferred antisense RNAs include those that are complementary to a naturally-occurring gene in the cell, which gene is expressed at an undesirably high level. For example, an antisense RNA can be designed to inhibit expression of an oncogene in a mammalian cell. Similarly, the virus can be used to express a catalytic RNA (i.e., a ribozyme) that inhibits expression of a target gene in the cell by hydrolyzing an mRNA encoding the targeted gene product. Antisense RNAs and catalytic RNAs can be designed by employing conventional criteria.

If desired, the invention can be used to express a dominant negative mutant in a mammalian cell. For example, viral assembly in a cell can be inhibited or prevented by expressing in that cell a dominant negative mutant of a viral capsid protein (see, e.g., Scaglioni et al., 1994, Virology 205:112–120; Scaglioni et al., 1996, Hepatology 24:1010–1017; and Scaglioni et al., 1997, J. Virol. 71:345–353).

The invention can be used to express any of various "therapeutic" genes in a cell. A "therapeutic" gene is one that, when expressed, confers a beneficial effect on the cell or tissue in which it is present, or on a mammal in which the gene is expressed. Examples of "beneficial effects" include amelioration of a sign or symptom of a condition or disease, prevention or inhibition of a condition or disease, or conferral of a desirable characteristic, including even temporary amelioration of signs or symptoms of a disorder. Included among the therapeutic genes are those genes that correct a gene deficiency disorder in a cell or mammal ("correction of a disorder need not be equivalent to curing a patient suffering from a disorder). For example, carbamoyl synthetase I can correct a gene deficiency disorder when it is expressed in a cell that previously failed to express, or expressed insufficient levels of, carbamoyl synthetase I. Also included are genes that are expressed in one cell, yet which confer a beneficial effect on a second cell. For example, a gene encoding insulin can be expressed in a pancreatic cell from which the insulin is then secreted to exert a beneficial effect on other cells of the mammal. Other therapeutic genes include sequences that are transcribed into antisense RNAs that inhibit transcription or translation of a gene that is expressed at an undesirably high levels. Also included are antisense genes that encode a nucleic acid that inhibits expression of a gene that is expressed at an undesirable level. For example, an antisense gene that inhibits expression of a gene encoding an oncogenic protein is considered a therapeutic gene. "Cancer therapeutic" genes are those genes that confer a beneficial effect on a cancerous cell or a mammal suffering from cancer. Particularly useful cancer therapeutic genes include the p53 gene, a herpes simplex virus thymidine kinase gene, and an antisense gene that is complementary to an oncogene.

The invention can be used to express a therapeutic gene in order to treat a disorder (e.g., a gene deficiency disorder). Particularly appropriate genes for expression include those genes that thought to be expressed at a less than normal level in the target cells of the subject mammal. Particularly useful gene products include carbamoyl synthetase I, ornithine transcarbamylase, arginosuccinate synthetase, arginosuccinate lyase, and arginase. Other desirable gene products include fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase (also referred to as P-protein), H-protein, T-protein, Menkes disease copper-transporting ATPase, and Wilson's disease copper-transporting ATPase. Other examples of desirable genes for expression with the invention include genes encoding tumor suppressors (e.g., p53), insulin, or CFTR (e.g., for treating cystic fibrosis).

The invention can also be used to express in a mammalian cell a gene that is expected to have a biological effect in mammals but not in insects (i.e., a "mammal-specific" gene). For example, a baculovirus genome can be used to express a mammalian myoD gene and thereby produce muscle proteins; such a gene would be expected to have a biological effect in mammalian cells but not insect cells. Other examples of mammal-specific genes include, but are not limited to, transcription factors that function in mammalian, but not insect, cells. For example, the transcription factors c/ebp-alpha and chop10 will activate liver cell differentiation pathways when expressed from an insect genome (e.g., a baculovirus genome) in a mammalian cell. In contrast, expression of these mammal-specific transcription factors in an insect cell would be expected to have a minimal, or no, effect on the insect cell.

If desired, the vectors of the invention can be used to propagate genetic constructs in non-mammalian (e.g., insect) cells, with the advantage of inhibiting DNA methylation of the product. It has been observed that a promoter may become methylated in cell lines or tissues in which it is not normally expressed, and that such methylation is inhibitory to proper tissue specific expression (Okuse et al., 1997, Brain Res. Mol. Brain Res. 46:197–207; Kudo et al., 1995, J. Biol. Chem. 270:13298–13302). For example, a neural promoter may become methylated in a non-neural mammalian cell. By using, for example, insect cells (e.g., Sf9 cells) to propagate a baculovirus carrying an exogenous gene and a mammalian promoter (e.g., a neural promoter), the invention provides a means for inhibiting DNA methylation of the promoter prior to administration of the baculovirus and exogenous gene to the mammalian cell in which the exogenous gene will be expressed (e.g., a neural cell).

Definitions

By "non-mammalian" DNA virus is meant a virus that has a DNA genome (rather than RNA) and which is naturally incapable of replicating in a vertebrate, and specifically a mammalian, cell. Included are insect viruses (e.g., baculoviruses), amphibian viruses, plant viruses, and fungal viruses. Viruses that naturally replicate in prokaryotes are excluded. Examples of viruses that are useful in practicing the invention are listed in Table 1. As used herein, a "genome" can include all or some of the nucleic acid sequences present in a naturally-occurring non-mammalian DNA virus. If desired, genes or sequences can be removed from the virus genome or disabled (e.g., by mutagenesis), provided that the retains, or is engineered to retain, its ability to express an exogenous gene in a mammalian cell. For example, the virus can be engineered such that it lacks a functional polyhedrin gene. Such a virus can be produced by deleting all or a portion of the polyhedrin gene from a virus genome (e.g., a baculovirus genome) or by introducing mutations (e.g., a frameshift mutation) into the polyhedrin gene so that the activity of the gene product is inhibited.

By "insect" DNA virus is meant a virus that has a DNA genome and which is naturally capable of replicating in an insect cell (e.g., Baculoviridae, Iridoviridae, Poxviridae, Polydnaviridae, Densoviridae, Caulimoviridae, and Phycodnaviridae).

By "positioned for expression" is meant that the DNA sequence that includes the reference gene (e.g., the exogenous gene) is positioned adjacent to a DNA sequence that directs transcription of the DNA and, if desired, translation of the RNA (i.e., facilitates the production of the desired gene product).

By "promoter" is meant at least a minimal sequence sufficient to direct transcription. A "mammalian-active" promoter is one that is capable of directing transcription in a mammalian cell. The term "mammalian-active" promoter includes promoters that are derived from the genome of a mammal, i.e., "mammalian promoters," and promoters of viruses that are naturally capable of directing transcription in mammals (e.g., an MMTV promoter or a hepatitis viral promoter). Other promoters that are useful in the invention include those promoters that are sufficient to render promoter-dependent gene expression controllable for cell-type specificity, cell-stage specificity, or tissue-specificity (e.g., liver-specific promoters), and those promoters that are "inducible" by external signals or agents (e.g., metallothionein, MMTV, and pENK promoters); such elements can be located in the 5' or 3' regions of the native gene. The promoter sequence can be one that does not occur in nature, so long as it functions in a mammalian cell. An "inducible" promoter is a promoter that, (a) in the absence of an inducer, does not direct expression, or directs low levels of expression, of a gene to which the inducible promoter is operably linked; or (b) exhibits a low level of expression in the presence of a regulating factor that, when removed, allows high-level expression from the promoter (e.g., the tet system). In the presence of an inducer, an inducible promoter directs transcription at an increased level.

By "operably linked" is meant that a gene and a regulatory sequence(s) (e.g., a promoter) are connected in such a way as to permit gene expression when the appropriate molecules (e.g., transcriptional activator proteins) are bound to the regulatory sequence(s).

By "cell-immortalizing sequence" is meant a nucleic acid that, when present in a mammalian cell, is capable of transforming the cell for prolonged inhibition of senescence. Included are SV40 T-antigen, c-myc, telomerase, and E1A.

By "antisense" nucleic acid is meant a nucleic acid molecule (i.e., RNA) that is complementary (i.e., able to hybridize in vivo or under stringent in vitro conditions) to all or a portion of a target nucleic acid (e.g., a gene or mRNA) that encodes a polypeptide of interest. If desired, conventional methods can be used to produce an antisense nucleic acid that contains desirable modifications. For example, a phosphorothioate oligonucleotide can be used as the antisense nucleic acid in order to inhibit degradation of the antisense oligonucleotide by nucleases in vivo. Where the antisense nucleic acid is complementary to only a portion of the target nucleic acid encoding the polypeptide to be inhibited, the antisense nucleic acid should hybridize close enough to some critical portion of the target nucleic acid (e.g., in the translation control region of the non-coding sequence, or at the 5' end of the coding sequence) such that it inhibits translation of a functional polypeptide (i.e., a polypeptide that carries out an activity that one wishes to inhibit (e.g., an enzymatic activity)). Typically, this means that the antisense nucleic acid should be complementary to a sequence that is within the 5' half or third of a target mRNA to which the antisense nucleic acid hybridizes. As used herein, an "antisense gene" is a nucleic acid that is transcribed into an antisense RNA. Typically, such an antisense gene includes all or a portion of the target nucleic acid, but the antisense gene is operably linked to a promoter such that the orientation of the antisense gene is opposite to the orientation of the sequence in the naturally-occurring gene.

Use

The invention is useful for expressing an exogenous gene(s) in a mammalian cell in vitro or in vivo (e.g., a HepG2 cell). This method can be employed in the manufacture of proteins to be purified, such as proteins that are administered as pharmaceutically agents (e.g., insulin). The virus of the invention can also be used therapeutically. For example, the invention can be used to express in a patient a gene encoding a protein that corrects a deficiency in gene expression. In alternative methods of therapy, the invention can be used to express any protein, antisense RNA, or catalytic RNA in a cell.

The non-mammalian viral expression system of the invention offers several advantages. The invention allows for de novo expression of an exogenous gene; thus, detection of the exogenous protein (e.g., β-galactosidase) in an infected cell represents protein that was actually synthesized in the infected cell, as opposed to protein that is carried along with the virus aberrantly. The non-mammalian viruses used in accordance with the invention are not normally pathogenic to humans; thus, concerns about safe handling of these viruses are minimized. Similarly, because the majority of naturally-occurring viral promoters are not normally active in a mammalian cell, production of undesired viral proteins is minimized. While traditional gene therapy vectors are based upon defective viruses that are propagated with helper virus or on a packaging line, the invention employs a virus that is not defective for growth on insect cells for purposes of propagation, but is intrinsically, and desirably, defective for growth on mammalian cells. Accordingly, in contrast to some mammalian virus-based gene therapy methods, the non-mammalian virus-based methods of the invention should not provoke a host immune response to the viral proteins.

The non-mammalian virus used in accordance with the invention can be propagated with cells grown in serum-free media, eliminating the risk of adventitious infectious agents occasionally present in the serum contaminating a virus preparation. In addition, the use of serum-free media eliminates a significant expense faced by users of mammalian viruses. Certain non-mammalian viruses, such as baculoviruses, can be grown to a high titer (i.e., $10^8$ pfu/ml). Generally, the large virus genomes that can be used (e.g., the baculovirus genome at 130 kbp) can accept large exogenous DNA molecules (e.g., 100 kb). In certain embodiments, the invention employs a virus whose genome has been engineered to contain an exogenous origin of replication (e.g., the EBV oriP). The presence of such sequences on the virus genome allows episomal replication of the virus, increasing persistence in the cell. Where the invention is used in the manufacture of proteins to be purified from the cell, the invention offers the advantage that it employs a mammalian expression system. Accordingly, one can expect proper post-translational processing and modification (e.g., glycosylation) of the gene product.

Other features and advantages of the invention will be apparent from the following detailed description, and from the claims.

BRIEF DESCRIPTION OF THE DRAWINGS

FIGS. 14A–D are photographs of cells that were stained with X-gal one day post-infection with an AcMNPV virus containing a RSV-lacZ cassette. Cells expressing the lacZ gene stain darkly with X-gal. FIG. 14A is a photograph of a typical field of HepG2 cells infected at a multiplicity of infection of 15. FIG. 14B is a photograph of a typical field of HepG2 cells infected at a multiplicity of infection of 125; over 25% of the cells were stained. FIG. 14C is a typical field of Sk-Hep-1 cells infected at a multiplicity of infection of 125, showing no positively-stained cells. FIG. 14D is a less typical field of Sk-Hep-1 cells infected at a multiplicity of infection of 125 showing a positively-stained cell. Bar=55 μm.

FIG. 15 is a photograph of cells obtained following baculovirus-mediated gene transfer into primary cultures of rat hepatocytes. Over 70% of the cells were stained blue.

DETAILED DESCRIPTION

I. Genetic Manipulation of Viruses

Figure 1:
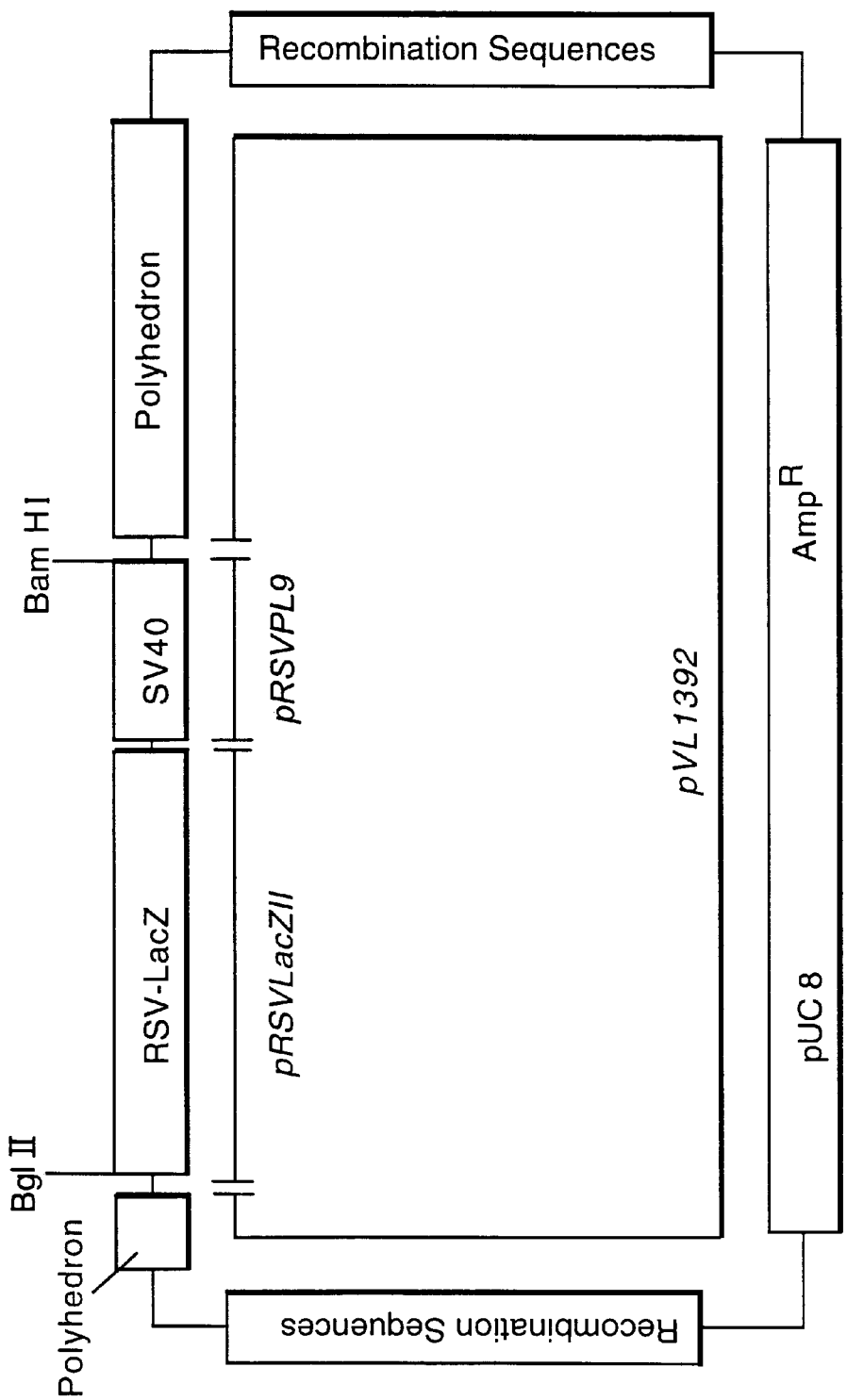
FIG. 1 is a schematic representation of the AcMNPV RSV-lacZ transfer plasmid pZ4.

In contrast to conventional gene expression methods, the invention involves modifying non-mammalian DNA viruses that do not naturally infect and replicate in mammalian cells. Thus, the invention is based on the addition of new properties to a non-mammalian DNA virus that allow it to deliver a gene to a mammalian cell and allow for expression of the gene within the cell. In contrast, conventional gene therapy vectors are require that one disable viral functions, such as expression of viral genes and viral genome replication.

In the present method, the viral particle serves as a "shell" for the delivery of DNA to the mammalian cell. The viral DNA is engineered to contain transcriptional control sequences that are active in a mammalian cell, to allow expression of the gene of interest in the target cell. Conventional recombinant DNA techniques can be used for inserting such sequences. Because the non-mammalian DNA viruses used in accordance with the invention are not capable of replicating in mammalian cells, it is not necessary to delete essential viral functions to render them defective. Preferably, the genome of the virus is normally transported to the nucleus in its natural host species because nuclear localization signals function similarly in invertebrate and in mammalian cells.

Preferably, the viral capsid or envelope contains a ligand that binds to mammalian cells to facilitate entry. Viruses propagated in invertebrate species (e.g., insects, plants, or fungi) do not normally terminate glycoproteins with sialic acid, and thus the viral ligand is often an asialoglycoprotein that binds to mammalian lectins (e.g., the hepatic asialoglycoprotein receptor), facilitating entry into mammalian cells.

In addition, it is preferred that the virus naturally replicate in a eukaryotic species. Examples of viruses that can be engineered to express exogenous gene in accordance with the invention are listed in Table 1.

Established methods for manipulating recombinant viruses may be incorporated into these new methods for expressing an exogenous gene in a mammalian cell. For example, viral genes can be deleted from the virus and supplied in trans via packaging lines. Deletion of such genes may be desired in order to (1) suppress expression of viral gene products that may provoke an immune response, (2) provide additional space in the viral vector, or (3) provide additional levels of safety in maintaining the virus in a cell.

Because most promoters of non-mammalian viruses are not active in mammalian cells, the exogenous gene should be operably linked to a promoter that is capable of directing gene expression in a mammalian cell. Examples of suitable promoters include the RSV LTR, the SV40 early promoter, CMV IE promoters (e.g., the human CMV IE1 promoter), the adenovirus major late promoter, and the Hepatitis B viral promoter. In addition, promoters that are cell-type-specific, stage-specific, or tissue-specific can be used. For example, several liver-specific promoters, such as the albumin promoter/enhancer, have been described (see, e.g., Shen et al., 1989, DNA 8:101–108; Tan et al., 1991, Dev. Biol. 146:24–37; McGrane et al., 1992, TIBS 17:40–44; Jones et al., J. Biol. Chem. 265:14684–14690; and Shimada et al., 1991, FEBS Letters 279:198–200). Where the invention is used to treat a hepatocellular carcinoma, an α-fetoprotein promoter is particularly useful. This promoter is normally active only in fetal tissue; however, it is also active in liver tumor cells (Huber et al., 1991, Proc. Natl. Acad. Sci. 88:8039–8043). Accordingly, an α-fetoprotein promoter can be used to target expression of a liver-cancer therapeutic to liver tumor cells.

If desired, the virus genome can be engineered to carry an origin of replication in order to facilitate persistence of the exogenous gene in the mammalian cell. Origins of replication derived from mammalian cells (i.e., "mammalian origins of replication") have been identified (Burhans et al., 1994, Science 263:639–640). Other origins of replication, such as the Epstein-Barr Virus oriP, can also facilitate maintenance of expression in the presence of appropriate trans-acting factors, such as EBNA-1. If desired, the virus genome can be engineered to express more than one exogenous gene (e.g., the virus can be engineered to express both OTC and AS).

Descriptions of several viruses that can be used in the invention now follow. These examples are provided for illustrative purposes, and are not meant to limit the scope of invention.

II. Examples of Transfer Plasmids

Construction of the pZ4 Transfer Plasmid: Genetic manipulation of a baculovirus for use in the invention can be accomplished with commonly-known recombination techniques originally developed for expressing proteins in baculovirus (see, e.g., O'Reilly et al., 1992, In: Baculovirus expression vectors, W. H. Freeman, New York). In this example, an AcMNPV was constructed by interrupting the polyhedrin gene of the virus with a cassette that directs expression of a reporter gene. The reporter gene cassette included DNA sequences corresponding to the Rous Sarcoma Virus (RSV) promoter operably linked to the E. coli lacZ gene (FIG. 1). The reporter gene cassette also included sequences encoding Simian Virus 40 (SV40) RNA splicing and polyadenylation signals.

The RSV-lacZ AcMNPV transfer plasmid used in several examples set forth below is named pZ4 and was constructed as follows. An 847 bp fragment of pRSVPL9 including the SV40 RNA splicing signal and polyadenylation signal was excised using BglII and BamHI. Plasmid pRSVPL9 was derived from pRSVglobin (Gorman et al., Science 221:551–553) by digesting pRSVglobin with BglII, adding a HindIII linker, and then cleaving the DNA with HindIII. A double-stranded polylinker made by hybridization of the oligonucleotides 5'AGCTGTCGACTCGAGGTACCA-GATCTCTAGA3' (SEQ ID NO: 1) and 5'AGCTTCTA-GAGATCTGGTACCTCGAGTCGAC3' (SEQ ID NO: 2) was ligated to the 4240 bp fragment having the RSV promoter and SV40 splicing and polyadenylation signals. The resulting plasmid has the polylinker in place of the globin sequences. The SV40 sequence of pRSVPL9 was cloned into the BamHI site of pVL1392 (Invitrogen and Pharmingen) using standard techniques. The resulting intermediate plasmid was named pVL/SV40. An RSV-lacZ cassette was excised from pRSVlacZII (Lin et al., 1991, Biotechniques 11:344–348, and 350–351) with BglII and SpeI and inserted into the BglII and XbaI sites of pVL/SV40.

The AcMNPV RSV-lacZ virus, termed Z4, was prepared by homologous recombination of the Z4 transfer plasmid with linearized AcMNPV DNA. The AcMNPV virus used to prepare this DNA was AcV-EPA (Hartig et al., 1992, J. Virol. Methods 38:61–70).

Figure 2:
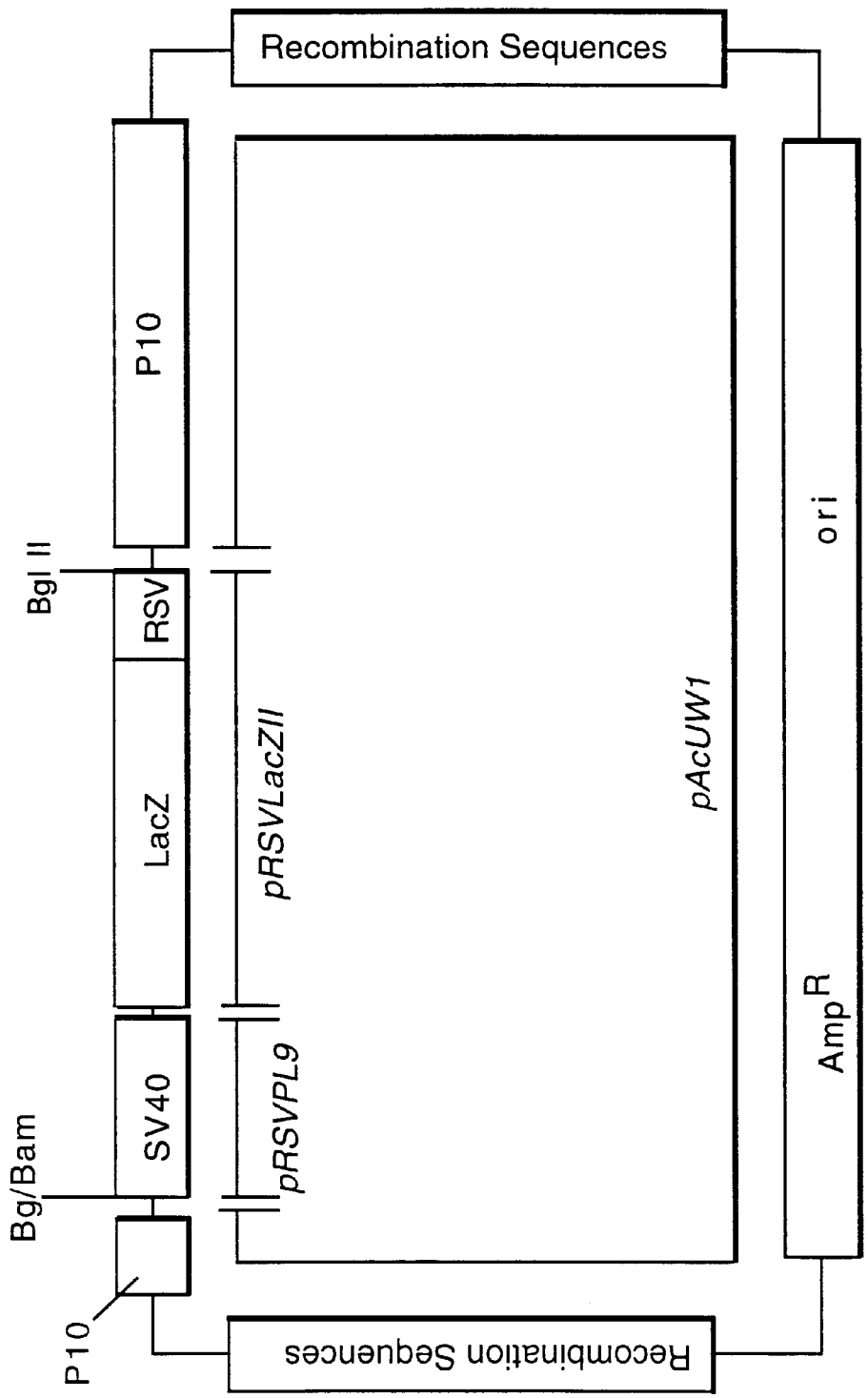
FIG. 2 is a schematic representation of the occluded AcMNPV RSV-lacZ transfer plasmid pZ5.

Construction of the pZ5 Transfer Plasmid: Certain non-mammalian viruses (e.g., baculoviruses) may be occluded in a protein inclusion body, or they may exist in a plasma membrane budded form. Where an occluded virus is used in the invention, the virus may first be liberated from the protein inclusion body, if desired. Conventional methods employing alkali may be used to release the virus (O'Reilly et al., 1992, In: Baculovirus expression vectors, W. H. Freeman, New York). An occluded, alkali-liberated baculovirus may be taken up by a cell more readily than is the non-occluded budded virus (Volkman and Goldsmith, 1983, Appl. and Environ. Microbiol. 45:1085–1093). To construct the Z5 transfer plasmid (FIG. 2), for using an occluded virus in the invention, the RSV-lacZ cassette was excised from the pZ4 transfer plasmid using BglII and BamHI and then inserted into the BglII site of pAcUW1 (Weyer et al., 1990, J. Gen. Virol. 71:1525–1534).

Figure 3:
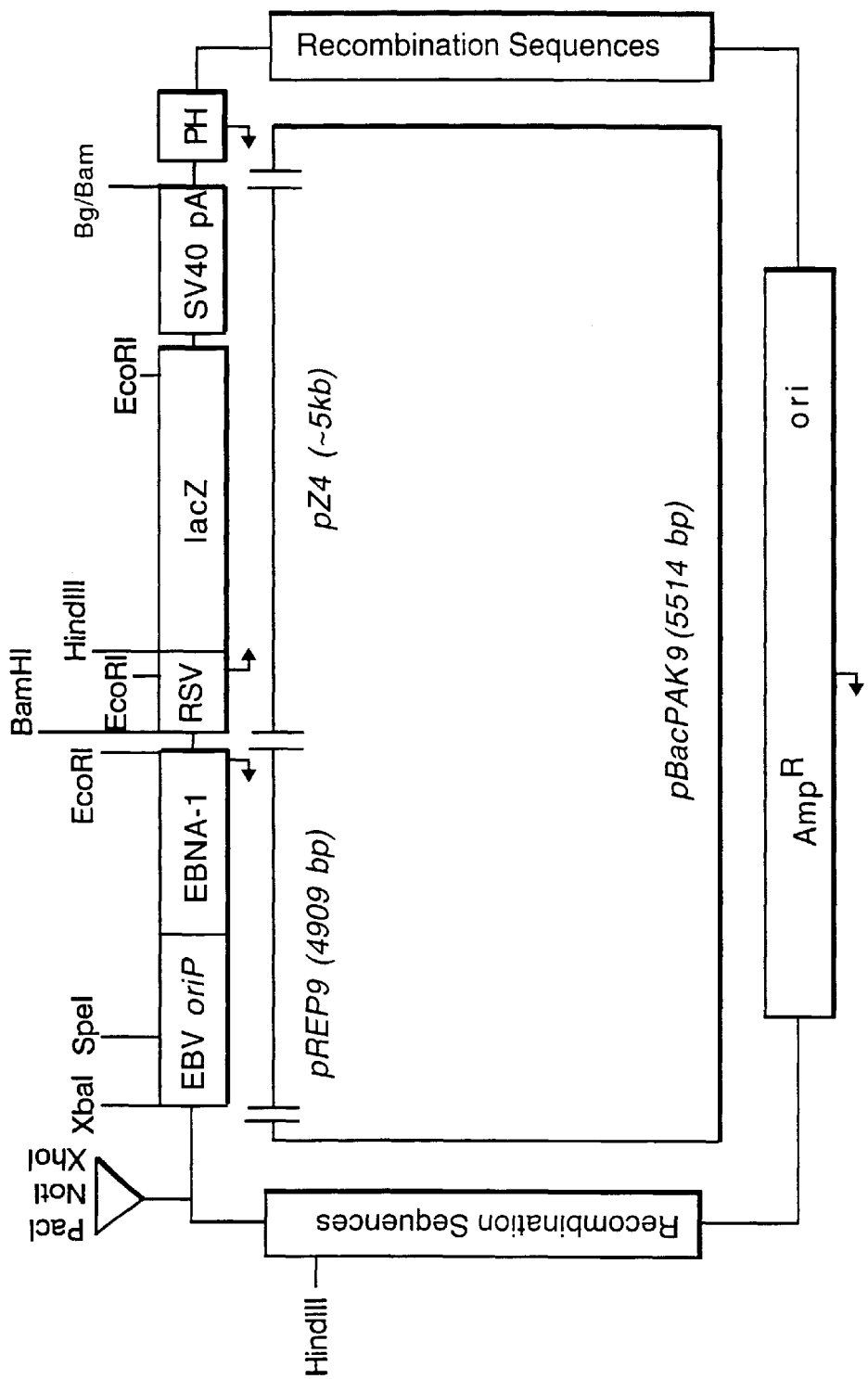
FIG. 3 is a schematic representation of the episomal transfer plasmid pZ-EBV#1, a chimera of baculovirus and Epstein Barr Virus sequences. A virus produced with this transfer plasmid is capable of replicating in a mammalian cell.

Construction of the pZ-EBV#1 Transfer Plasmid: The non-mammalian DNA viruses used in the invention may be engineered to permit episomal replication of the virus in the mammalian cell. Such a virus would persist longer, thereby optimizing methods for long-term expression of an exogenous gene in a cell. An example of such a replicating virus is Z-EBV#1 (FIG. 3), which was constructed as follows. The EBV oriP and EBNA-1 region was excised from pREP9 (Invitrogen) using EcoRI and XbaI and then inserted into the baculoviral transfer plasmid pBacPAK9 (Clontech) at its EcoRI and XbaI sites, yielding pEBVBP9. The RSV-lacZ cassette was excised from transfer plasmid pZ4 with BglII and BamHI and then inserted into the BamHI site of pEBVBP9 to yield the plasmid pZ-EBV#1.

Figures 4A, 4B:
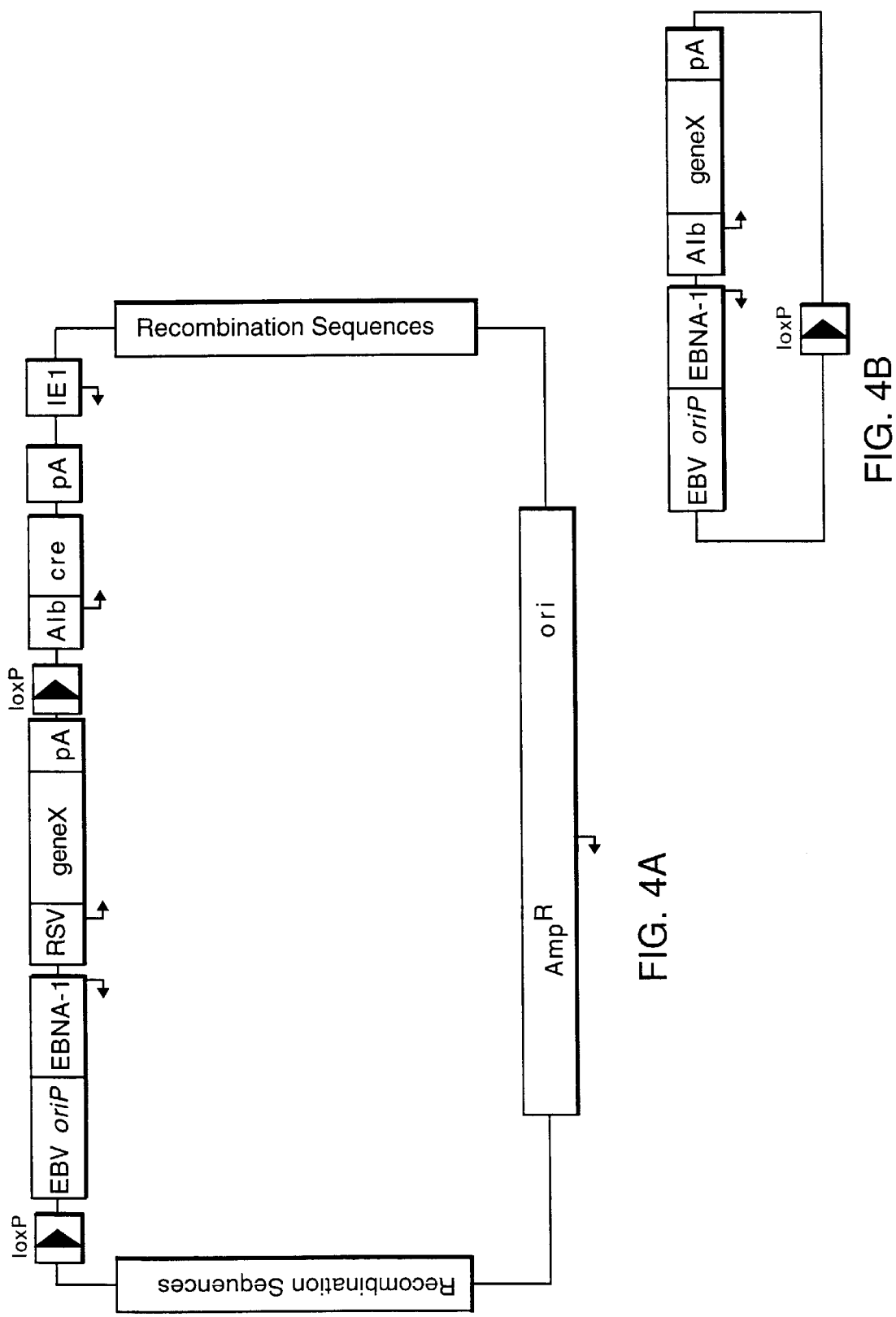
FIG. 4A is a schematic representation of a transfer plasmid that allows excision of a gene cassette.
FIG. 4B is a schematic representation of the gene cassette excised by the transfer plasmid of FIG. 4A. Excision of the gene cassette is mediated by cre-lox recombination. This strategy allows persistence of an exogenous gene in the absence of viral sequences.

Construction of pZ4loxP: The Z4loxP viral genome is a substrate for recombination with bacteriophage P1 cre recombinase. This virus can be used to insert gene cassettes bearing a loxP site into the virus using standard procedures (Patel et al., 1992, Nucl. Acids Res. 20:97–104). A variation of this insertion system may be engineered so that the viral sequences are excised from the remaining gene expression sequences. For example, an auto-excising transfer plasmid may be constructed (FIGS. 4A–4B) to express an exogenous gene in a mammalian cell. This plasmid contains loxP sequences which facilitate excision of the baculoviral sequences. The pZ4loxP transfer plasmid was constructed by inserting a synthetic loxP site into the Z4 transfer plasmid. Two loxP oligonucleotides were synthesized and annealed to each other. The oligonucleotides were:

5'GATCTGACCTAATAACTTCGTATAG-CATACATTATACGAAGTTATATTAAGG3' (SEQ ID NO: 3) and 15 5'GATCCCTTAATATAACTTCGTATAATG-TATGCTATACGAAGTTATTAGGTCA3' (SEQ ID NO:4). The oligonucleotides were annealed by heating them to 80° C. in the presence of 0.25 M NaCl and then allowing the mixture to cool slowly to room temperature before use in the ligation reactions. The annealed oligonucleotides were then ligated to the Z4 transfer plasmid that had been digested with BglII. The ligations and analysis of the resulting clones were performed with standard cloning techniques. Recombinant Z4loxP baculovirus was then generated with conventional methods for recombination into linear baculoviral DNA.

Figure 5:
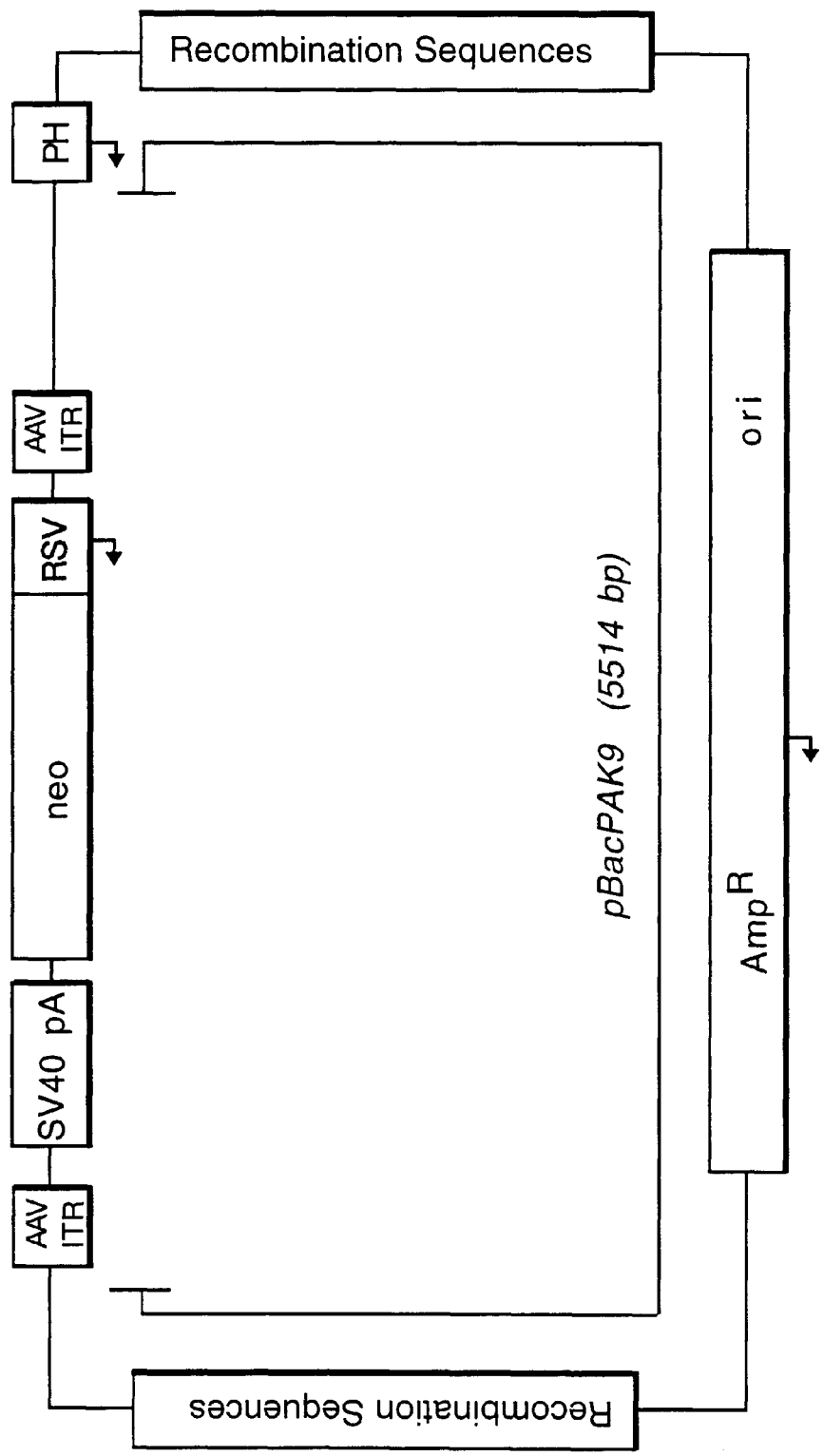
FIG. 5 is a schematic representation of the transfer plasmid, pBV-AVneo, a chimera of baculovirus and Adeno-associated virus sequences. This plasmid is capable of integrating into the genome of the infected cell.

Construction of pBV-AVneo, an AAV Chimera Transfer Plasmid: A baculovirus genome that is capable of integrating into a chromosome of the host cell can also be used in the invention. Such an integrated virus may persist in the cell longer than a non-integrated virus. Accordingly, methods of gene expression involving such viruses may obviate the need for repeated administration of the virus to the cell, thereby decreasing the likelihood of mounting an immune response to the virus. The transfer plasmid pBV-AVneo (FIG. 5) includes the inverted terminal repeats of an Adeno-associated virus (AAV). This transfer plasmid was constructed by excising the neo gene, which encodes G418-resistance, as a BglII-BamHI fragment from pFasV.neo and inserting the fragment into the BamHI site of pAVgal in place of the lacZ gene. Plasmid pAVgal was constructed by replacing the rep and cap coding sequences of AAV with a CMV promoter and a lacZ gene. The resulting intermediate fragment, termed pAV.neo, was digested with PvuI. The large PvuI fragment, which has the CMV promoter driving expression of the neo gene, flanked by the AAV ITRs, then was inserted into the PacI site of pBacPAK9. If desired, a suitable promoter operably linked to an AAV rep gene may be inserted into this construct (e.g., between the AAV ITR and the polyhedrin promoter) to facilitate excision and recombination into the genome. Examples of rep genes that may be inserted into this construct include rep40, rep52, rep68, and rep78.

Figure 6:
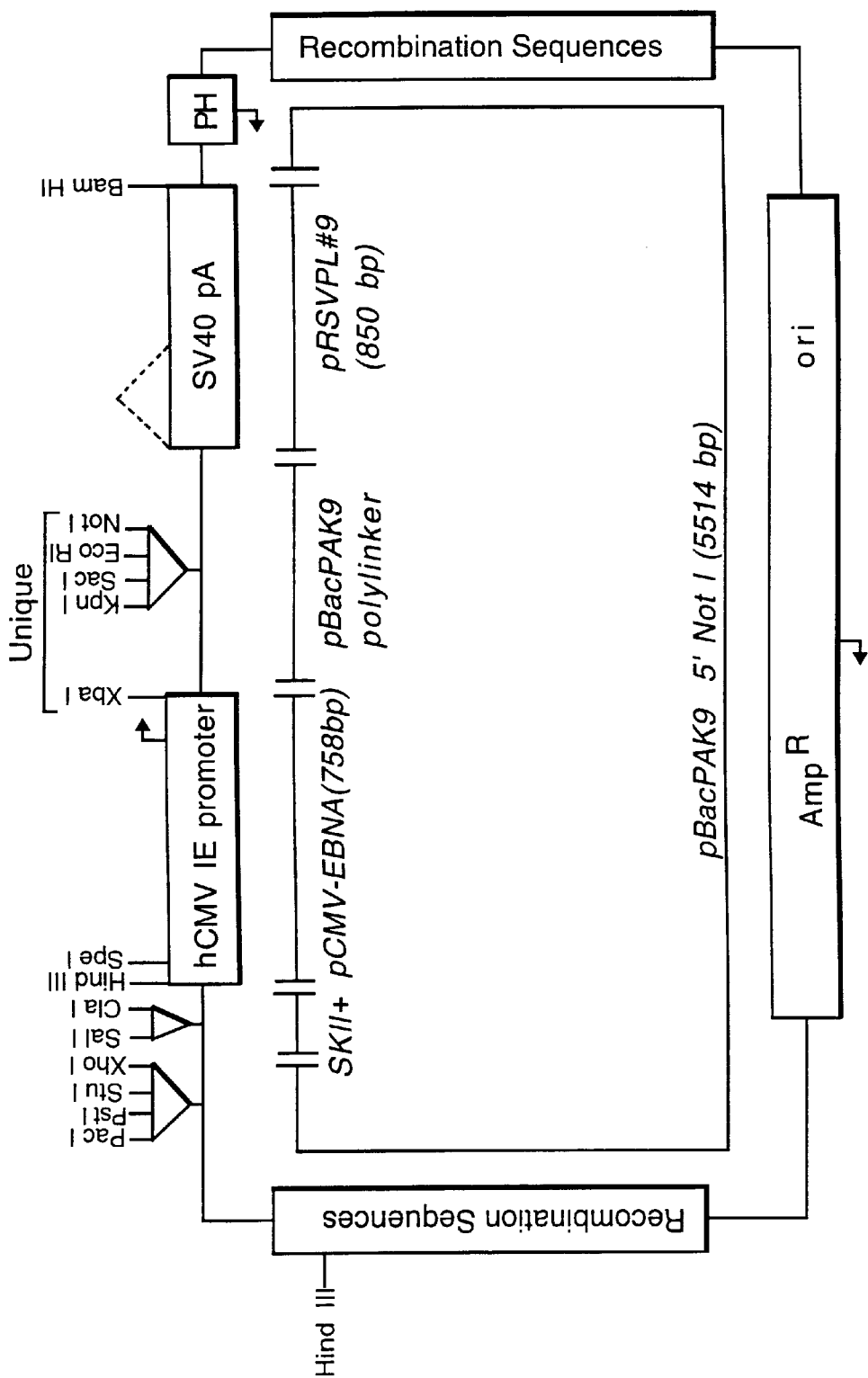
FIG. 6 is a schematic representation of the AcMNPV transfer plasmid pCMV-BV.

Construction of the pCMV-BV Transfer Plasmid: The human cytomegalovirus immediate early promoter, a 758 bp HindIII-XbaI fragment, was excised from pCMV-EBNA (Invitrogen) at HindIII, BamHI and inserted into the HindIII sites of pBluescript (SKII+), yielding plasmid pCMV-SKII+. The promoter was then excised from CMV-SKII+ at the XhoI, BamHI sites and inserted into the XhoI, BglII sites of pSV/BV, yielding plasmid PCMV-BV (FIG. 6). pSV/BV is a modified version of the baculovirus transfer plasmid pBacPAK9 (Clontech), containing an altered polylinker and SV40 splice and polyadenylation signals. pSV/BV was constructed by restriction of pBacPAK9 with NotI, treatment with T4 DNA polymerase to create blunt ends, and self-ligation to remove the NotI site. A new NotI site was then added by ligation of the linker pGCGGCCGC into the SmaI site. Finally, SV40 splice and polyadenylation sequences were added by digestion of PRSVPL with BglII-BamHI, and insertion of the 847 bp fragment into the BamHI site of the modified BacPAK9, yielding pSV/BV.

Figure 7:
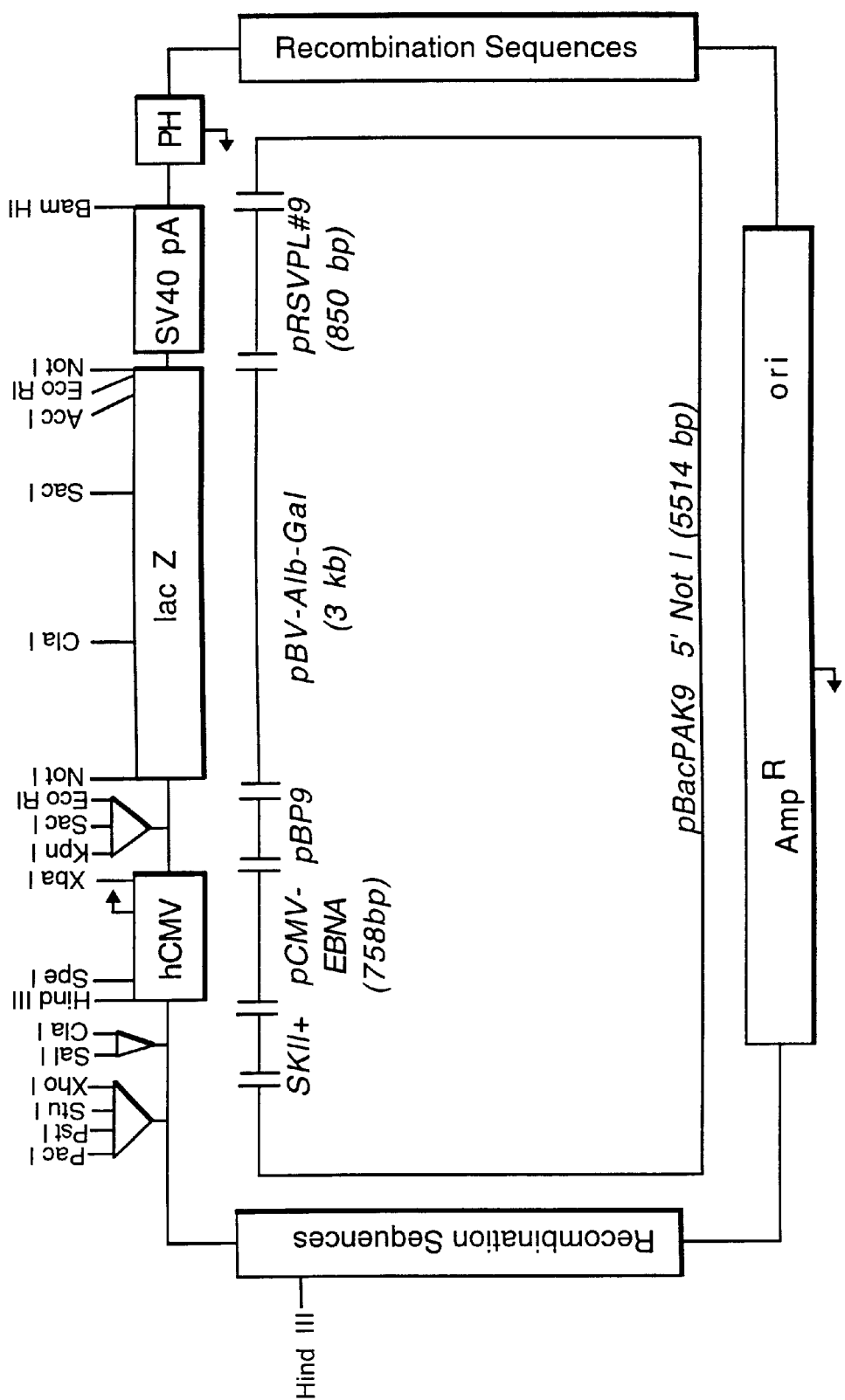
FIG. 7 is a schematic representation of the AcMNPV transfer plasmid pCMVZ-BV.

Construction of the pCMVZ-BV Transfer Plasmid: pCMVZ-BV (FIG. 7) was constructed by restriction of pCMV-BV with NotI and ligation insertion of a 3 kb lacZ fragment. The lacZ fragment was prepared by restriction of pAlb-Gal with NotI.

Figure 8:
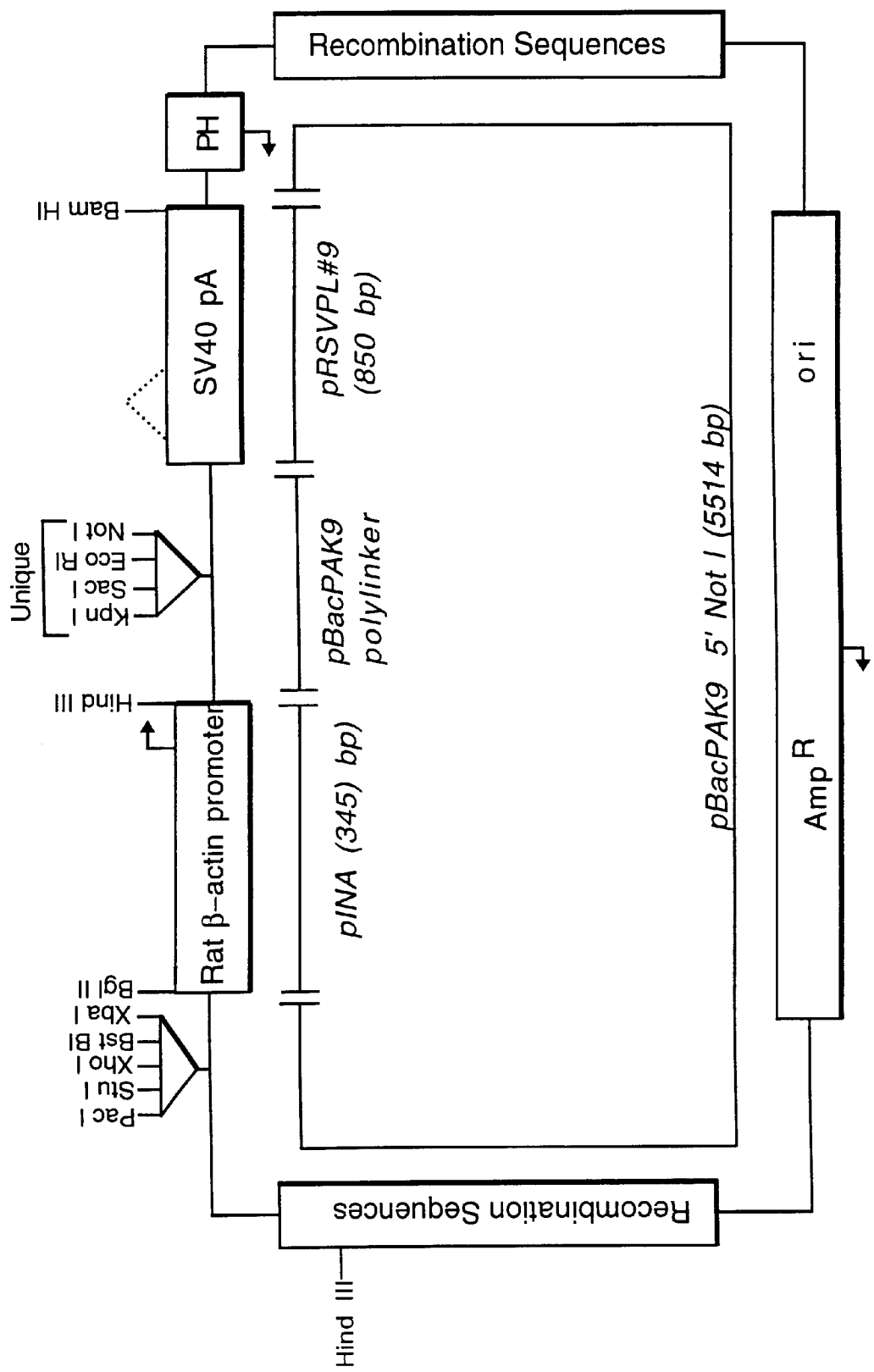
FIG. 8 is a schematic representation of the ACMNPV transfer plasmid pAct-BV.

Construction of the pAct-BV Transfer Plasmid: The 345 bp rat β-actin promoter was excised from pINA (Morgenstern, JP, 1989, Ph.D. Thesis, University College, London, UK) at BglII, BamHI and inserted into the BglII site of pSV/BV, yielding pAct-BV (FIG. 8).

Figure 9:
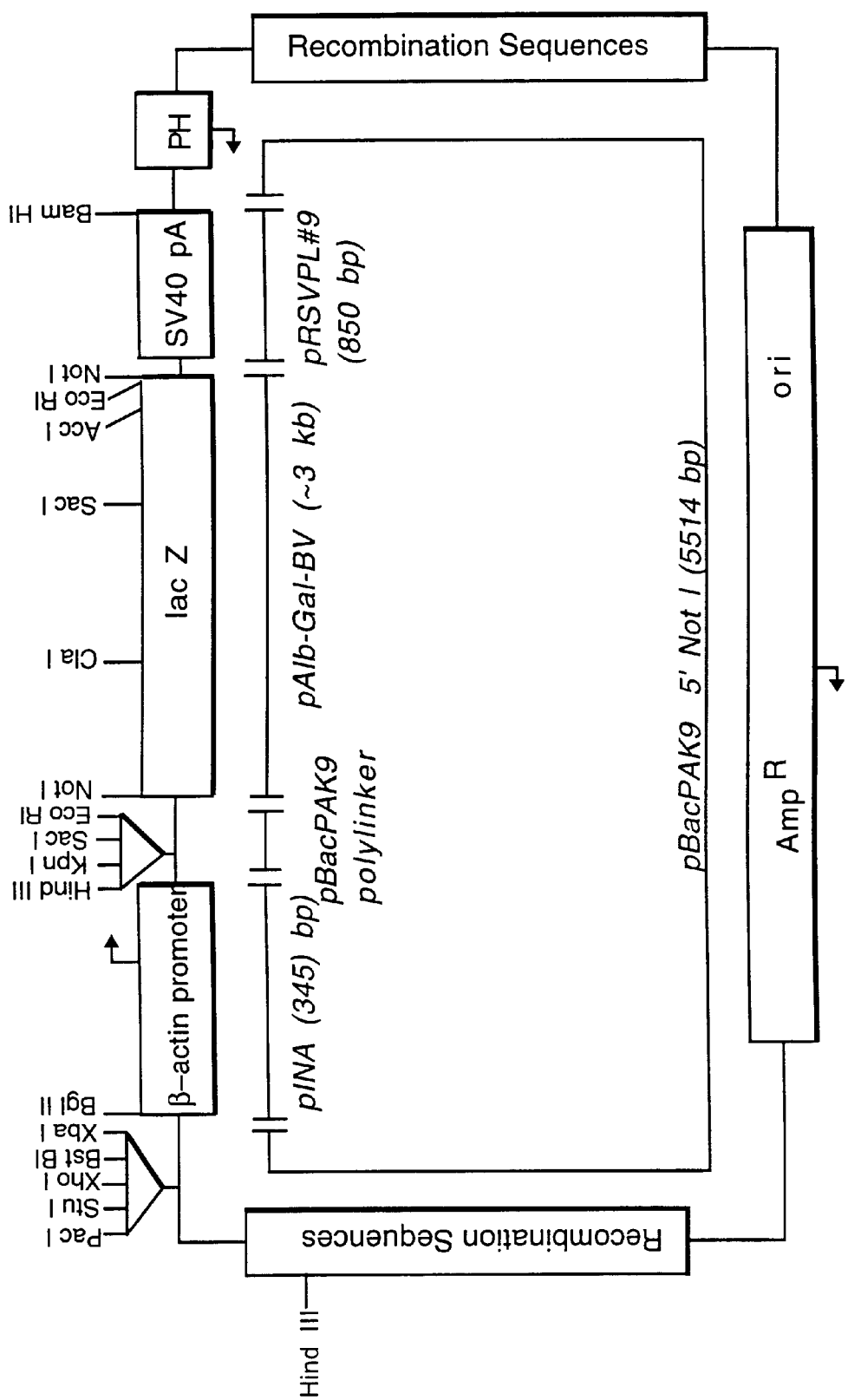
FIG. 9 is a schematic representation of the AcMNPV transfer plasmid pAZ-BV.

Construction of the pAZ-BV Transfer Plasmid: pAZ-BV (FIG. 9) was constructed by restriction of pAct-BV with NotI and ligation insertion of a 3 kb lacZ fragment. The lacZ fragment was prepared by restriction of pAlb-Gal with NotI.

Figure 10:
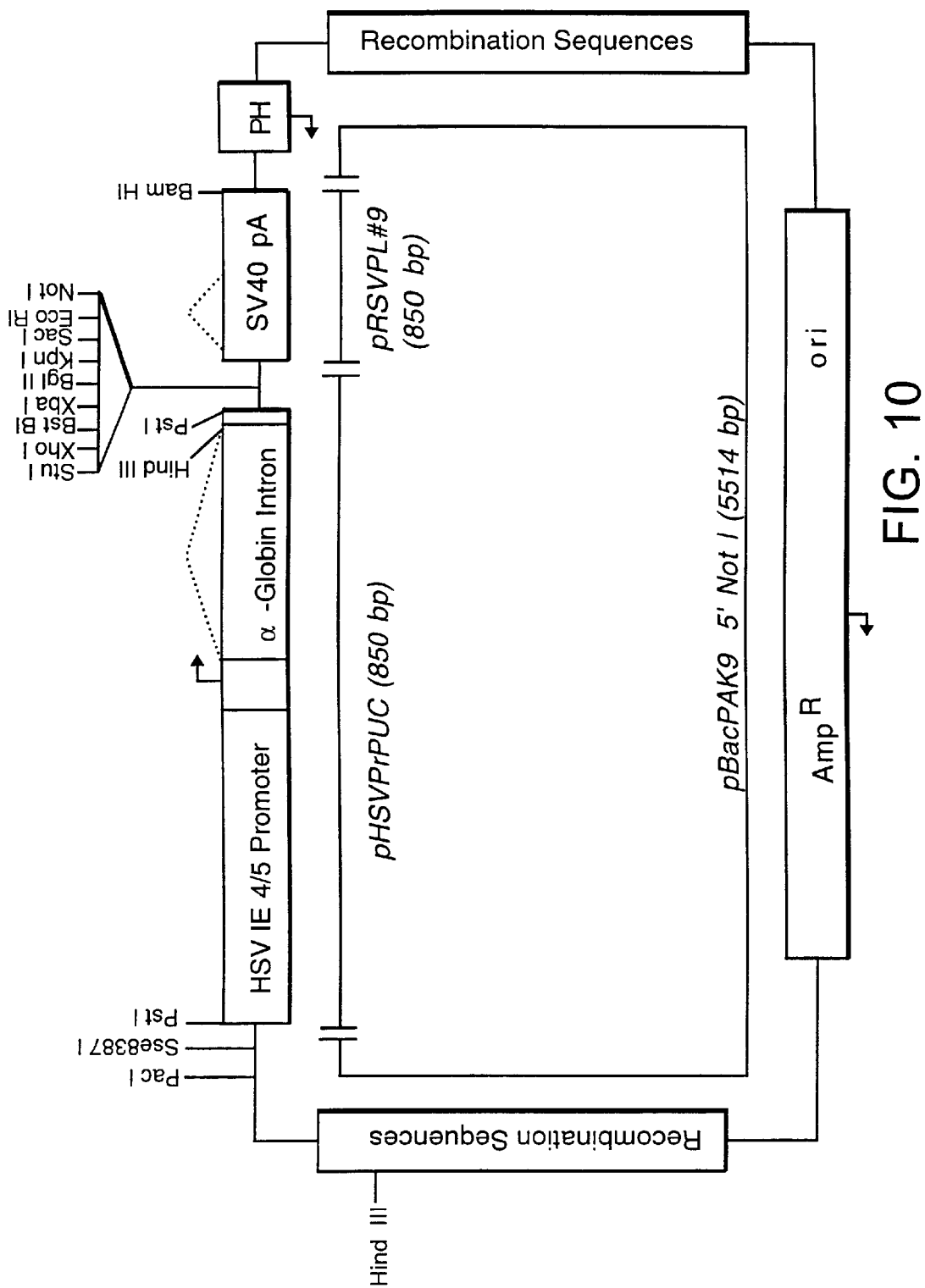
FIG. 10 is a schematic representation of the AcMNPV transfer plasmid pIE45-BV.

Construction of the pIE45-BV Transfer Plasmid: pIE45-BV (FIG. 10) was constructed by restriction of pHSVPrPUC (Neve et al., 1997, Neuroscience 79:435–447) with SphI, followed by treatment with T4 DNA polymerase in the presence of nucleotide triphosphates to create blunt ends. PstI linkers (New England Biolabs, Catalog #1024, pGCTGCAGC) were then added by treatment with T4 DNA ligase, the fragment of approximately 850 bp was subjected to digestion with PstI, and cloned into the PstI site of pSV/BV.

Figure 11:
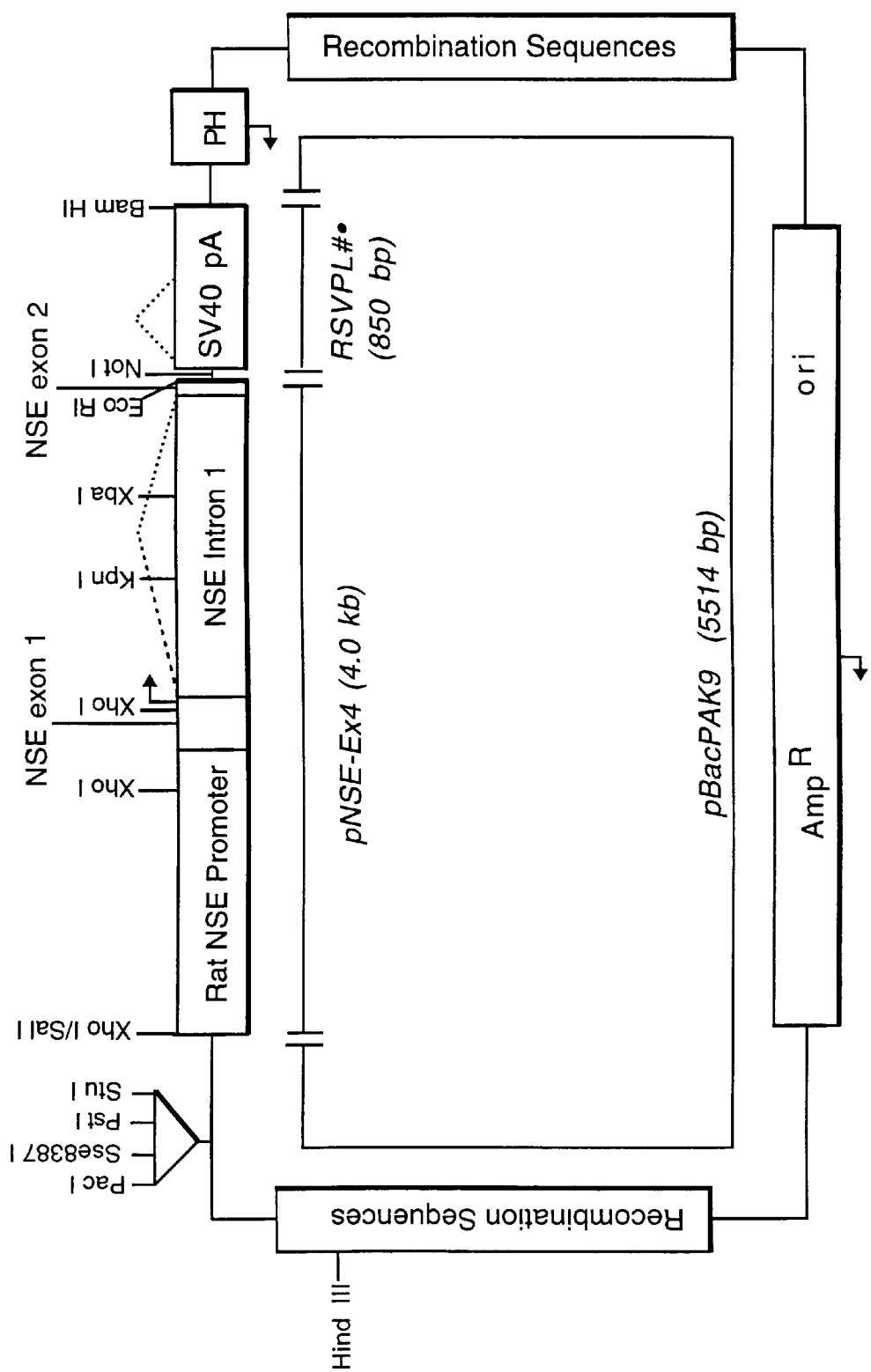
FIG. 11 is a schematic representation of the AcMNPV transfer plasmid pNSE4-BV.

Construction of the pNSE4-BV Transfer Plasmid: pNSE4-DV (FIG. 11) was constructed by restriction of pNSE4 (see, e.g., Quon et al., 1991, Nature 352::239–241 and Forss-Petter et al., 1990, Neuron 5:187–197) with SalI and EcoRI, followed by ligation into the XhoI and EcoRI sites of pSV/BV.

Figure 12:
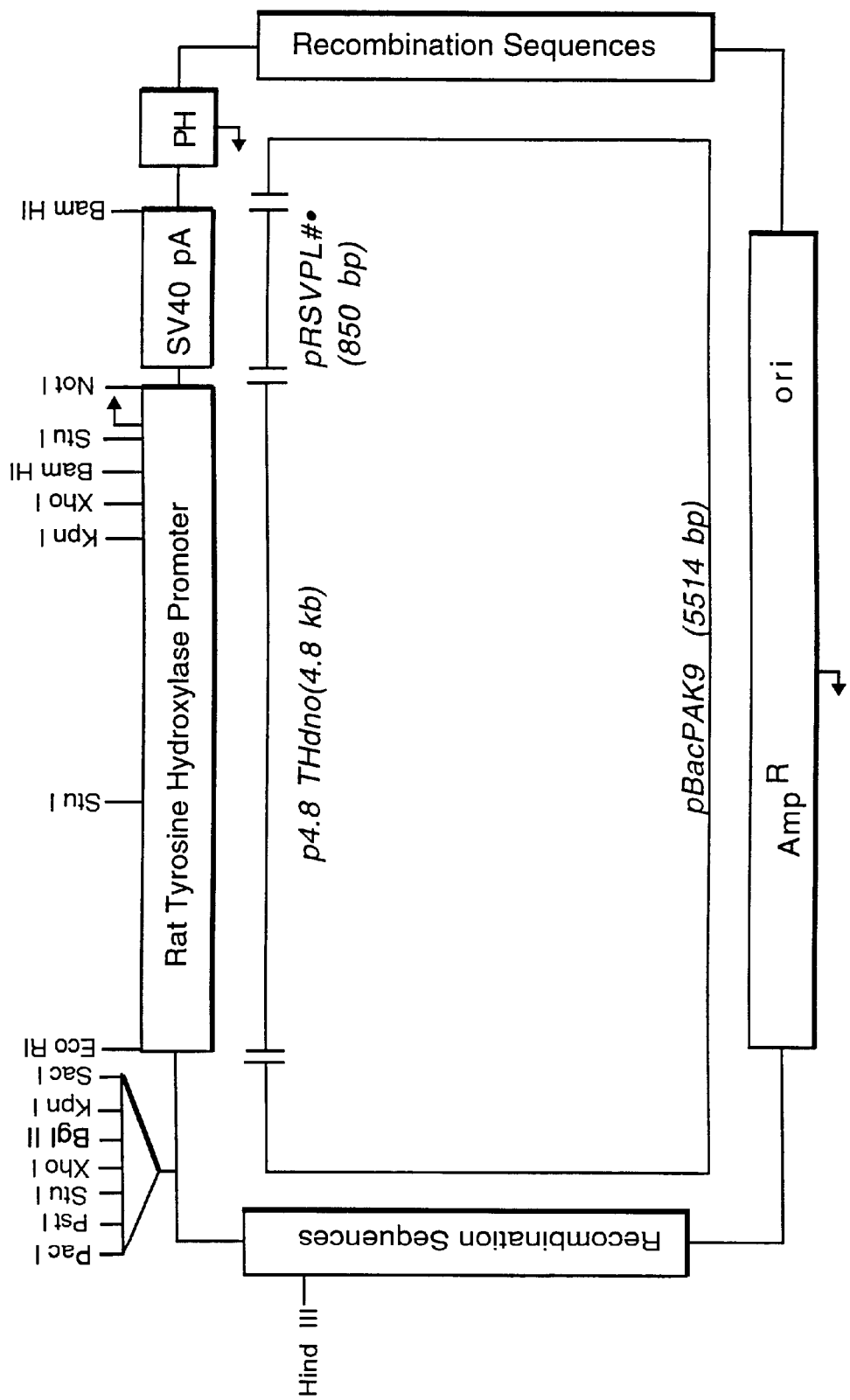
FIG. 12 is a schematic representation of the AcMNPV transfer plasmid pTH/SV40/BP9.

Construction of the pTH/SV40/BP9 Transfer Plasmid: pTH/SV40/BP9 (FIG. 12) was constructed by restriction of pTH4.8 Thdno (Banerjee et al., 1992, J. Neuroscience 12:4460–4467) with EcoRI and NotI, and ligation of the 4.0 kb promoter fragment into pSV/BV, which was also digested with EcoRI and NotI.

Figure 13:
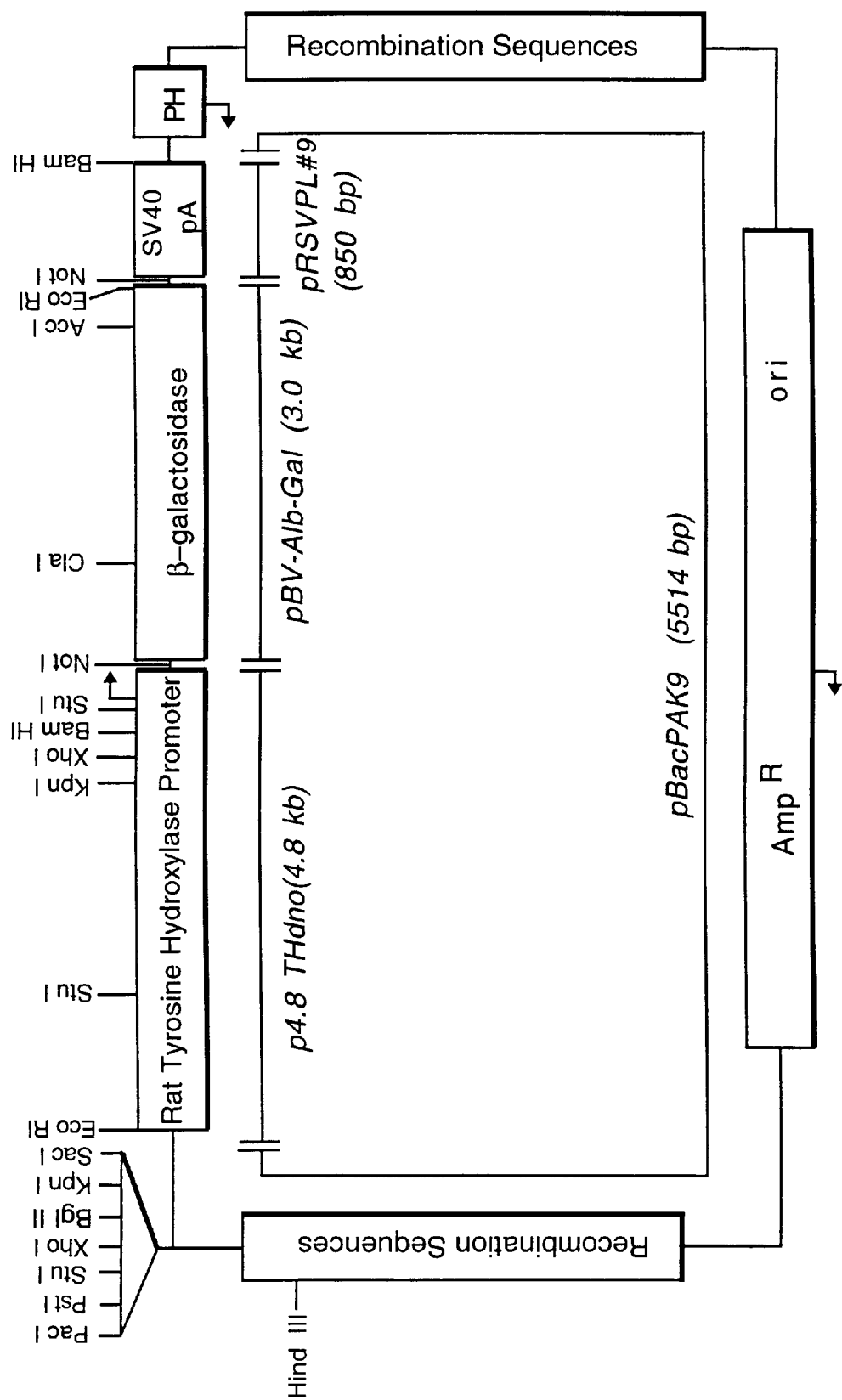
FIG. 13 is a schematic representation of the AcMNPV transfer plasmid pTH-Lac/BP9.

Construction of the pTH-Lac/BP9 Transfer Plasmid: pTh-lac (FIG. 13) was constructed by restriction of pALB-Gal with Not I and isolation of the 3 kb lacZ fragment, which was then ligated into pTH/SV40/BP9 which was also restricted with Not I using T4 DNA ligase.

Propagation of Viruses: Conventional methods can be used to propagate the viruses used in the invention (see, e.g., Burleson, et al., 1992, Virology: A Laboratory Manual, Academic Press, Inc., San Diego, Calif. and Mahy, ed., 1985, Virology: A Practical Approach, IRL Press, Oxford, UK). For example, for baculoviruses used in the experiments described below, the virus was plaque purified and amplified according to standard procedures (see, e.g., O'Reilly et al. infra and Summers and Smith, 1987, A manual of methods for baculovirus vectors and insect cell culture procedures, Texas Agricultural Experiment Station Bulletin No. 1555, College Station, Tex.). AcMNPV and Sf21 cells were propagated by spinner culture in Hinks TNM-FH media (JRH Biosciences) containing 10% fetal bovine serum (FBS) and 0.1% PLURONIC F-68™. Amplified virus can be concentrated by ultracentrifugation in an SW28 rotor (24,000 rpm, 75 minutes) with a 27% (w/v) sucrose cushion in 5 mM NaCl, 10 mM Tris pH 7.5, and 10 mM EDTA. The viral pellet is then resuspended in phosphate-buffered saline (PBS) and sterilized by passage through a 0.45 μm filter (Nalgene). If desired, the virus may be resuspended by sonication in a cup sonicator. AcMNPV was titered by plaque assay on Sf21 insect cells.

III. Examples of Expression of an Exogenous Gene in Mammalian Cells In Vitro

Nearly all mammalian cells are potential targets of non-mammalian viruses, and any cultured or primary cell can rapidly be tested. In the following example, the ability of the Z4 baculovirus to infect 19 different types of cells was tested. In this example, the baculovirus was the Z4 virus, prepared by homologous recombination of the Z4 transfer plasmid with linearized AcMNPV DNA. The tested cells were HepG2, Sk-Hep-1, NIH3T3, NIH3T3 cells expressing a cell-surface asialoglycoprotein receptor, HeLa, CHO/dhfr−, 293, COS, Ramos, Jurkat, HL60, K-562, $C_2C_{12}$ myoblasts, $C_2C_{12}$ myotubes, primary human muscle myoblasts, Hep3B cells, FTO2B cells, Hepal-6 cells, and nerve growth factor-differentiated PC12 cells.

Growth of Cells: Conventional tissue culture methods can be used to grow mammalian cells to be infected (Freshney, 1987, Culture of Animal Cells: A Manual of Basic Techniques, 2nd ed., Alan R. Liss, Inc. New York, N.Y.). These cells were grown and infected as is described above. The cells were grown as follows. HepG2 and Sk-Hep-1 cells were cultured in minimal essential medium as modified by Eagle (EMEM) containing 10% FBS. NIH3T3, HeLa, 293, and COS cells were cultured in DMEM containing 10% FBS. CHO/dhfr⁻ cells were cultured in MEM alpha containing 10% FBS. Ramos, Jurkat, HL60, and K-562 cells were cultured in RPMI 1640 medium containing 10% FBS. HL60 cells were induced to differentiate by culture in the same medium containing 0.5% dimethyl sulfoxide and 1 $\mu$M retinoic acid (Sigma). $C_2C_{12}$ myoblasts were propagated in DMEM containing 20% FBS and differentiated to myotubes during culture in DMEM containing 10% horse serum. PC12 cells were propagated in DMEM containing 5% FBS and 10% horse serum, and were induced to differentiate during culture in DMEM containing 10% FBS, 5% horse serum, and 100 ng/ml nerve growth factor. All cells were seeded one day prior to infection with AcMNPV, and multiplicities of infection were calculated assuming a doubling in cell number during this time. The $C_2C_{12}$ and PC12 cells may have increased in cell number during differentiation, and therefore reflect a somewhat lower moi.

In vitro Infection of Cells: In vitro infection of mammalian cells with a virus can be accomplished by allowing the virus to adsorb onto the cells for 0.1 to 6 hours; preferably, adsorption proceeds for 1 to 2 hours. Generally, a multiplicity of infection of 0.1 to 1,000 is suitable; preferably, the moi is 100 to 500. For relatively refractory cells, a moi of 100 to 1,000 is preferable. For the viruses used in the invention, the titer may be determined with conventional methods which employ the non-mammalian cells that the virus naturally infects. If desired, the mammalian cell to be infected may be maintained on a matrix that contains collagen (e.g., rat tail Type I collagen). Based on cell counting after culture and infection of cells on collagen-coated plates and comparison with cells grown on a conventional EHS matrix, I have found that a collagen matrix increases the susceptibility of cells (e.g., liver cells) to infection by a non-mammalian virus by 10 to 100 fold, relative to a conventional EHS matrix. Commercially-available plates containing a collagen matrix are available (e.g., BIO-COAT™ plates, Collaborative Research), and rat tail collagen is also commercially available (Sigma Chemical and Collaborative Research).

In the in vitro assays described below, standard conditions for infection utilized $2 \times 10^6$ cells and RSV-lacZ AcMNPV at a moi of 15. Adherent cell lines were seeded one day prior to infection. Cells were exposed to virus in 2 ml of medium for 90 minutes, and then the virus-containing medium was removed and replaced with fresh medium. Mock-infected cells were treated with 2 ml medium lacking the viral inoculum.

Detection of Infection and Gene Expression: Delivery of a virus to a cell and expression of the exogenous gene can be monitored using standard techniques. For example, delivery of a virus (e.g., AcMNPV) to a cell can be measured by detecting viral DNA or RNA (e.g., by Southern or Northern blotting, slot or dot blotting, or in situ hybridization, with or without amplification by PCR). Suitable probes that hybridize to nucleic acids of the virus, regulatory sequences (e.g., the promoter), or the exogenous gene can be conveniently prepared by one skilled in the art of molecular biology. Where the invention is used to express an exogenous gene in a cell in vivo, delivery of the virus to the cell can be detected by obtaining the cell in a biopsy. For example, where the invention is used to express a gene in a liver cell(s), a liver biopsy can be performed, and conventional methods can be used to detect the virus in a cell of the liver.

Expression of an exogenous gene in a cell of a mammal can also be followed by assaying a cell or fluid (e.g., serum) obtained from the mammal for RNA or protein corresponding to the gene. Detection techniques commonly used by molecular biologists (e.g., Northern or Western blotting, in situ hybridization, slot or dot blotting, PCR amplification, SDS-PAGE, immunostaining, RIA, and ELISA) can be used to measure gene expression. If desired, a reporter gene (e.g., lacZ) can be used to measure the ability of a particular baculovirus to target gene expression to certain tissues or cells. Examination of tissue can involve: (a) snap-freezing the tissue in isopentane chilled with liquid nitrogen; (b) mounting the tissue on cork using O.C.T. and freezing; (c) cutting the tissue on a cryostat into 10 $\mu$m sections; (d) drying the sections and treating them with 4% paraformaldehyde in PBS, followed by rinsing in PBS; (e) staining the tissue with X-gal (0.5 mg/ml)/ferrocyanide (35 mM)/ferricyanide (35 mM) in PBS; and (f) analyzing the tissue by microscopy.

To measure expression of the reporter gene in the infected cells, calorimetric assays of $\beta$-galactosidase enzymatic activity were performed with standard methods (Norton et al., 1985, Molecular & Cellular Biology 5:281–290). Other conventional methods for measuring $\beta$-galactosidase activity could be used in lieu of the methods employed in this example. Cell extracts were prepared at one day post-infection. Cell monolayers were rinsed three times with PBS, scraped from the dish, and collected by low-speed centrifugation. The cell pellets were resuspended in 25 mM Tris pH 7.4/0.1 mM EDTA and then subjected to three cycles of freezing in liquid nitrogen and thawing in a 37° C. water bath. The extracts were then clarified by centrifugation at 14,000×g for 5 minutes. Standard conditions for assaying $\beta$-galactosidase activity utilized 0.1 ml of cell extract, 0.8 ml of PM-2 buffer, and 0.2 ml of o-nitrophenyl-$\alpha$-D-galactopyranoside (4 mg/ml) in PM-2 buffer for 10 minutes at 37° C. (Norton et al., 1985, Mol. & Cell. Biol. 5:281–290). The reaction was stopped by the addition of 0.5 ml of 1 M sodium carbonate. The amount of substrate hydrolyzed was detected spectrophotometrically at 420 nm, and $\beta$-galactosidase enzymatic activity was calculated with conventional methods (Norton et al., 1985, Mol. & Cell. Biol. 5:281–290). The assay was verified to be linear with respect to extract concentration and time. Extract protein concentrations were determined using the Coomassie Plus protein assay (Pierce) with bovine serum albumin as a standard, and the level of $\beta$-galactosidase activity was expressed as units of $\beta$-galactosidase activity per mg of protein. Other standard protein assays can be used, if desired.

For histochemical staining of $\beta$-galactosidase activity, cells were fixed in 2% (w/v) formaldehyde-0.2% (v/v) paraformaldehyde in PBS for 5 minutes. After several rinses with PBS, the cells were stained by the addition of 0.5 mg/ml of X-gal (BRL) in PBS for 2–4 hours at 37° C.

Assay of 19 Mammalian Cell Types: The following examples illustrate that expression of an exogenous gene can be detected in 14 of the 19 mammalian cell types that were tested. These assays employed two different tests of $\beta$-galactosidase activity. By X-gal staining, the more sensitive assay, exogenous gene expression was detected in 14 of the 19 mammalian cell types. Using an ONPG assay of cell extracts, which is a less sensitive assay, three of the cell lines (HepG2, 293, and PC12) showed statistically significant ($P<0.05$, Student's t-test) higher $\beta$-galactosidase activity after exposure to the virus (Table 2). The human liver tumor line HepG2 exposed to the RSV-lacZ baculovirus expressed greater than 80-fold higher levels of $\beta$-galactosidase than did mock-infected controls. The adenovirus-transformed human embryonal kidney cell line 293 expressed the lacZ reporter gene at a level of about four-fold over background. In addition, PC12 cells, which were differentiated to a neuronal-like phenotype with nerve growth factor, exhibited about two-fold higher β-galactosidase levels after infection with the RSV-lacZ baculovirus. This difference was statistically significant (P=0.019).

TABLE 2

BACULOVIRUS-MEDIATED EXPRESSION OF AN RSV-LACZ REPORTER GENE IN MAMMALIAN CELL LINES.

| Cell Line | β-galactosidase activity (units/mg) Mean ± SD | |
| --- | --- | --- |
| | Mock Infected | RSV-lacZ Virus |
| HepG2 | 0.030 ± 0.004 | 2.628 ± 0.729 |
| Sk-Hep-1 | 0.019 ± 0.003 | 0.019 ± 0.004 |
| NIH3T3 | 0.026 ± 0.003 | 0.023 ± 0.005 |
| HeLa | 0.034 ± 0.009 | 0.036 ± 0.005 |
| CHO/dhfr- | 0.020 ± 0.002 | 0.026 ± 0.005 |
| 293 | 0.092 ± 0.014 | 0.384 ± 0.024 |
| COS | 0.029 ± 0.002 | 0.032 ± 0.007 |
| Ramos | 0.008 ± 0.002 | 0.011 ± 0.004 |
| Jurkat | 0.012 ± 0.004 | 0.007 ± 0.001 |
| HL60 | 0.042 ± 0.039 | 0.014 ± 0.015 |
| K-562 | 0.018 ± 0.006 | 0.017 ± 0.002 |
| $C_2C_{12}$ myoblast | 0.015 ± 0.001 | 0.014 ± 0.003 |
| $C_2C_{12}$ myotube | 0.049 ± 0.011 | 0.042 ± 0.004 |
| PC12 (+NGF) | 0.019 ± 0.005 | 0.033 ± 0.004 |

By histochemical staining, a more sensitive assay, β-galactosidase activity was detected in 14 of the 19 cell lines exposed to virus. Thus, certain of the cell lines that did not yield statistically significantly higher levels of β-galactosidase, as measured in extracts, were, in fact, able to express β-galactosidase at low, but reproducible, frequencies, as detected by the more sensitive X-gal staining procedure. This frequency could be increased by using higher multiplicities of infection such that cells that, at a low moi appear not to express the gene, stain blue at a higher moi. Examples of cell lines that could be transfected in this manner include SK-Hep-1, NIH3T3, HeLa, CHO/dhfr-, 293, Cos, and $C_2C_{12}$ cells. In addition, β-galactosidase activity was detected in primary human muscle myoblasts that were exposed to virus. This finding indicates that baculovirus was able to mediate gene transfer both to primary cells and the corresponding established cell line ($C_2C_{12}$), indicating that expression of the exogenous gene in an established cell line has predictive value for the results obtained with primary cells.

β-galactosidase activity was also detected in Hep3B cells treated with the virus; the level of expression in these cells was nearly equivalent to the level detected with HepG2 cells. In addition, β-galactosidase activity was found in FTO2B (rat hepatoma) cells and Hepal-6 (human hepatoma) cells exposed to virus. β-galactosidase activity was also detected in NIH3T3 cells that were engineered to express the asialoglycoprotein receptor on the cell surface. These cells expressed approximately two times the level of β-galactosidase as did normal NIH3T3 cells. This observation suggests that an asialoglycoprotein receptor may be used to increase susceptibility to viral-mediated gene transfer.

At the moi employed, the Ramos, Jurkat, HL60, and K-562 cell lines did not express statistically significant levels of β-galactosidase, as revealed by β-galactosidase enzyme assays after infection. Based on the results with other mammalian cell lines, it is expected that β-galactosidase activity would be detected in these apparently refractory cell lines when a higher dose (i.e., moi) of virus or longer adsorption time period is utilized.

Even when exposure of cells to the virus results in expression of the exogenous gene in a relatively low percentage of the cells (in vitro or in vivo), the invention can be used to identify or confirm the cell- or tissue-type specificity of the promoter that drives expression of the exogenous gene (e.g., a reporter gene such as a chloramphenicol acetyltransferase gene, an alkaline phosphatase gene, a luciferase gene, or a green fluorescent protein gene). Once identified, such a promoter may be employed in any of the conventional methods of gene expression. Similarly, only relatively low levels of expression are necessary for provoking an immune response (i.e., produce antibodies) in a mammal against the heterologous gene product. Thus, the gene expression method of the invention can be used in the preparation of antibodies against a preferred heterologous antigen by expressing the antigen in a cell of a mammal. Such antibodies may be used inter alia to purify the heterologous antigen. The gene expression method may also be used to elicit an immunoprotective response in a mammal (i.e., be used as a vaccine) against a heterologous antigen. In addition, the invention can be used to make a permanent cell line from a cell in which the virus mediated expression of a cell-immortalizing sequence (e.g., SV40 T antigen).

Histochemical staining using X-gal provided a highly sensitive method for detecting β-galactosidase expression in cells exposed to the modified AcMNPV. When HepG2 cells were exposed to the modified AcMNPV at a moi of 15, about 5–10% of the cells stained with X-gal (FIG. 14A). At a multiplicity of infection (moi) of 125, about 25–50% of the cells were stained (FIG. 14B). No adverse effects of exposure to the virus, such as nuclear swelling, were observed. These data demonstrate that the modified AcMNPV is highly effective at gene transfer into HepG2 cells when a sufficient dose of virus is used. When the Sk-Hep-1 line was exposed to virus at a moi of 15, no stained cells were observed (data not shown). While the majority of Sk-Hep-1 cells that were exposed to virus at a moi of 125, did not stain blue (FIG. 14C), a few cells were found that stained darkly after treatment with this higher doses of virus (FIG. 14D). These data indicate that cells that appear to be refractory to the virus at a relatively low moi can, in fact, be infected, and express the exogenous gene, at a higher moi. Stained cells were not found in mock-infected cultures (data not shown). The frequency of stained cells in the Sk-Hep-1 cell line was estimated to be 2,000–4,000 fold less than in HepG2 cells after exposure to equivalent doses of the modified virus, as determined by cell counting. Thus, the cell type-specificity demonstrated by the modified AcMNPV is relative rather than absolute. These data also indicate that, where a mixture of cells is contacted with the virus (in vitro or in vivo), the dosage of the virus can be adjusted to target the virus to the cells that are infected at a lower moi.

Expression in Primary Cultures of Rat Hepatocytes: This example illustrates that a non-mammalian DNA virus can also be used to express an exogenous gene at high levels in primary cultures of rat hepatocytes. In this experiment, freshly prepared rat hepatocytes were plated onto dishes coated with rat tail collagen as previously described (Rana et al., 1994, Mol. Cell. Biol. 14:5858–5869). After 24 hours, the cells were fed with fresh medium containing RSV-lacZ baculovirus at a multiplicity of infection of approximately 430. After an additional 24 hours, the cells were fixed and stained with X-gal. Over 70% of the cells were stained blue, indicating that they have taken up and expressed the RSV-lacZ cassette (FIG. 15). The frequency of expression obtained in this example is higher than the frequency reported with conventional viral vectors used in gene therapy (e.g., retroviral and Herpes Simplex Virus vectors). Mock-infected cultures did not contain any positively-stained cells (data not shown). Other preferred exogenous genes can be used in lieu of the lacZ gene. In addition, other primary cells can readily be plated and incubated with a non-mammalian cell in lieu of the primary rat hepatocytes.

Expression in Cortex Cultures: The following two examples illustrate that a non-mammalian DNA virus can be used to express an exogenous gene in cultured neuronal and glial cells. For this example, the Z4 virus was prepared from Sf9 cells grown in Hink's TNM-FH media containing 10% FCS, as described above. The virus was purified by banding on a 20–60% sucrose gradient in phosphate-buffered saline. The titer of the virus employed in the following experiments was $3\times10^8$ pfu/ml (for virus stock #1) or $2\times10^9$ pfu/ml (for virus stock #2), as measured on Sf9 cells. Each virus stock was sonicated prior to use.

For the first example, rat cerebral cortex cultures were prepared from E16 embryonic pups. A 24-well dish was seeded with 300,000 cells/well, and, at 4 days post-plating, the cells were infected by adding varying amounts of virus in serum-containing medium to the wells, as is indicated in Table 3. The virus was allowed to adsorb onto the cells for 24 hours.

pfu/ml. To measure the strength of the RSV promoter, the cells were also infected, in separate experiments, with Herpes Simplex Virus (HSV) expressing the lacZ gene under two different promoters. In one case, cells were infected with a HSV in which the lacZ gene was placed under the control of an RSV promoter. The titer of this HSV stock was $2\times10^7$ IU/ml, as measured on PC12 cells with X-gal histochemistry. For comparison, the cells were infected with a HSV in which the lacZ gene was placed under control of the HSV IE4/5 promoter. The titer of this virus was $2\times10^8$ IU/ml, as measured on PC12 cells with X-gal histochemistry. For a negative control, the cells were mock-infected with PBS. Expression of the exogenous lacZ gene was measured by counting the number of blue cells obtained upon staining the cells with X-gal.

The non-mammalian Z4 virus of the invention successfully expressed the exogenous lacZ gene in cultured cortical cells obtained from rat pups at both the E20 and P1 stages of development. With 1–100 $\mu$l of the Z4 virus, 4.9–10% of the cortical cells at the E20 stage, and 2.1–5.75% of the cortical cells at the P1 stage, were stained blue with X-gal, indicating expression of the exogenous gene in those cells. Of the cells infected with 0.1–5.0 $\mu$l of the HSV RSVlacZ virus, as a positive control, 1.9–3.4% of the E20 cells, and 0.45–4.2% of the P1 cells stained blue with X-gal. When the cells were infected with a 5 $\mu$l sample of HSV expressing

TABLE 3

EXPRESSION OF AN EXOGENOUS GENE IN RAT CORTICAL CELLS.

| VIRUS | 1 $\mu$l | 2 $\mu$l | 5 $\mu$l | 10 $\mu$l | 50 $\mu$l | 100 $\mu$l |
|---|---|---|---|---|---|---|
| Z4 Stock #1 | moi = 1<br>no blue cells | moi = 2<br>no blue cells | moi = 5<br>~5 blue cells | moi = 10<br>~20 blue cells | moi = 50<br>~500 blue cells | moi = 100<br>~2200 blue cells (~0.75%) |
| Z4 Stock #2 | moi = 6.7 | moi = 13.3 | moi = 34 | moi = 67 | moi = 335 | moi = 667 |
|  | few blue cells | ~100 blue cells | ~200 blue cells | ~450 blue cells | ~1000 blue cells | ~1300 blue cells |
| PBS |  |  |  | no blue cells | no blue cells | no blue cells |

Expression of the exogenous β-galactosidase gene was measured by counting the number of blue cells after staining the cells with X-gal. Table 3 provides the number of blue cells observed in five fields of the microscope at 10× magnification; each well contained approximately 65 fields. In some wells, the cells at the periphery of the well were preferentially stained.

These data indicate that the exogenous β-galactosidase gene was expressed from the virus in the cultured neuronal cells. In contrast, no blue cells were detected when the cell cultures were mock-infected with PBS. Thus, this non-mammalian virus can be used to express an exogenous gene in neuronal and glial cells, as determined by the detection of blue cells that were, by cell morphology, identified as neurons and glia according to standard criteria.

In the second example, the Z4 baculovirus was used to express an exogenous gene in cultured cortical cells obtained from rat pups at the E20 and P1 stages. The cells from E20 pups were plated in 24-well dishes at 380,000 cells/well. The cells from P1 pups were plated at 300,000 cells/well. The E20 cultures were treated with araC (to inhibit the growth of glia) at 6 days post-plating, and they were infected at 10 days post-plating. The P1 cultures were treated with araC at 2 days post-plating, and they were infected at 6 days post-plating. Samples of each culture were infected with various dilutions of Z4 virus at titer $2\times10^9$ lacZ from the IE4/5 promoter, nearly 100% of the cells stained blue. When E20 or P1 cortical cells were mock-infected with PBS, as a negative control, no blue cells were detected. These data provide additional evidence that the non-mammalian Z4 baculovirus can be used to express an exogenous gene in cortex cells. These data also indicate that the level of expression obtained with the Z4 virus is comparable to the level of expression obtained with HSV.

Figure 16:
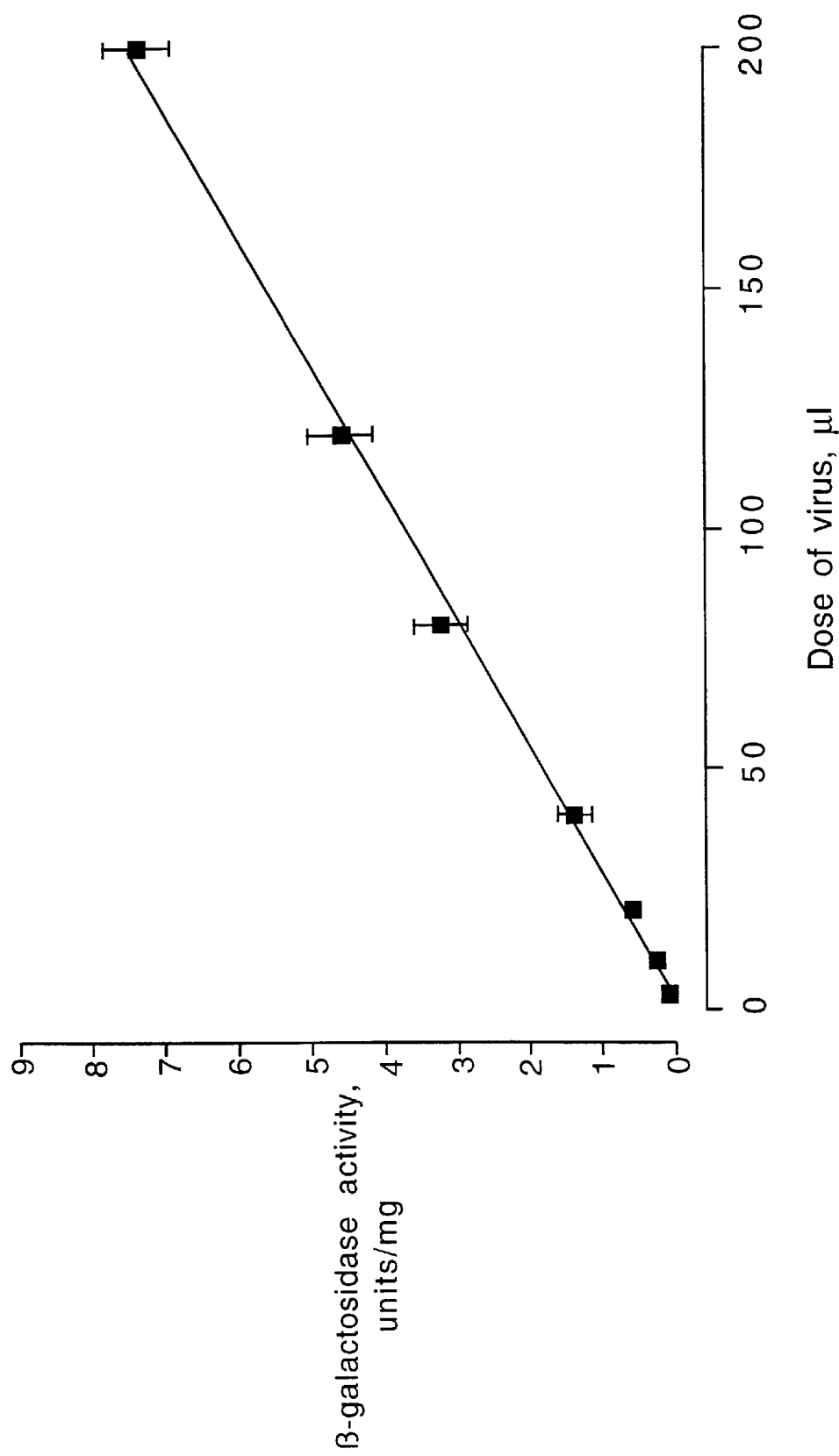
FIG. 16 is a graph displaying the dose-dependence of baculovirus-mediated gene transfer. Here, $10^6$ HepG2 cells were seeded into 60 mm petri dishes, and one day later the cells were exposed to the indicated dose of an ACMNPV virus containing a RSV-lacZ cassette (viral titer=$1.4 \times 10^9$ pfu/ml). At one day post-infection, the cells were harvested, and extracts were prepared and assayed for β-galactosidase enzyme activity. Extract activity is expressed in units of β-galactosidase activity as previously defined (Norton and Coffin, 1985, Mol. Cell. Biol. 5:281–290). Enzyme activity was normalized for the protein content of each extract. Each point is the average of three independent assays, with the error bars representing the standard deviation.

Dose-response of Baculovirus-mediated Gene Transfer: The histochemical data presented above indicate that increasing amounts of β-galactosidase are produced after exposure of mammalian cells to increasing amounts of virus. To quantitate the dose-dependence of baculovirus-mediated gene expression, HepG2 cells were exposed to increasing doses of virus and assayed for β-galactosidase enzyme activity. The amount of enzyme produced was linearly related to the inoculum of virus used over a wide range of doses (FIG. 16). This suggests that entry of each virus particle occurs independently of entry of other virus particles. The maximum dose of virus used in this assay was limited by the titer and volume of the viral stock, and no plateau in the amount of expression was observed using higher doses of virus. Accordingly, these data indicate that, in practicing the invention, one can modulate the level expression (i.e., the percent of cells in which the exogenous gene is expressed) by adjusting the dosage of virus used.

Figure 17:
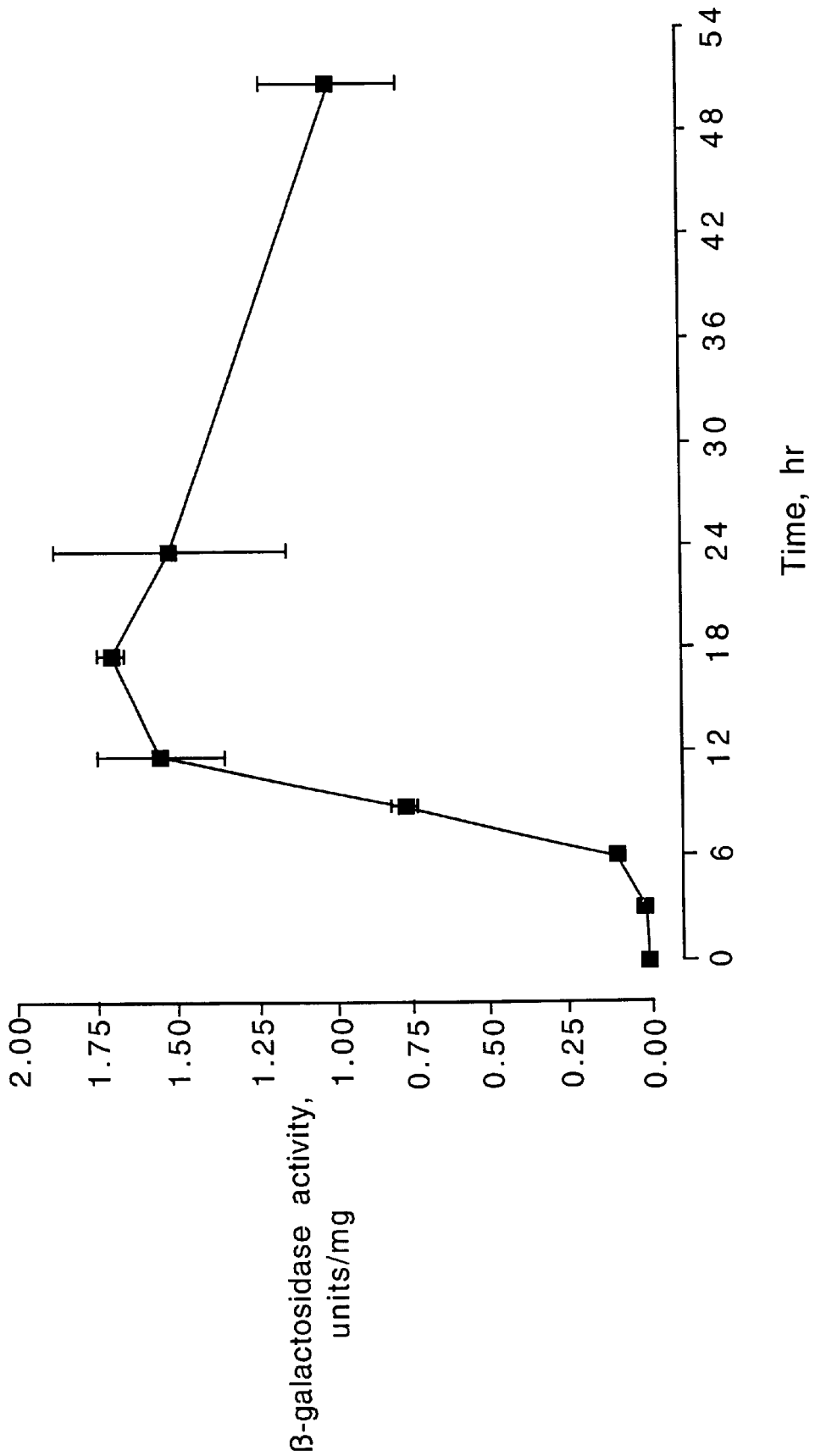
FIG. 17 is a graphic representation of results obtained in a time course of baculovirus-mediated expression. HepG2 cells were infected with AcMNPV virus containing a RSV-lacZ cassette (multiplicity of infection=5) at time zero. After one hour, the medium containing the virus was removed and replaced with fresh medium. Infected cells were harvested at the indicated time points and assayed for β-galactosidase activity as is described above. Each plotted point is expressed as the average of three independent assays, with the error bars representing the standard deviation. Expression from the virus peaked 12–24 hours post-infection and declined thereafter when normalized to total cellular protein.
Figure 18A:
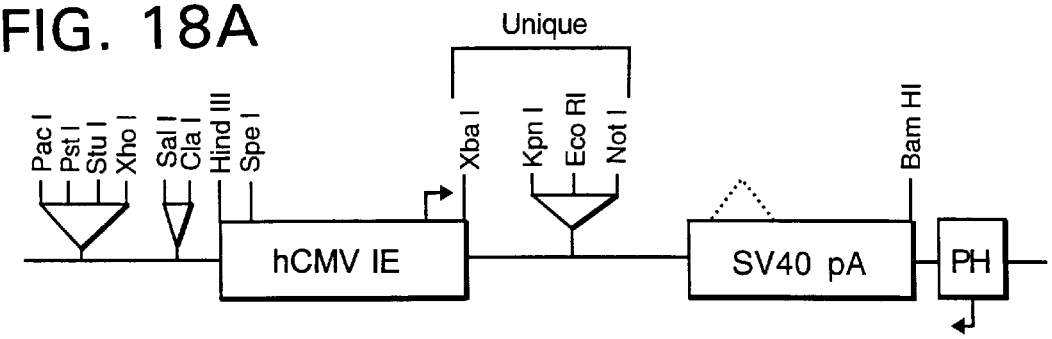
FIG. 18 is a schematic representation of various baculoviral transfer vectors, in which an exogenous gene is operably linked to a viral or mammalian promoter.
Figure 18B:
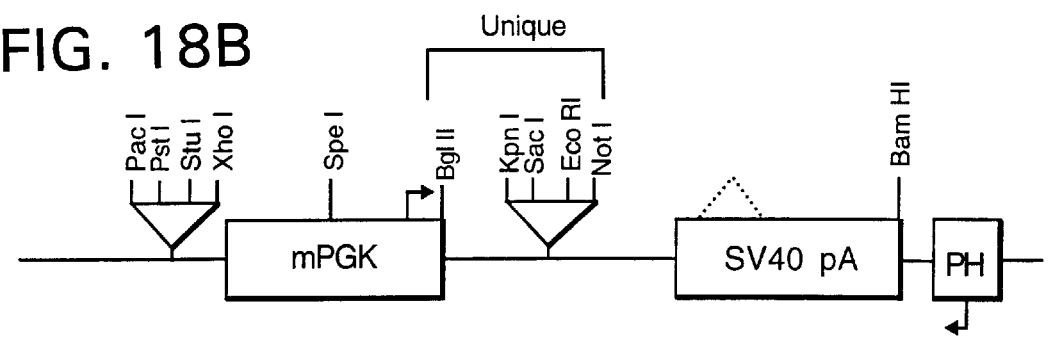
Figure 18C:
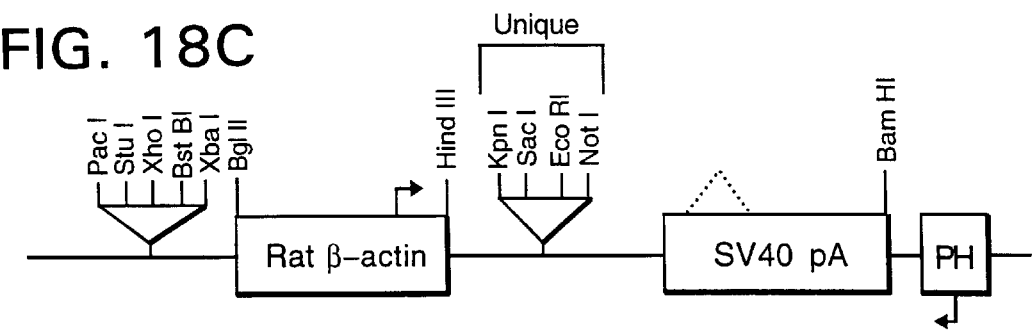
Figure 18D:
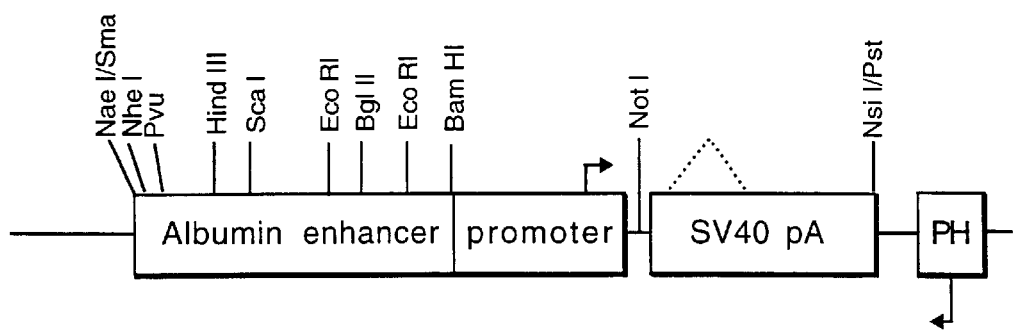

Time Course of Baculovirus-mediated Gene Transfer: HepG2 cells were exposed to the RSV-lacZ virus for 1 hour, after which the cells were harvested at various times and quantitatively assayed for β-galactosidase activity. As is shown in FIG. 17, β-galactosidase activity was detected as early as 6 hours after exposure to the virus, and expression peaked 12–24 hours post-infection. As is expected for an episomal DNA molecule, expression from the RSV-lacZ cassette gradually subsided at later time (FIG. 17 and data not shown). LacZ expression remained detectable by X-gal staining at 12 days post-transfection in fewer than 1 in 1,000 cells (data not shown). This expression of LacZ was not the result of viral spread, because culture supernatants taken from HepG2 cells 10 days post-infection had titers of 10 pfu/ml as determined by plaque assay on Sf21 cells. These data suggest that, where the invention is used in the manufacture of proteins that are purified from HepG2 cells, it may be desirable to isolate the protein from the cell at a time not sooner than 6 hours after infection of the cell. Depending on the half-life of the protein, it may be desirable to isolate the protein shortly after the peak in protein expression (i.e., after approximately 22–26 hours (e.g., approximately 24 hours) post-infection for HepG2 cells). The optimal time period for maximizing isolating the manufactured protein can readily be determined for each protein, virus, and cell.

Expression Occurs De Novo in Mammalian Cells: These examples confirm that expression of the exogenous gene occurs de novo in mammalian cells. To demonstrate that the detected reporter gene activity in the mammalian cells was not simply the result of β-galactosidase being physically associated with AcMNPV virions as they enter the mammalian cell, several experiments were performed that demonstrate that the observed expression of the lacZ reporter gene was the result of de novo synthesis of β-galactosidase. First, the RSV-lacZ virus inoculum was assayed for β-galactosidase activity, and the level of β-galactosidase activity was found to be less than 10% of that expressed after infection of HepG2 cells. Second, HepG2 cells were infected with the RSV-lacZ virus and then cultured in the presence of the protein synthesis inhibitor cycloheximide. Inclusion of cycloheximide after infection inhibited the accumulation of β-galactosidase enzyme activity by more than 90% (Table 4). Third, HepG2 cells were infected at an equivalent moi with BacPAK6 (Clontech), a baculovirus in which the lacZ gene was under control of the viral polyhedrin promoter rather than the RSV promoter (Table 4). The latter virus expresses extremely high levels of β-galactosidase activity in insect cells where the promoter is active (data not shown). In mammalian cells, the viral polyhedrin promoter is inactive, and the virus containing this promoter failed to provide any enzyme activity in mammalian cells (Table 4). In contrast to prior studies of baculovirus interactions with mammalian cells, these data demonstrate that de novo synthesis of lacZ occurs after baculovirus-mediated gene transfer into a mammalian cell.

TABLE 4

BACULOVIRUS-MEDIATED GENE EXPRESSION OCCURS DE NOVO.

| Virus | Drug During Infection | Drug Post Infection | β-galactosidase (% of RSV-lacZ, mean ± SD) |
|---|---|---|---|
| RSV-lacZ | none | none | 100 ± 5.8 |
| none | none | none | 3.2 ± 0.4 |
| RSV-lacZ | none | cycloheximide | 10.3 ± 1.0 |

TABLE 4-continued

BACULOVIRUS-MEDIATED GENE EXPRESSION OCCURS DE NOVO.

| Virus | Drug During Infection | Drug Post Infection | β-galactosidase (% of RSV-lacZ, mean ± SD) |
|---|---|---|---|
| BacPAK6 | none | none | 2.8 ± 0.4 |
| RSV-lacZ | chloroquine | chloroquine | 2.9 ± 0.1 |
| RSV-lacZ | none | chloroquine | 25.1 ± 6.2 |

Baculovirus-mediated Gene Transfer is Inhibited by Lysomotropic Agents: To gain insight into the mechanism by which baculoviruses express an exogenous gene in a mammalian cell, the susceptibility of gene expression to a lysomotropic agent was examined. Like other enveloped viruses, the budded form of AcMNPV normally enters cells via endocytosis, followed by low pH-triggered fusion of the viral envelope with the endosomal membrane, thus allowing escape into the cytoplasm (Blissard et al., 1993, J. Virol. 66:6829–6835; Blissard et al., 1990, Ann. Rev. of Entomol. 35:127–155). To determine whether endosome acidification was necessary for baculovirus-mediated gene transfer into mammalian cells, HepG2 cells were infected with RSV-lacZ AcMNPV in the presence of chloroquine, a lysomotropic agent. HepG2 cells were exposed to AcMNPV virus in media containing or lacking inhibitor for 90 minutes, then the virus-containing media were removed and replaced with fresh media containing or lacking inhibitors as listed.

At one day post-infection, the cells were harvested and extracts were assayed for β-galactosidase activity and protein content. Each value in the table represents the average of three independent assays, with the amount of β-galactosidase produced by the RSV-lacZ AcMNPV virus in the absence of inhibitors assigned a value of 100%. β-galactosidase activity was normalized for protein content of each extract. When 25 μM chloroquine was continuously present during and after exposure of HepG2 cells to the virus, de novo expression of β-galactosidase was completely prevented (Table 4). This suggests that baculovirus-mediated gene transfer is dependent upon endosomal acidification. When chloroquine was added to the cells at 90 minutes after exposure to the virus, only partial inhibition of β-galactosidase expression was observed. Apparently, a portion (≈22%) of the viral particles were able to proceed through the endosomal pathway during the 90 minutes of exposure to the virus.

Baculovirus-mediated Gene Transfer is Enhanced by Butyrate: This example illustrates that butyrate enhances the ability of a baculovirus to express an exogenous gene in a mammalian cell. Five transfer plasmids containing different mammalian promoters were created, as diagrammed in FIG. 18. These vectors were constructed using pSV/BV, a modified version of the baculovirus transfer plasmid pBacPAK9 (Clontech), containing an altered polylinker and SV40 splice and polyadenylation signals. pSV/BV was constructed by restriction of pBacPAK9 with NotI, treatment with T4 DNA polymerase to create blunt ends, and self-ligation to remove the NotI site. A new NotI site was then added by ligation of the linker pGCGGCCGC into the SmaI site. Finally, SV40 splice and polyadenylation sequences were added by digestion of a variant of pRSVglobin with BglII-BamHI, and insertion of the 850 bp fragment into the BamHI site of the modified BacPAK9, yielding pSV/BV. The human cytomegalovirus immediate early promoter, 758 bp HindIII-XbaI fragment, was excised from PCMV-EBNA (Invitrogen) at HindIII, BamHI and inserted into the HindIII, BamHI sites of pBluescript (SKII+), yielding plasmid pCMV-SKII+. The promoter was then excised from CMV-SK II+ at the XhoI, BamHI sites and inserted into the XhoI, BglII sites of pSV/BV, yielding plasmid pCMV/BV. The 500 bp mouse phosphoglycerate kinase (PGK) promoter was prepared by cutting pKJ1-neo (Tybulewicz et al., 1991, Cell 65: 1153–1163) with EcoRI and made blunt with T4 DNA polymerase to remove the EcoRI site. The resulting pKJ1 plasmid lacking the EcoRI site was amplified by pfu polymerase chain reaction using the primers 5'ACCGCGGATC-CAATACGACTCACTATAG3' (SEQ ID NO: 5) and 5'CGGAGATCTGGAAGAGGAGAACAGCGCGGCAG3' (SEQ ID NO: 6). The amplified PGK promoter was then digested with XhoI and BglII and inserted into the same sites of pSV/BV yielding PKJ1/BV. The 345 bp rat β-actin promoter was excised from PINA (6) at BglII, BamHI and inserted into the BglII site of pSV/BV yielding pβ-actin/BV. The 2.3 kb albumin enhancer and 700 bp albumin promoter were excised from pGEMAlbSVPA (Zaret et al., 1988, Proc. Natl. Acad. Sci. 85:9076–9080) at NaeI, NsiI and inserted into the SmaI, PstI sites of pSV/BV. The RSVlacZ transfer plasmid used (also referred to herein as the Z4 virus) is described above. A 3.0 kb Lac Z cassette was inserted into the NotI site of all of the plasmids constructed (See FIG. 18).

Recombinant viruses were generated by contransfection of the baculovirus transfer vectors with linear BP6 viral DNA (Clontech) into Sf21 cells. The recombinant viruses were purified through three rounds of plaque isolation and amplified on Sf21 cells. The amplified viruses were concentrated by ultracentrifugation as described above and titered by a 96-well method on Sf21 insect cells (O'Reilly et al., 1992, Baculovirus Expression Vectors: A Laboratory Manual, W.H. Freeman, New York, N.Y.).

The human hepatocellular carcinoma cell line HepG2 was infected with each recombinant virus at a multiplicity of infection of 100. Two million cells were infected in a final volume of 1 ml Eagle's Minimum Essential Medium in a 60 mm tissue culture dish. The infection was allowed to proceed for two hours, then 4 ml of complete medium was added to the cells. In a second series of HepG2 infections, the conditions of the first infections were repeated with the exception that after the infection had proceeded for 2 hours 25 µl of sodium butyrate (100 mM) was added to the cells with 1.5 ml complete media. As a control, cells were mock-infected to assess background β-galactosidase enzyme activity. The cell monolayers were collected after 24 hours and prepared for a calorimetric assay (with ONPG) of β-galactosidase enzymatic activity as described above. Hepatocytes were isolated by collagenase perfusion and plated on rat tail collagen as previously described (Boyce et al., 1996, Proc. Natl. Acad. Sci. 93:2348–2352). Assay conditions (time and amount of extract used) were varied to be within the linear range of the assay. The amount of product was determined by spectrophotometry and β-galactosidase enzyme activity was calculated. The Coomassie Plus protein assay (Pierce) was used to determine the protein concentration of the extracts, and results were expressed as units of β-galactosidase normalized to total protein content of the extract. The amount of background activity from the mock-infected cells was subtracted from the total amount of enzyme activity for each of the promoters. Each infection was performed in triplicate, and expressed as the mean average with standard deviation (Table 5).

As shown in Table 5, the incorporation of viral or mammalian cellular promoters into baculoviruses allows for expression of an exogenous gene product in mammalian cells. The CMV promoter led to the highest level of β-galactosidase activity, with the RSV and β-actin promoters producing lower levels of β-galactosidase activity. At the moi of virus employed in this example, the albumin and PGK promoters showed no activity above background levels in extracts of cells that were not treated with butyrate, although positively stained cells were detected by X-gal staining. The addition of sodium butyrate to the cells after infection led to detectable levels of β-galactosidase expression with all of the promoters tested. After treating cells with sodium butyrate, the CMV promoter showed a five-fold increase in expression of the β-galactosidase reporter gene. The RSV LTR, albumin, pGK1, and β-actin promoters all led to increased gene expression after treatment with butyrate. Without being bound to any particular theory, it is postulated that sodium butyrate increases cellular differentiation and histone acetylation, which increases transcription.

TABLE 5

COMPARISON OF VARIOUS PROMOTER STRENGTHS WITH AND WITHOUT SODIUM BUTYRATE

| Promoter | Hep G2 −butyrate | Hep G2 +butyrate | Rat Hepatocytes −butyrate |
|---|---|---|---|
| CMV | 17 ± 1.4[a] | 86 ± 33 | 18 ± 1.2 |
| RSV | 1.0 ± 0.1 | 2.2 ± 0.1 | 0.25 ± 0.11 |
| pGK1 | 0.0 ± 0.0 | 0.02 ± 0.02 | 0.64 ± 0.58 |
| Albumin | 0.0 ± 0.0 | 0.08 ± 0.04 | 0.15 ± 0.08 |
| β-actin | 0.1 ± 0.01 | 0.05 ± 0.02 | 0.25 ± 0.07 |

[a]Promoter strength is expressed in Units/mg of β-galactosidase.

Analysis of RNA Expression From Viral Promoters in HepG2 Cells: One advantage of using a non-mammalian virus to express an exogenous gene in a mammalian cell is that, due to a lack of appropriate host cell factors, the non-mammalian viral promoters may not be active in the mammalian cell. To determine whether AcMNPV viral gene are expressed in HepG2 cells, the viral RNA was analyzed. In these experiments, HepG2 cells were infected with the Z4 virus at a moi of approximately 30. At 18 hours post-infection, the cells were harvested, and total cellular RNA was extracted from the cells. The total cellular RNA was analyzed by Northern blotting for expression of viral genes. The probe included a 1.7 kbp PacI-SalI fragment from pAcUW1 (Pharmingen) which contains the viral late gene, p74, as well as the very late (hyperexpressed) gene, p10. Total cellular RNA from Z4-infected Sf9 insect cells was employed as a positive control. While extremely strong signals were detected for p10 and p74 for the control insect cells, no signal was observed for Z4-infected HepG2 cells or uninfected control cells.

Additional experiments that used reverse transcriptase-PCR (RT-PCR), a highly sensitive method, provided further evidence that the majority of viral genes are not transcribed in the mammalian HepG2 cells. RT-PCR analysis was performed with RNA prepared from Z4-infected HepG2, uninfected HepG2, or infected Sf9 cells at 6 or 24 hours post-infection. HepG2 cells were infected at a moi of 10 or 100. At 6 hours post-infection, no RT-PCR product was observed from the viral p39, ETL, LEF1, IE1, or IE-N genes at either dose of virus in Z4-infected HepG2 cells. In contrast, RT-PCR products were readily detected in Z4-infected Sf9 cells. At 24 hours post-infection, no expression of these gene was detected in HepG2 cells infected at a moi of 10. At 24 hours post-infection, no expression of the viral p39, ETL, or LEF1 genes was observed in HepG2 cells infected at an moi of 100. However, at this high does of virus, low levels of expression from the viral IE1 and IE-N genes was observed. The low level of expression detected at an moi of 100 was nonetheless significantly lower than the level of expression in insect cells.

Expression of these genes may result from recognition of the viral TATA box by mammalian transcription factors (i.e., transcription of the immediate early genes by RNA polymerase II (see, e.g., Hoopes and Rorhman, 1991, Proc. Natl. Acad. Sci. 88:4513–4517). In contrast to the immediate early genes, the late or very late viral genes are transcribed by a virally-encoded RNA polymerase that, instead of requiring a TATA box, initiates transcription at a TAAG motif (O'Reilly et al., supra). Accordingly, expression of the viral late or very late genes is naturally blocked in mammalian cells. If desired, expression of the immediate early genes can be blocked by deleting those genes, using conventional methods.

While certain viruses have an intrinsic ability to infect liver cells, infection of liver cells by other viruses may be facilitated by a cellular receptor, such as a cell-surface asialoglycoprotein receptor (ASGP-R). HepG2 cells differ from Sk-Hep-1 human hepatocytes and NIH3T3 mouse fibroblast cells by the presence of ASGP-R on the cell surface. In certain of the above experiments, β-galactosidase was expressed in fewer Sk-Hep-1 cells (FIG. 14B) or NIH3T3 cells than HepG2 cells. The lacZ gene was expressed in HepG2 cells at a frequency estimated as greater than 1,000 fold more than that in Sk-Hep-1 cells, based on quantitative counts of X-gal stained cells. Normal hepatocytes have 100,000 to 500,000 ASGP-R, with each receptor internalizing up to 200 ligands per day. The ASGP-R may facilitate entry of the virus into the cell by providing a cell-surface receptor for glycoproteins on the virion. The glycosylation patterns of insect and mammalian cells differ, with the carbohydrate moieties on the surface of the virion produced in insect cells lacking terminal sialic acid. Those carbohydrate moieties may mediate internalization and trafficking of the virion. In addition to the ASGP-R, other galactose-binding lectins that exist in mammals (see, e.g., Jung et al., 1994, J. Biochem. (Tokyo) 116:547–553) may mediate uptake of the virus.

If desired, the cell to be infected can be modified to facilitate entry of the baculovirus into the cell. For example, ASGP-R can be expressed on the surface of a cell to be infected by the virus (e.g., baculovirus). The genes encoding the ASGP-R have been cloned (Spiess et al., 1985, J. Biol. Chem. 260:1979 and Spiess et al., 1985, Proc. Natl. Acad. Sci. 82:6465), and standard methods (e.g., retroviral, adeno-associated virus, or adenoviral vectors or chemical methods) can be used for expression of the ASGP-R in the cell to be infected by a virus. Other suitable mammalian lectins can be substituted for the ASGP-R in such methods (see, e.g., Ashwell et al., 1982, Ann. Rev. Biochem. 51:531–534). Other receptors for ligands on the virion, such as receptors for insect carbohydrates or the CD4 receptor for HIV, can also be expressed on the surface of the mammalian cell to be infected to facilitate infection (see, e.g., Monsigny et al., 1979, Biol. Cellulaire 33:289–300).

Entry into the cell also can be facilitated by modifying the virion, e.g., through chemical means, to enable the virion to bind to other receptors on the mammalian cell (see, e.g., Neda, et al., 1991, J. Biol. Chem. 266:14143–14146 and Burns et al., 1993, Proc. Natl. Acad. Sci. 90:8033–8037). Alternatively, the glycosylation patterns and levels of baculovirus can be modified by growing the virus on Ea4 cells, which are derived from *Estigmena acrea* (e.g., as described by Rooney et al. in Nature Biotech). In addition, one can modify the virus such that it expresses mammalian glycosylation enzymes (Jarvis et al., 1996, Nature Biotech. 14:1288–1292).

IV. Therapeutic Use of a Non-mammalian DNA Virus Expressing an Exogenous Gene

The discovery that a non-mammalian DNA virus efficiently expressed a lacz reporter gene in several mammalian cells indicates that a non-mammalian DNA virus can be used therapeutically to express an exogenous gene in a cell of a mammal. For example, the method of the invention can facilitate expression of an exogenous gene in a cell of a patient for treatment of a disorder that is caused by a deficiency in gene expression. Numerous disorders are known to be caused by single gene defects (see Table 6), and many of the genes involved in gene deficiency disorders have been identified and cloned. Using standard cloning techniques (see, e.g., Ausubel et al., *Current Protocols in Molecular Biology*, John Wiley & Sons, (1989)), a non-mammalian virus can be engineered to express a desired exogenous gene in a mammalian cell (e.g., a human cell).

TABLE 6

EXAMPLES OF DISORDERS THAT CAN BE TREATED WITH THE INVENTION AND GENE PRODUCTS THAT CAN BE MANUFACTURED WITH THE INVENTION

| Gene Product | Disorder |
|---|---|
| fumarylacetoacetate hydrolase | hereditary tyrosinemia |
| phenylalanine hydroxylase | phenylketonuria |
| LDL receptor | familial hypercholesterolemia |
| alpha-1 antitrypsin | alpha-1 antitrypsin deficiency |
| glucose-6-phosphatase | glycogen storage diseases |
| porphobilinogen deaminase | diseases caused by errors in porphyrin metabolism, e.g., acute intermittent porphyria |
| CPS-I, OTC, AS, ASL, or arginase | disorders of the urea cycle |
| factors VIII & IX | hemophilia |
| cystathione B-synthase | homocystinuria |
| branched chain ketoacid decarboxylase | maple syrup urine disease |
| albumin | hypoalbuminemia |
| isovaleryl-CoA dehydrogenase | isovaleric acidemia |
| propionyl CoA carboxylase | propionic acidemia |
| methyl malonyl CoA mutase | methylmalonyl acidemia |
| glutaryl CoA dehydrogenase | glutaric acidemia |
| insulin | insulin-dependent diabetes |
| B-glucosidase | Gaucher's disease |
| pyruvate carboxylase | pyruvate carboxylase deficiency |
| hepatic phosphorylase or phosphorylase kinase | glycogen storage diseases |
| glycine decarboxylase, H-protein, or T-protein | non-ketotic hyperglycinemias |
| Wilson's disease copper-transporting ATPase | Wilson's disease |
| Menkes disease copper-transporting ATPase | Menkes disease |
| cystic fibrosis transmembrane conductance regulator | cystic fibrosis |

The invention can also be used to facilitate the expression of a desired gene in a cell having no obvious deficiency. For example, the invention can be used to express insulin in a hepatocyte of a patient in order to supply the patient with insulin in the body. Other examples of proteins that can be expressed in a mammalian cell (e.g., a liver cell) for delivery into the system circulation of the mammal include hormones, growth factors, and interferons. The invention can also be used to express a regulatory gene or a gene encoding a transcription factor (e.g., a VP16-tet repressor gene fusion) in a cell to control the expression of another gene (e.g., genes that are operably-linked to a tet operator sequence; see, e.g., Gossen et al., 1992, Proc. Natl. Acad. Sci. 89:5547–5551). In addition, the invention can be used in a method of treating cancer by expressing in a cell a cancer therapeutic gene, such as a gene encoding a tumor suppressor (e.g., p53), tumor necrosis factor, thymidine kinase, diphtheria toxin chimera, or cytosine deaminases (see, e.g., Vile and Russell, 1994, Gene Therapy 1:88–98).

Other useful gene products include RNA molecules for use in RNA decoy, antisense, or ribozyme-based methods of inhibiting gene expression (see, e.g., Yu et al., 1994, Gene Therapy 1:13–26). If desired, the invention can be used to express a gene, such as cytosine deaminase, whose product will alter the activity of a drug or prodrug, such as 5-fluorocytosine, in a cell (see, e.g., Harris et al., 1994, Gene Therapy 1: 170–175). Methods such as the use of ribozymes, antisense RNAs, transdominant repressors, polymerase mutants, or core or surface antigen mutants can be used to suppress hepatitis viruses (e.g., hepatitis virus A, B, C, or D) in a cell. Other disorders such as familial hemachromatosis can also be treated with the invention by treatment with the normal version of the affected gene.

Preferred genes for expression include those genes that encode proteins that are expressed in normal mammalian cells (e.g., hepatocytes or lung cells). For example, genes encoding enzymes involved in the urea cycle, such as the genes encoding carbamoyl phosphate synthetase (CPS-I), ornithine transcarbamylase (OTC), arginosuccinate synthetase (AS), arginosuccinate lyase (ASL), and arginase are useful in this method. All of these genes have been cloned (for OTC, see Horwich et al., 1984, Science 224:1068–1074 and Hata et al., 1988, J. Biochem (Tokyo) 103:302–308; for AS, see Bock et al., 1983, Nucl. Acids Res. 11:6505; Surh et al., 1988, Nucl. Acids Res. 16:9252; and Dennis et al., 1989, Proc. Natl. Acad. Sci. 86:7947; for ASL, see O'Brien et al., 1986, Proc. Natl. Acad. Sci. 83:7211; for CPS-I, see Adcock et al., 1984, (Abstract) Fed. Proc. 43:1726; for arginase, see Haraguchi et al., Proc. Natl. Acad. Sci. 84:412). Subcloning these genes into a baculovirus can be readily accomplished with common techniques.

The therapeutic effectiveness of expressing an exogenous gene in a cell can be assessed by monitoring the patient for known signs or symptoms of a disorder. For example, amelioration of OTC deficiency and CPS deficiency can be detected by monitoring plasma levels of ammonium or orotic acid. Similarly, plasma citrulline levels provide an indication of AS deficiency, and ASL deficiency can be followed by monitoring plasma levels of arginosuccinate. Parameters for assessing treatment methods are known to those skilled in the art of medicine (see, e.g., Maestri et al., 1991, J. Pediatrics, 119:923–928).

The non-mammalian DNA virus (e.g., baculovirus) can be formulated into a pharmaceutical composition by admixture with a pharmaceutically acceptable non-toxic excipient or carrier (e.g., saline) for administration to a mammal. In practicing the invention, the virus can be prepared for use in parenteral administration (e.g., for intravenous injection (e.g., into the portal vein)), intra-arterial injection (e.g., into the femoral artery or hepatic artery), intraperitoneal injection, intrathecal injection, or direct injection into a tissue or organ (e.g., intramuscular injection). In particular, the non-mammalian virus can be prepared in the form of liquid solutions or suspensions in conventional excipients. The virus can also be prepared for intranasal or intrabronchial administration, particularly in the form of nasal drops or aerosols in conventional excipients. If desired, the virus can be sonicated in order to minimize clumping of the virus in preparing the virus.

In practicing the invention, the virus can be used to infect a cell outside of the mammal to be treated (e.g., a cell in a donor mammal or a cell in vitro), and the infected cell then is administered to the mammal to be treated. In this method, the cell can be autologous or heterologous to the mammal to be treated. For example, an autologous hepatocyte obtained in a liver biopsy can be used (see, e.g., Grossman et al., 1994, Nature Genetics 6:335). The cell can then be administered to the patient by injection (e.g., into the portal vein). In such a method, a volume of hepatocytes totaling about 1%–10% of the volume of the entire liver is preferred. Where the invention is used to express an exogenous gene in a liver cell, the liver cell can be delivered to the spleen, and the cell can subsequently migrate to the liver in vivo (see, e.g., Lu et al., 1995, Hepatology 21:7752–759). If desired, the virus may be delivered to a cell by employing conventional techniques for perfusing fluids into organs, cells, or tissues (including the use of infusion pumps and syringes). For perfusion, the virus is generally administered at a titer of $1 \times 10^6$ to $1 \times 10^{10}$ pfu/ml (preferably $1 \times 10^9$ to $\times 10^{10}$ pfu/ml) in a volume of 1 to 500 ml, over a time period of 1 minute to 6 hours. If desired, multiple doses of the virus can be administered to a patient intravenously for several days in order to increase the level of expression as desired.

The optimal amount of virus or number of infected cells to be administered to a mammal and the frequency of administration are dependent upon factors such as the sensitivity of methods for detecting expression of the exogenous gene, the strength of the promoter used, the severity of the disorder to be treated, and the target cell(s) of the virus. Generally, the virus is administered at a multiplicity of infection of about 0.1 to 1,000; preferably, the multiplicity of infection is about 5 to 100; more preferably, the multiplicity of infection is about 10 to 50.

V. Examples of Use of a Non-mammalian Virus to Express an Exogenous Gene In Vivo The following examples demonstrate that a non-mammalian DNA virus can be used to express an exogenous gene in a cell in vivo. These examples also demonstrate that in vivo gene expression can be achieved by administering the virus by intravenous injection, intranasal administration, or direct injection of the virus into the targeted tissue. The first example demonstrates expression of an exogenous gene in brain cells in vivo. The second example provides evidence of expression of an exogenous gene in liver, following intravenous injection of the virus. In the third example, expression of the exogenous gene is detected in skin after topical application of the Z4 virus to injured skin. In the remaining examples, a virus carrying an exogenous gene was injected directly into an organ. These examples demonstrate in vivo expression of an exogenous gene in skin, liver, spleen, kidney, stomach, skeletal muscle, uterus, and pancreas.

Infection Into Portal Vein: For the first example, 0.5 ml of Z4 virus ($\approx 1.4 \times 10^9$ pfu/ml) was injected (at a rate of $\approx 1$ ml/min) into the portal vein of a single rat. At approximately 72 hours after infection, lacZ expression was detectable in at least one liver cell of the cryosections that were examined by conventional histochemical methods. The efficiency of expression may be increased by any one, or a combination of, the following procedures: (1) pre-treating the animal with growth factors; (2) partial hepatectomy, (3) administration of immunosuppressants to suppress any immune response to the virus; (4) use of a higher titer or dose of the virus; (5) infusion of the virus by surgical perfusion to the liver (e.g., in order to limit possible non-specific binding of the virus to red blood cells); and/or (6) sonication of the virus to minimize clumping of the virus.

Expression in Brain: For the second example, a 2 µl sample of Z4 virus (at a titer of $4.8 \times 10^{10}$ pfu/ml) was injected, using stereotactic procedure, into the olfactory bulb in the brain of an anesthetized adult rat. The virus was injected slowly (over a 30 minute time period) to avoid compressing the brain tissue. At 1 day post-injection, the rat was euthanized, and the brain tissue was processed for detection of expression of the exogenous lacZ gene by X-gal histochemistry. Injection of the Z4 virus into the brain resulted in in vivo expression of lacZ, as was evidenced by patches of cells that were strongly stained blue. More than $10^4$ cells were stained blue upon injection of approximately $10^7$ pfu. These data thus indicate that an exogenous gene can be expressed in the brain of a mammal by injecting into the brain a non-mammalian DNA virus whose genome includes the exogenous gene.

Topical Application and Expression in Skin: This example demonstrates that topical application of the Z4 virus to abraded skin of a mouse can result in expression of a heterologous gene in the skin. These experiments involved four differently-treated areas on the skin of a mouse. Two of the areas (an abraded and a non-abraded area) were treated with phosphate-buffered saline. The other two areas (an abraded and a non-abraded area) were treated with the Z4 virus (50 µl at $4.8 \times 10^{10}$ pfu/ml). After treatment, each area of the skin was cut into sections using a cryostat.

Topical application of the Z4 virus (50 µl at $4.8 \times 10^{10}$ pfu/ml) to injured skin of a mouse resulted in expression of the exogenous gene in nearly 100% of the cells of the basal layer of the epidermis. Staining of deeper structures was not detected. In one cryostat section, various areas of the epidermis were stained in multiple sections. In a second cryostat section, occasional blue cells were present. In a third cryostat section, patches of staining were detected, and in a fourth cryostat section, the staining was nearly continuous and very dark. Although the pattern of gene expression varied slightly between the four cryostat sections obtained from this area of skin, the example demonstrates that topical application of the Z4 virus to abraded skin consistently resulted in expression of the heterologous gene in skin.

Injection Into a Tissue or Organ: In the following examples, expression of an exogenous gene was detected in vivo after a non-mammalian DNA virus carrying the gene was injected directly into four distinct organs. For these examples, the Z4 virus was prepared from 1 L of Z4-infected (moi of 0.5) Sf9 cells grown in spinner culture in serum-free medium. The cells and debris were removed by centrifuging the cell culture at 2000 rpm for 10 minutes. The virus was pelleted by centrifugation through a sucrose cushion in an SW28 rotor at 24,000 rpm for 75 minutes. For preparation of this virus stock, 33 ml of cleared virus was layered over a 3 ml sucrose cushion (27% sucrose (w/v) in 10 mM Tris-HCl (pH 7.5), 1 mM EDTA (TE)). The virus was resuspended by overnight incubation at 4° C. in 0.3 ml TE per tube. The virus was purified by banding in a 20–60% sucrose (w/v in TE) gradient in SW41 tubes that were centrifuged at 38,000 rpm for 75 minutes. The virus bands were collected with a syringe and pelleted in SW50.1 rotor centrifuged at 30,000 rpm for 60 minutes. The virus pellet was resuspended in a total of 0.7 ml PBS by overnight incubation at 4° C. The titer of the concentrated Z4 stock, as determined in a conventional plaque assay, was $4.8 \times 10^{10}$ pfu/ml.

To assay for gene expression in vivo, the Z4 virus was administered Balb/c female mice by direct injection of a 50 µl aliquot of the concentrated virus ($2.4 \times 10^9$ pfu total) into either the liver, spleen, kidney, muscle, uterus, pancreas, or skin of a mouse. Surgery was required for administration to liver, spleen and kidney. To spread the virus throughout an organ, the 50 µl virus sample was injected into two or three sites in an organ. A 50 µl sample of PBS was used as a negative control. For assaying gene expression in the liver, only one lobe of the liver was injected, and a separate mouse received the PBS injection as a negative control. For assaying gene expression in the spleen, an uninjected mouse served as a negative control. For assaying gene expression in kidney, muscle, and skin, contralateral controls were performed (the Z4 virus was injected into the right side of the organ, and PBS was injected into the left of the organ). For assaying expression in muscle, the virus was injected into the tibealis anterior hind leg muscle after shaving the mouse. For assaying expression in skin, the abdomen of the mouse was shaved, and 50 µl of Z4 virus were injected into a marked section of the abdomen. At 24 hours post-injection, the mice were sacrificed and dissected. The Z4- and PBS-injected organs were frozen in liquid nitrogen, and 7 µm thin sections were prepared using a cryostat (Reichert-Jung Cryocut 1800). β-galactosidase activity was measured by fixing the thin sections and staining with X-gal, as described above. Each of the organs that received the Z4 virus expressed the exogenous lacZ gene in vivo. In each case, the PBS negative control did not promote expression of the exogenous gene.

Injection and Expression in Skin: In this example, in vivo expression of the exogenous lacZ gene of Z4 was observed in mouse skin after injection of $2.4 \times 10^9$ pfu into the skin. A high level of expression (over 25% of cells within the area of injection) was achieved in the dermis after subcutaneous injection of the virus. Although the muscle layer was predominantly unstained, positive staining of some skeletal muscle fibers was observed. As a negative control, PBS was injected into the skin. Although some staining was observed in the sebaceous glands, it is most probably due to the presence of bacteria. A low level of staining was also detected in the dermis. Similar results were obtained when the Z4 virus was applied topically to uninjured (non-abraded) skin, although no clear epidermal staining was detected. Nonetheless, these data indicate that the Z4 virus can be used to express a heterologous gene in the skin of a mammal when the virus is injected subcutaneously into the mammal.

Expression in Liver: In this example, expression of the exogenous gene was detected in liver. Blue coloration, indicative of β-galactosidase expression, was detected in multiple areas of the injected lobe. Although the most intense coloration was at the point of injection, the internal areas of the liver sections exhibited the blue coloration that is indicative of gene expression. Expression of the exogenous gene appeared to be detected both in hepatocytes and Kupffer cells of the lobes that received the Z4 virus. In contrast, uninjected lobes from the same liver were negative. These results thus indicate that an exogenous gene can be expressed in a liver cell by injecting into the liver a non-mammalian DNA virus encoding the gene.

Expression in Spleen: In this example, thin sections of the spleen were assayed for gene expression following injection of the virus carrying the exogenous gene into the spleen. Spleen cells that had received the Z4 virus in vivo expressed the lacZ gene. The blue coloration was detected in cells located throughout the entire spleen. The intensity of blue coloration obtained with spleen cells was less than the intensity obtained with liver cells. Nonetheless, the blue coloration was indicative of significant expression of the exogenous gene. No blue coloration was detected in a spleen that did not receive the virus. These data thus indicate that an exogenous gene can be expressed in a spleen cell in vivo upon injection of a non-mammalian DNA virus whose genome carries the gene.

Expression in Kidney: In this example, in vivo expression of an exogenous gene was detected in a kidney that was injected with Z4 as described above. The Z4-injected kidney displayed clear blue coloring that is indicative of lacZ expression; in contrast, a PBS-injected control kidney displayed no blue coloration. The blue coloration was primarily around the edges of the sections of the kidney. Indirect immunofluorescence also indicated that the viral particles were concentrated in the edges of the sections, providing a correlation between gene expression and localization of the virus. These data thus indicate that a non-mammalian DNA virus can be used to express an exogenous gene in a kidney cell in vivo.

Expression in Stomach: In this example, the Z4 virus (50 μl) was injected into the center of the stomach of Balb/C mice. The animals were sacrificed on the day following injection, and the stomachs were frozen in liquid nitrogen, and cryostat sectioned and stated as previously described. Cell transfection was observed in gastric mucosal and muscle cells. Positive staining was detected in glands, with most staining occurring at the bases of the glands. These observations indicate that a non-mammalian DNA virus can be used to express a heterologous gene in the stomach of mice. In these experiments, blue staining was also detected in the lumen. The blue coloration in that particular region may result from bacteria in the gut, rather than expression from the virus.

Expression in Skeletal Muscle: In this example, in vivo expression of the exogenous lacZ gene of Z4 was detected in muscle after direct injection of virus into the tibialis anterior. Blue coloration was found only in discrete loci in the muscle, and the coloration was not as intense or widespread as the coloration observed in liver, spleen, or skin. Nonetheless, the blue coloration was significant, indicating that a non-mammalian DNA virus can be used to express an exogenous gene in muscle in vivo.

Expression in Uterus: In this example, expression of the lacZ reporter gene was detected in the uterus. A 50 μl aliquot of the Z4 virus ($2.4 \times 10^9$ pfu) was injected directly into the uterus of a mouse. The animal was sacrificed on the day following injection, and cryostat sections were prepared as previously described. Staining of the sections with X-gal produced blue coloration in an area of the uterus with little tissue disruption. The positive cells were mostly endometrial stromal cells, rather than gland elements. These data indicate that a non-mammalian DNA virus can be used to express a heterologous gene in the uterus of a mammal.

Expression in Pancreas: This example demonstrates that a non-mammalian DNA virus can be used to express a heterologous gene in the pancreas of a mammal. A 50 μl aliquot of the Z4 virus ($2.4 \times 10^9$ pfu) was injected directly into the pancreas of a mouse. On the day following injection, the mouse was sacrificed, and the pancreas was stained with X-gal according to conventional methods. Large areas of positive cells were detected, indicating that the Z4 virus successfully expressed the lacZ gene in the pancreas.

Summary: In sum, these examples demonstrate that a non-mammalian DNA virus (e.g., a baculovirus) can be used to express an exogenous gene in a mammalian cell in vivo. These examples employed several distinct animal model systems and methods of administering the virus. In each and every case, the non-mammalian DNA virus successfully expressed the exogenous gene in vivo. These data thus provide support for the assertion that a non-mammalian DNA virus can be used to express an exogenous gene in other, non-exemplified cells in vivo. In addition, in at least some tissues, the level of expression in vivo was, surprisingly, higher than the level that would have been predicted from the corresponding in vitro experiments (e.g., the brain versus cultured neurons). All of these examples provide evidence of the in vivo utility of the invention.

What is claimed is:

1. A method of expressing an exogenous gene in a mammalian cell, said method comprising:
    a) introducing into the cell a nuclear non-mammalian DNA virus or an entomopoxvirus, other than the prokaryote virus the genome of which comprises said exogenous gene under the control of a promoter that induces expression of the exogenous gene in the cell to produce an infected cell; and
    b) maintaining the infected cell under conditions such that said exogenous gene is expressed.

2. The method of claim 1, wherein said virus is an insect virus.

3. The method of claim 2, wherein the insect virus is an Aedes Densovirus.

4. The method of claim 2, wherein the insect virus is a *Bombxy mori* Nuclear Polyhedrosis Virus.

5. The method of claim 1, wherein said cell is selected from the group consisting of liver cells, kidney cells, neuronal cells, fibroblasts, cells of the central nervous system, splenic cells, muscle cells, skin cells, endothelial cells, epithelial cells, and stem cells.

6. The method of claim 1, wherein said cell is a primary cell.

7. The method of claim 1, wherein said virus is introduced into said cell in vitro.

8. The method of claim 1, wherein said mammalian cell is a human cell.

9. The method of claim 1, wherein said gene is transcribed into an antisense RNA.

10. A nucleic acid comprising:
    a genome of a nuclear non-mammalian DNA virus or an entomopoxvirus;
    an exogenous mammalian gene; and
    an exogenous mammalian-active promoter operably linked to said exogenous gene.

11. The nucleic acid of claim 10, wherein said virus is an insect virus.

12. A nucleic acid comprising:
    a genome of a nuclear non-mammalian DNA virus or an entomopoxvirus;
    an exogenous antisense RNA gene, the RNA encoded by said gene being complementary to a nucleic acid of a gene that is expressed in a cell at an undesirably high level; and
    an exogenous mammalian-active promoter operably linked to said exogenous antisense RNA gene.

13. The nucleic acid of claim 12, wherein said virus is an insect virus.

14. A non-human cell that contains a nucleic acid, wherein said nucleic acid comprises:
    a genome of a nuclear non-mammalian DNA virus or an entomopoxvirus;
    an exogenous mammalian gene; and
    an exogenous mammalian-active promoter operably linked to said exogenous gene.

15. The cell of claim 14, wherein said virus is an insect virus.

16. The cell of claim 14, wherein said cell is a primary cell.

17. A nucleic acid comprising:
a genome of a nuclear non-mammalian DNA virus or an entomopoxvirus;
an exogenous cancer therapeutic gene selected from the group consisting of tumor necrosis factor genes, thymidine kinase genes, chimeric diphtheria toxin genes, and cytosine deaminase genes; and
an exogenous mammalian-active promoter operably linked to said exogenous cancer therapeutic gene.

18. The nucleic acid of claim 17, wherein said virus is an insect virus.

19. A nucleic acid comprising:
a genome of a nuclear non-mammalian DNA virus or an entomopoxvirus;
an exogenous gene selected from the group consisting of RNA decoy genes and ribozyme genes; and
an exogenous mammalian-active promoter operably linked to said exogenous gene.

20. A non-mammalian DNA virus comprising the nucleic acid of claim 10.

21. The non-mammalian DNA virus of claim 20, wherein the virus is an insect virus.

22. A cell in vitro that contains a nucleic acid, wherein said nucleic acid comprises:
a genome of a nuclear non-mammalian DNA virus or an entomopoxvirus;
an exogenous mammalian gene; and
an exogenous mammalian-active promoter operably linked to said exogenous mammalian gene.

23. The cell of claim 22, wherein the cell is a liver cell.

24. The cell of claim 22, wherein the cell is a human cell.

25. The cell of claim 22, wherein the virus is an insect virus.

26. The cell of claim 25, wherein the virus is a baculovirus.

27. The cell of claim 25, wherein the virus is an entomopox virus.

28. The cell of claim 25, wherein the virus is Aedes Densovirus.

29. The method of claim 2, wherein the insect virus is an entomopox virus.

30. The method of claim 1, wherein said promoter is a cell-type-specific promoter.

31. The method of claim 30, wherein said cell-type-specific promoter is selected from the group consisting of liver cell-specific promoters, neuronal cell-specific promoters, glial cell-specific promoters, kidney cell-specific promoters, spleen cell-specific promoters, lung cell-specific promoters, muscle cell-specific promoters, skin cell-specific promoters, and brain cell-specific promoters.

32. The method of claim 31, wherein said cell-type-specific promoter comprises a liver cell-specific promoter selected from the group consisting of hepatitis viral promoters, α-1-antitrypsin promoters, pyruvate kinase promoters, phosphoenol pyruvate carboxykinase promoters, transferrin promoters, transthyretin promoters, α-fetoprotein promoters, α-fibrinogen promoters, and β-fibrinogen promoters.

33. The method of claim 32, wherein said genome comprises a hepatitis B promoter and further comprises a hepatitis B enhancer.

34. The method of claim 31, wherein said genome comprises an albumin promoter.

35. The method of claim 31, wherein said cell-type-specific promoter comprises a liver cell-specific promoter of a gene encoding a gene product selected from the group consisting of the low density lipoprotein receptor, α2-macroglobulin, α1-antichymotrypsin, α2-HS glycoprotein, haptoglobulin, ceruloplasmin, plasminogen, complement proteins, C3 complement activator, β-lipoprotein, and α1-acid glycoprotein.

36. The method of claim 31, wherein said cell-type-specific promoter is a neuron-specific enolase promoter.

37. The method of claim 1, wherein said promoter is an inducible promoter.

38. The method of claim 37, wherein said inducible promoter is selected from the group consisting of enkephalin promoters, metallothionein promoters, and mouse mammary tumor virus promoters.

39. The method of claim 1, wherein said cell is a liver cell.

40. The method of claim 1, wherein said cell is a kidney cell.

41. The method of claim 1, wherein said cell is a neuronal cell.

42. The method of claim 41, wherein said neuronal cell is selected from the group consisting of fetal neuronal cells, mitral cells, granule cells, and primary neuronal cells.

43. The method of claim 1, wherein said cell is a fibroblast.

44. The method of claim 1, wherein said cell is a brain cell.

45. The method of claim 1, wherein said cell is selected from the group consisting of glial cells, Schwann cells, and astrocytes.

46. The method of claim 1, wherein said cell is a spleen cell.

47. The method of claim 46, wherein said spleen cell is a macrophage.

48. The method of claim 1, wherein said cell is a muscle cell.

49. The method of claim 48, wherein said muscle cell is a myoblast or a myotube.

50. The method of claim 1, wherein said cell is a skin cell.

51. The method of claim 1, wherein said cell is an endothelial cell.

52. The method of claim 1, wherein said cell is an epithelial cell.

53. The method of claim 1, wherein said cell is a HeLa cell.

54. The method of claim 1, wherein said cell is selected from the group consisting of CHO/dhfr⁻ cells, Ramos cells, Jurkat cells, HL60 cells, and K-562 cells.

55. The method of claim 1, wherein said cell is a stem cell.

56. The method of claim 1, wherein said cell is a primary cell.

57. The method of claim 56, wherein said virus is introduced into said primary cell approximately 24 hours after plating of said primary cell.

58. The method of claim 56, further comprising introducing said infected primary cell into a mammal.

59. The method of claim 1, wherein said virus is introduced into said cell in vitro.

60. The method of claim 1, further comprising maintaining said infected cell on a substrate comprising collagen.

61. The method of claim 1, wherein said cell is maintained under in vitro conditions.

62. The method of claim 1, wherein said cell is maintained under in vivo conditions.

63. The method of claim 62, wherein said cell is maintained in a human.

64. The method of claim 1, wherein said mammalian cell is a human cell.

65. The method of claim 1, wherein said virus is introduced into said cell by administering said virus to a mammal comprising said cell.

66. The method of claim 65, wherein said virus is administered intravascularly.

67. The method of claim 65, wherein said virus is administered intranasally.

68. The method of claim 67, wherein said cell is a brain cell, and said administration comprises applying said virus to the nasal mucosa of said mammal.

69. The method of claim 65, wherein said virus is administered by subcutaneous injection.

70. The method of claim 65, wherein said virus is administered to a tissue comprising said cell.

71. The method of claim 70, wherein said virus is administered by perfusing an organ comprising said tissue with a solution comprising said virus.

72. The method of claim 70, wherein said virus is administered by injecting said virus into said tissue.

73. The method of claim 70, wherein said tissue is selected from the group consisting of skin, thyroid, thymus, kidney, muscle, liver, pancreas, brain, bladder, spleen, lung, and trachea.

74. The method of claim 73, wherein the tissue is muscle tissue selected from the group consisting of stomach tissue, uterine tissue, and skeletal muscle tissue.

75. The method of claim 65, wherein said virus is administered to the brain of said mammal by intravenous administration of virus along with induction of osmotic shock.

* * * * *